United States Patent
Satake et al.

(10) Patent No.: US 10,509,036 B2
(45) Date of Patent: Dec. 17, 2019

(54) METHODS OF SELECTING AND ISOLATING CANCER STEM CELLS

(71) Applicant: The Regents of the University of California, Oakland, CA (US)

(72) Inventors: Noriko Satake, David, CA (US); Nitin Nitin, David, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 26 days.

(21) Appl. No.: 15/586,594

(22) Filed: May 4, 2017

(65) Prior Publication Data

US 2018/0011100 A1 Jan. 11, 2018

Related U.S. Application Data

(63) Continuation of application No. PCT/US2015/059269, filed on Nov. 5, 2015.

(60) Provisional application No. 62/075,751, filed on Nov. 5, 2014.

(51) Int. Cl.
*G01N 33/574* (2006.01)
*G01N 33/50* (2006.01)
*G01N 33/58* (2006.01)

(52) U.S. Cl.
CPC ... *G01N 33/57426* (2013.01); *G01N 33/5005* (2013.01); *G01N 33/574* (2013.01); *G01N 33/57407* (2013.01); *G01N 33/582* (2013.01)

(58) Field of Classification Search
CPC ......... G01N 33/57426; G01N 33/5005; G01N 33/574; G01N 33/57407; G01N 33/582
See application file for complete search history.

(56) References Cited

U.S. PATENT DOCUMENTS

| 8,772,463 B2 | 7/2014 | Park et al. |
| 2010/0105574 A1 | 4/2010 | Hansford et al. |
| 2010/0316567 A1 | 12/2010 | Weichert et al. |
| 2014/0011274 A1 | 1/2014 | Clarke et al. |
| 2014/0113325 A1* | 4/2014 | Wu .......... C12Q 1/02 435/34 |

FOREIGN PATENT DOCUMENTS

WO 2016/073737 A1 5/2016

OTHER PUBLICATIONS

Vlashi et al. "Metabolic state of glioma stem cells and nontumorigenic cells."Proc Natl Acad Sci U S A. Sep. 20, 2011;108(38): (Year: 2011).*
Yuan et al. "Isolation of cancer stem cells from adult glioblastoma multiforme."Oncogene. Dec. 16, 2004;23(58):9392-400. (Year: 2004).*
Suganuma et al. "Energy metabolism of leukemia cells: glycolysis versus oxidative phosphorylation."Leuk Lymphoma. Nov. 2010;51(11):2112-9 (Year: 2010).*
Samuels et al. "Bioenergetic modulation overcomes glucocorticoid resistance in T-lineage acute lymphoblastic leukaemia."Br J Haematol. Apr. 2014;165(1):57-66. (Year: 2014).*
Bjerkvig et al., "Cancer stem cells and angiogenesis", Seminars in Cancer Biology, vol. 19, Issue 5, Oct. 2009, pp. 279-284.
Flavahan et al., "Brain tumor initiating cells adapt to restricted nutrition through preferential glucose uptake," Nature Neuroscience, Oct. 2013, vol. 16, No. 10, pp. 1373-1382.
International Application No. PCT/US2015/059269, "PCT Invitation to Pay Additional Fees and Partial Search Report," dated Dec. 30, 2015, 2 pages.
Martins-Neves et al., "Therapeutic implications of an enriched cancer stem-like cell population in a human osteosarcoma cell line," BMC Cancer, 2012, 12:139, 16 pages.
Satake et al., "Leukemia Stem Cells in Acute Lymphoblastic Leukemia: Unveiling Hierarchical Structure at Single Cell Resolution," Blood, 2014, vol. 124, Issue 24, 4786 pages.
Satake et al., "Leukemia Stem Cells in Acute Lymphoblastic Leukemia: Unveiling Hierarchical Structure at Single Cell Resolution," Department of Pediatrics, Stem Cell Program, Genomics Shared Resource, Flow Cytometry Shared Resource, Department of Biological and Agricultural Engineering, UC Davis, Dec. 2014, 1 page.
Vlashi et al., "Metabolic state of glioma stem cells and nontumorigenic cells," PNAS, Sep. 20, 2011, vol. 108, No. 38, pp. 16062-16067.

* cited by examiner

*Primary Examiner* — Titilayo Moloye
(74) *Attorney, Agent, or Firm* — Kilpatrick Townsend & Stockton LLP

(57) ABSTRACT

Provided herein are methods for selecting/identifying and/or isolating cancer stem cells from a biological sample or a cell culture sample using a fluorescent glucose analog. Also provided herein are methods for selecting/identifying and/or isolating leukemia stem cells and subpopulations thereof. The present invention is based, in part, on the discovery that cancer stem cells can be selected/identified based upon a lower level of fluorescence of the fluorescent glucose analog compared to non-cancer stem cells and that specific genes are differentially expressed in leukemia stem cells compared to non-leukemia stem cells.

9 Claims, 16 Drawing Sheets

NBDG High      NBDG Low

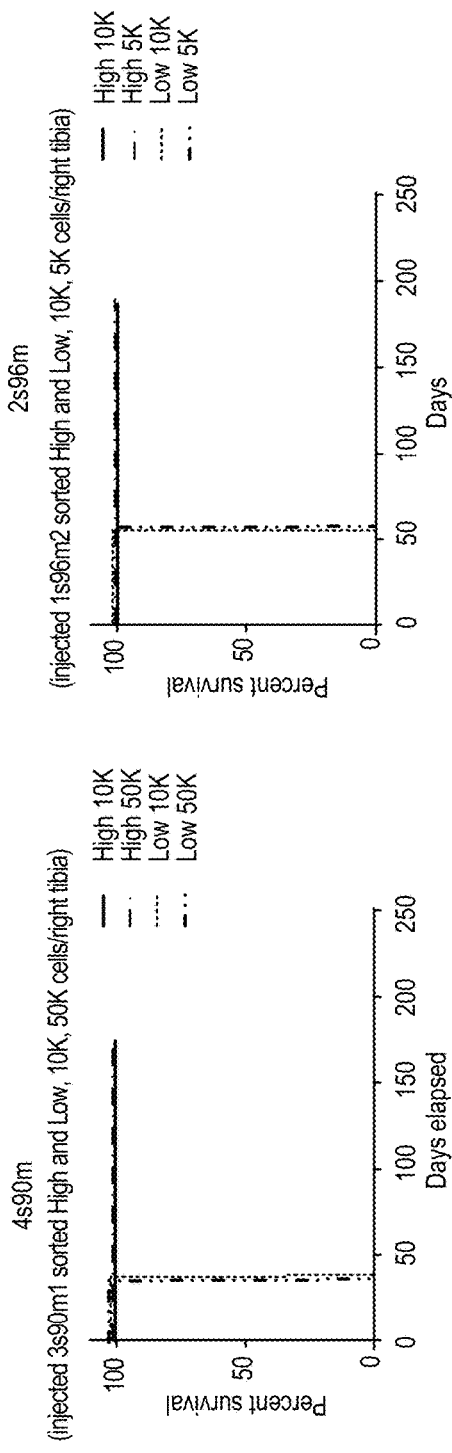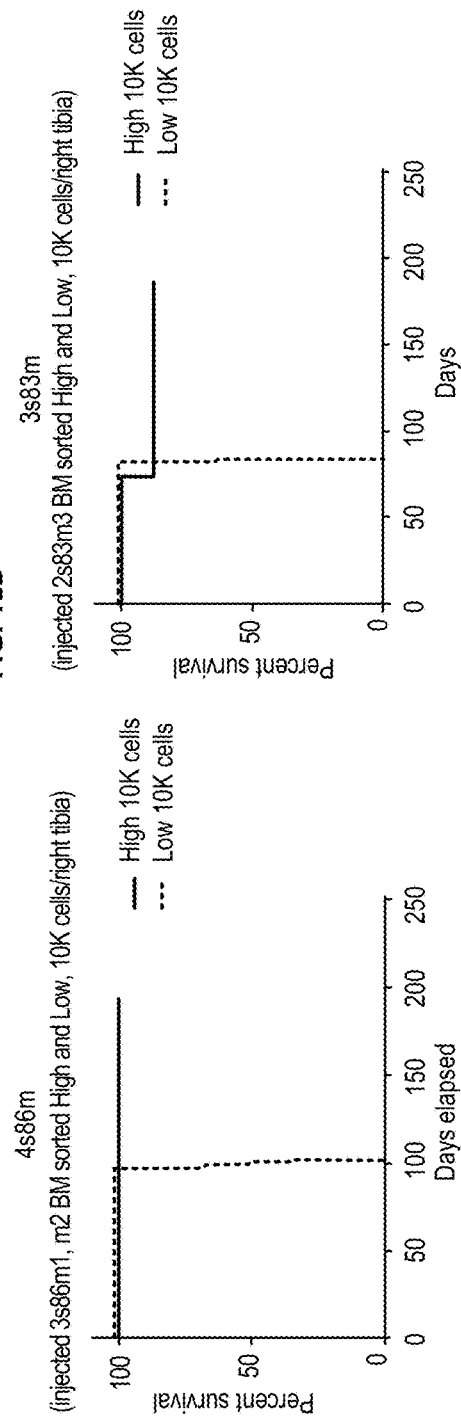

METHODS OF SELECTING AND ISOLATING CANCER STEM CELLS

CROSS-REFERENCES TO RELATED APPLICATIONS

This application is a continuation of International Patent Application No. PCT/US2015/059269, filed Nov. 5, 2015, which claims priority to U.S. Provisional Application No. 62/075,751, filed Nov. 5, 2014, which applications are incorporated herein by reference in their entirety for all purposes.

BACKGROUND OF THE INVENTION

Cancer develops in a hierarchical pattern originating from cancer stem cells (CSCs) that self-renew and give rise to more differentiated cancer cells that are unable to initiate the disease. Cancer stem cells have been identified in several types of cancer, including acute myeloid leukemia (AML), breast cancer, head and neck cancer, glioma, lung cancer, prostate cancer, mesenchymal neoplasm, melanoma, and colon cancer to name a few. Methods of selecting CSCs include using a combination of cell surface markers such as, EpCAM, CD166, CD144, CD133, and CD44.

Cancer stem cells are key to the progression of cancer, and are resistant to chemotherapeutic drugs. CSCs remain quiescent until they become genetically unstable and clonally expand during a pre-cancer disease phase. Afterwards, the CSCs develop or differentiate into different cancer cell types such as progenitor cancer cells, precursor cancer cells, and finally, terminally differentiated cancer cells.

Leukemia stem cells (LSCs) have been characterized in chronic myeloid leukemia (CML) and in some forms of AML (Schurch et al., Front Immunolo, 2013, 4:496). To date, stem cells from acute lymphoblastic leukemia (ALL) have not been identified. LSCs are resistant to most current treatments such as radiotherapy and chemotherapy. Thus, LSCs are considered the main cause of drug resistance and disease relapse.

Challenges remain for isolating CSCs including LSCs because CSCs are phenotypically heterogeneous and are relatively unstable. There remains a need in the art for methods of isolating CSCs from an individual or from cell culture, such that these cells can be, for example, studied further or used to develop targeted therapies for cancer. The present invention provides novel methods that satisfy this need and are advantageous over the current methods for isolating CSC, including LSCs.

BRIEF SUMMARY OF THE INVENTION

In one aspect of the present invention, provided herein is a method for selecting cancer stem cells from a sample. The method comprises: (a) incubating the sample with a fluorescent glucose analog under suitable conditions, wherein the sample comprises cancer stem cells and non-cancer stem cells (e.g., cancer cells that are not cancer stem cells); and (b) selecting the cancer stem cells from the sample based upon a lower level of fluorescence compared to the non-cancer stem cells. In some embodiments, the method also includes isolating the cancer stem cells. In certain instances, the cancer stem cells are isolated by separating or purifying the cancer stem cells from the non-cancer stem cells in the sample.

In some embodiments, the method is useful for isolating cancer stem cells from a sample. The method can include: (a) incubating the sample with a fluorescent glucose analog under suitable conditions, wherein the sample comprises cancer stem cells and non-cancer stem cells (e.g., cancer cells that are not cancer stem cells); (b) detecting (e.g., measuring) a lower level of fluorescence in cancer stem cells in the sample compared to non-cancer stem cells; and (c) isolating (e.g., separating or purifying) the cancer stem cells from the non-cancer stem cells in the sample.

In some embodiments, the cancer stem cells are capable of initiating cancer in an animal model, such as a xenograft mouse model. In some cases, the isolated cancer stem cells are transplanted or injected into a xenograft animal model to evaluate the cancer initiating activity of the cells.

In some embodiments, the non-cancer stem cells have highly efficient glucose uptake. The cells that are not cancer stem cells can have a high rate of glucose uptake compared to cancer stem cells and/or normal cells. In some cases, a high rate of glucose uptake refers to a rate that is about 2 to about 200 times higher than that of a cancer stem cell and/or a normal, non-cancer cell. In other cases, a high rate of glucose uptake refers to a rate that is at least about 1-log higher (e.g., between about 1-log to about 3-log higher or about 1-log, 2-log, or 3-log higher) than that of a cancer stem cell and/or a normal, non-cancer cell.

In some embodiments, the sample is a biological sample or a cell culture sample. In some instances, the biological sample is selected from the group consisting of bone marrow, blood, plasma, serum, cerebrospinal fluid, a tumor biopsy, a tissue biopsy, a fine needle aspirate, circulating tumor cells, and combinations thereof. The biological sample can be obtained from a subject with cancer, e.g., a human cancer patient. In some embodiments, the cancer is selected from the group consisting of a hematologic malignancy, bladder cancer, neuroblastoma, glioblastoma, melanoma, breast cancer, colon cancer, ovarian cancer, pancreatic cancer, prostate cancer, and other solid tumor cancers. In some instances, the hematologic malignancy is selected from the group consisting of acute lymphoblastic leukemia (ALL), acute myeloid leukemia (AML), chronic lymphocytic leukemia (CLL), chronic myeloid leukemia (CML), acute monocytic leukemia, Hodgkin's lymphomas, non-Hodgkin's lymphomas, multiple myeloma, myeloproliferative neoplasms, myeloid and lymphoid neoplasms associated with eosinophilia, myelodysplastic/myeloproliferative neoplasms, myelodysplastic syndrome, neoplasms related to AML, acute leukemias of ambiguous lineage, precursor B-cell neoplasms, mature B-cell neoplasms, precursor T-cell neoplasms, mature T-cell neoplasms, mast cell diseases, histiocytic sarcoma, dendritic cell neoplasms, posttransplantation lymphoproliferative disorders, and a combination thereof. Acute lymphoblastic leukemia can be B-cell ALL (e.g., precursor B cell ALL and mature B cell ALL) or T-cell ALL (e.g., precursor T cell ALL or mature T cell ALL).

In some embodiments, the cell culture sample comprises cells from a cancer cell line, e.g., a human cancer cell line. In some instances, the cancer cell line is a cell line of a hematologic malignancy, e.g., a leukemia cell line. The cell line of a hematologic malignancy can be an acute lymphoblastic leukemia (ALL) cell line, an acute myeloid leukemia (AML) cell line, or a chronic myelogenous leukemia (CML) cell line. In other instances, the cancer cell line is a neuroblastoma cell line. Non-limiting examples of cancer cell lines are described in, e.g., Barretina et al., Nature, 2012, 483(7391):603-607.

In some embodiments, the fluorescent glucose analog is selected from the group consisting of 2-[N-(7-nitrobenz-2-oxa-1,3-diaxol-4-yl)amino]-2-deoxyglucose (2-NBDG), 6-deoxy-N-(7-nitrobenz-2-oxa-1,3-diazol-4-yl)aminoglucose (6-NBDG), pyro-2DG, Cy5.5-D-glucosamine (Cy5.5-2DG), Cy3-linked O-1-glycosylated glucose (Cy3-α-glucose and Cy3-β-glucose), IRDye 800CW 2-DG, CyNE 2-DG, GB3-Cy3, other fluorescent glucose analogs, and combinations thereof.

In some embodiments, the cancer stem cells are selected using flow cytometry. The level of fluorescence can be detected or measured using flow cytometry. In some instances, the lower level of fluorescence of the cancer stem cells is at least about 1-log lower (e.g., between about 1-log to about 3-log lower or about 1-log, 2-log, or 3-log lower) compared to the non-cancer stem cells.

In another aspect of the present invention, provided herein is a method for identifying a leukemia stem cell in a sample. The method comprises (a) detecting or measuring the expression level of at least one leukemia stem cell marker of Tables 1, 2, 3, or 4 in a cell from the sample, wherein the sample comprises leukemia stem cells and non-leukemia stem cells (e.g., leukemia cells that are not leukemia stem cells); (b) comparing the expression level of the at least one leukemia stem cell marker in the cell to the expression level of the same leukemia stem cell marker in a non-leukemia stem cell; and (c) determining that the cell is a leukemia stem cell if the expression level of the at least one leukemia stem cell marker is higher or lower in the cell compared to the expression level of the same leukemia stem cell marker in the non-leukemia stem cell.

In some embodiments, the cell from the sample is identified as a leukemia stem cell if the expression level of at least one leukemia stem cell marker is higher in the cell compared to the level of the same marker in a non-leukemia stem cell. In other embodiments, the cell from the sample is identified as a leukemia stem cell if the expression level of at least one leukemia stem cell marker is lower in the cell compared to the level of the same marker in a non-leukemia stem cell. Where the expression level of a plurality of leukemia stem cell markers is detected or measured, the leukemia stem cell can be identified based upon a higher or lower expression level of each of the leukemia stem cell markers compared to the level of the same marker in a non-leukemia stem cell.

In some embodiments, provided herein is a method for isolating a leukemia stem cell in a sample. The method includes (a) detecting or measuring the expression level of at least one leukemia stem cell marker of Tables 1, 2, 3, or 4 in a cell from the sample, wherein the sample comprises leukemia stem cells and non-leukemia stem cells (e.g., leukemia cells that are not leukemia stem cells); and (b) isolating (e.g., separating or purifying) the leukemia stem cell having a higher or lower expression level of the at least one leukemia stem cell marker compared to a non-leukemia stem cell. Where the expression level of a plurality of leukemia stem cell markers is detected or measured, the leukemia stem cell can be isolated based upon a higher or lower expression level of each of the leukemia stem cell markers compared to the level of the same marker in a non-leukemia stem cell.

In some embodiments, the expression level of at least 20, at least 50 or at least 90 leukemia stem cell markers of Table 1 is detected. In other embodiments, the expression level of at least 50 leukemia stem cell markers of Table 2 is detected. In yet other embodiments, the expression level of at least 20, at least 40, or at least 60 leukemia stem cell markers of Table 3 is detected. In some embodiments, the expression level of at least 20, at least 50 or at least 90 leukemia stem cell markers of Table 4 is detected.

In some embodiments, the expression level of leukemia stem cell marker Nos. 1-121 of Table 1 is detected. In other embodiments, the expression level of leukemia stem cell marker Nos. 1-93 of Table 2 is detected. In yet other embodiments, the expression level of leukemia stem cell marker Nos. 1-80 of Table 3 is detected. In another embodiment, the expression level of leukemia stem cell marker Nos. 1-105 of Table 4 is detected.

In some embodiments, the sample is a biological sample or a cell culture sample. In some instances, the biological sample is selected from the group consisting of bone marrow, blood, plasma, serum, cerebrospinal fluid, circulating tumor cells, or a combination thereof. The biological sample can be obtained from a subject with acute lymphoblastic leukemia. In some embodiments, the cell culture sample comprises cells from an acute lymphoblastic leukemia cell line. In some instances, the acute lymphoblastic leukemia (ALL) is B-cell ALL or T-cell ALL.

In some instances, the leukemia stem cell is a B-cell ALL stem cell if the expression level of at least one leukemia stem cell marker selected from the group consisting of leukemia stem cell marker Nos. 1-9 of Table 3 and is higher than in the non-leukemia stem cell. In other instances, the leukemia stem cell is a B-cell ALL stem cell if the expression level of at least one leukemia stem cell marker selected from the group consisting of leukemia stem cell marker Nos. 10-80 of Table 3 is lower than in the non-leukemia stem cell. In yet other instances, the leukemia stem cell is a B-cell ALL stem cell if the expression level of at least one leukemia stem cell marker selected from the group consisting of leukemia stem cell marker Nos. 1-9 of Table 3 is higher than in the non-leukemia stem cell, and the expression level of at least one leukemia stem cell marker selected from the group consisting of leukemia stem cell marker Nos. 10-80 of Table 3 is lower than in the non-leukemia stem cell.

In some instances, the leukemia stem cell is a T-cell ALL stem cell if the expression level of at least one leukemia stem cell marker selected from the group consisting of leukemia stem cell marker Nos. 1-19 of Table 4 is higher than in the non-leukemia stem cell. In other instances, the leukemia stem cell is a T-cell ALL stem cell if the expression level of at least one leukemia stem cell marker selected from the group consisting of leukemia stem cell marker Nos. 20-105 of Table 4 is lower than in the non-leukemia stem cell. In yet other instances, the leukemia stem cell is a T-cell ALL stem cell if the expression level of at least one leukemia stem cell marker selected from the group consisting of leukemia stem cell marker Nos. 1-19 of Table 4 is higher than in the non-leukemia stem cell, and the expression level of at least one leukemia stem cell marker selected from the group consisting of leukemia stem cell marker Nos. 20-105 of Table 4 is lower than in the non-leukemia stem cell.

In some embodiments, the leukemia stem cells described above are capable of initiating leukemia in an animal model, such as a xenograft mouse model.

In yet another aspect of the present invention, provided herein is a method for identifying a subpopulation of leukemia stem cells in a sample. The method comprises (a) detecting or measuring the expression level of at least one leukemia stem cell marker of Table 2 in a heterogeneous population of leukemia stem cells from the sample; (b) comparing the expression level of the at least one leukemia stem cell marker between different leukemia stem cells in the heterogeneous population of leukemia stem cells; and (c) identifying a subpopulation of leukemia stem cells based upon a higher or lower expression level of the at least one leukemia stem cell marker compared to the other leukemia stem cells in the heterogeneous population of leukemia stem cells. Where the expression level of a plurality of leukemia stem cell markers of Table 2 is detected or measured, the subpopulation of leukemia stem cells can be identified based upon a higher or lower expression level of each of the leukemia stem cell markers compared to the other leukemia stem cells in the heterogeneous population. In some embodiments, the method further comprises isolating (e.g., separating or purifying) the identified subpopulation of leukemia stem cells from other leukemia stem cells in the heterogeneous population.

In another aspect, provided herein is a method for isolating a subpopulation of leukemia stem cells in a sample. The method comprises (a) detecting or measuring the expression level of at least one leukemia stem cell marker of Table 2 in a heterogeneous population of leukemia stem cells from the sample; and (b) isolating (e.g., separating or purifying) a subpopulation of leukemia stem cells based upon a higher or lower expression level of the at least one leukemia stem cell marker compared to the other leukemia stem cells in the heterogeneous population of leukemia stem cells. Where the expression level of a plurality of leukemia stem cell markers of Table 2 is detected or measured, the subpopulation of leukemia stem cells can be isolated based upon a higher or lower expression level of each of the leukemia stem cell markers compared to the other leukemia stem cells in the heterogeneous population.

In some embodiments, the expression level of at least 20 leukemia stem cell markers of Table 2 is detected. In other embodiments, the expression level of at least 50 leukemia stem cell markers of Table 2 is detected. In another embodiment, the expression level of at least 90 leukemia stem cell markers of Table 2 is detected. In yet another embodiment, the expression level of leukemia stem cell markers No. 1-93 of Table 2 is detected.

In some embodiments, step (a) of the method also includes: (i) incubating the sample with a fluorescent glucose analog under suitable conditions; (ii) measuring a lower level of fluorescence in a heterogeneous population of leukemia stem cells from the sample compared to non-leukemia stem cells; and (iii) isolating the heterogeneous population of leukemia stem cells. In some instances, the non-leukemia stem cells have highly efficient glucose uptake.

In some embodiments, the sample is a biological sample or a cell culture sample. In some instances, the biological sample is selected from the group consisting of bone marrow, blood, plasma, serum, cerebrospinal fluid, or circulating tumor cells, or a combination thereof. The biological sample can be obtained from a subject with acute lymphoblastic leukemia. In some embodiments, the cell culture sample comprises cells from an acute lymphoblastic leukemia cell line. In some instances, the acute lymphoblastic leukemia (ALL) is B-cell ALL or T-cell ALL.

In some embodiments, the fluorescent glucose analog is selected from the group consisting of 2-[N-(7-nitrobenz-2-oxa-1,3-diaxol-4-yl)amino]-2-deoxyglucose (2-NBDG), 6-deoxy-N-(7-nitrobenz-2-oxa-1,3-diazol-4-yl)aminoglucose (6-NBDG), pyro-2DG, Cy5.5-D-glucosamine (Cy5.5-2DG), Cy3-linked O-1-glycosylated glucose (Cy3-α-glucose and Cy3-β-glucose), IRDye 800CW 2-DG, CyNE 2-DG, GB3-Cy3, other fluorescent glucose analogs, and combinations thereof.

In some embodiments, the cancer stem cells are selected using flow cytometry. In some instances, the lower level of fluorescence of the cancer stem cells is at least about 1-log lower (e.g., between about 1-log to about 3-log lower or about 1-log, 2-log, or 3-log lower) compared to the non-cancer stem cells.

In some embodiments, the leukemia stem cells are capable of initiating leukemia in an animal model, e.g., a xenograft animal model.

In another aspect, provided herein is a method of isolating leukemia stem cells of B-cell type acute lymphoblastic leukemia (B-cell ALL) from a sample (e.g., a biological sample or a cell culture sample). The sample can be a B-cell ALL cell line or a sample obtained from a patient with B-cell ALL. The method includes: (a) incubating the sample with a fluorescent glucose analog under suitable conditions, (b) measuring or detecting the level of fluorescence in the sample using, for example, flow cytometry; and (c) isolating (e.g., separating or purifying) the leukemia stem cells having a lower level of fluorescence compared to the non-leukemia stem cells in the sample. Optionally, the isolated leukemia stem cells can be confirmed to be stem cells of B-cell ALL by detecting a higher or lower expression level of at least one leukemia stem cell marker of Table 3 in an isolated leukemia stem cell compared to a non-leukemia stem cell. In some embodiments, a higher expression level of at least one leukemia stem cell marker selected from the group consisting of leukemia stem cell marker Nos. 1-9 of Table 3 indicates that the isolated leukemia stem cells are B-cell ALL stem cells. In other embodiments, a lower expression level of at least one leukemia stem cell marker selected from the group consisting of leukemia stem cell marker Nos. 10-80 of Table 3 indicates that the isolated leukemia stem cells are B-cell ALL stem cells. In yet other embodiments, a higher expression level of at least one leukemia stem cell marker selected from the group consisting of leukemia stem cell marker Nos. 1-9 of Table 3 in combination with a lower expression level of at least one leukemia stem cell marker selected from the group consisting of leukemia stem cell marker Nos. 10-80 of Table 3 indicates that the isolated leukemia stem cells are B-cell ALL stem cells.

In another aspect, provided herein is a method of isolating leukemia stem cells of T-cell type acute lymphoblastic leukemia (T-cell ALL) from a sample (e.g., a biological sample or a cell culture sample). The sample can be a T-cell ALL cell line or a sample obtained from a patient with T-cell ALL. The method includes: (a) incubating the sample with a fluorescent glucose analog under suitable conditions, (b) measuring or detecting the level of fluorescence in the sample using, for example, flow cytometry; and (c) isolating (e.g., separating or purifying) the leukemia stem cells having a lower level of fluorescence compared to the non-leukemia stem cells in the sample. Optionally, the isolated leukemia stem cells can be confirmed to be stem cells of T-cell ALL by detecting a higher or lower expression level of at least one leukemia stem cell marker of Table 4 in an isolated leukemia stem cell compared to a non-leukemia stem cell. In some embodiments, a higher expression level of at least one leukemia stem cell marker selected from the group consisting of leukemia stem cell marker Nos. 1-19 of Table 4 indicates that the isolated leukemia stem cells are T-cell ALL stem cells. In other embodiments, a lower expression level of at least one leukemia stem cell marker selected from the group consisting of leukemia stem cell marker Nos. 20-105 of Table 4 indicates that the isolated leukemia stem cells are T-cell ALL stem cells. In yet other embodiments, a higher expression level of at least one leukemia stem cell marker selected from the group consisting of leukemia stem cell marker Nos. 1-19 of Table 4 in combination with a lower expression level of at least one leukemia stem cell marker selected from the group consisting of leukemia stem cell marker Nos. 20-105 of Table 4 indicates that the isolated leukemia stem cells are T-cell ALL stem cells.

Other objects, features, and advantages of the present invention will be apparent to one of skill in the art from the following detailed description and figures.

BRIEF DESCRIPTION OF THE DRAWINGS

FIG. 11 also shows that the leukemia stem cells are smaller in size compared to the non-leukemia stem cells.

FIGS. 12A-D illustrate that mice transplanted with the patient derived leukemia stem cells of FIG. 11 developed leukemia between 5-14 weeks post-transplantation, whereas mice transplanted with the cells having a high level of NBDG did not develop the disease within the same timeframe or by the end of the study, which was more than 4 months after the LSC group developed leukemia. None of the mice transplanted with NBDG high cells developed leukemia. The data clearly show that NBDG low cells initiate leukemia whereas NBDG high cells do not, thereby indicating that NBDG low cells are LSCs. FIG. 12A shows a Kaplan Meier survival curve for NOD/SCID/IL-2R$\gamma^{-/-}$ (NSG) mice injected with 10,000 cells or 50,000 cells from either NBDG low cells or NBDG high cells. FIG. 12B shows a Kaplan Meier survival curve for NSG mice injected with 5,000 cells or 10,000 cells from either NBDG low cells or NBDG high cells. FIG. 12C shows a Kaplan Meier survival curve for NSG mice injected with 10,000 cells from either NBDG low cells or NBDG high cells. FIG. 12D shows a Kaplan Meier survival curve for NSG mice injected with 10,000 cells from either NBDG low cells or NBDG high cells.

FIG. 13A shows Kaplan Meier curves of mice injected with the 1s83m3 sample of NBDG high and low cells. FIG. 13B shows Kaplan Meier curves of mice injected with the 2s89m3 sample of NBDG high and low cells.

FIG. 14 shows hierarchical clustering of single-cell gene expression data obtained using the C1 Single-Cell Auto Prep and BioMark HD System (Fluidigm Corp., South San Francisco, Calif.) of the primary ALL sample harvested from the xenograft mouse model (2s83).

DETAILED DESCRIPTION OF THE INVENTION

I. Introduction

Figure 1A:
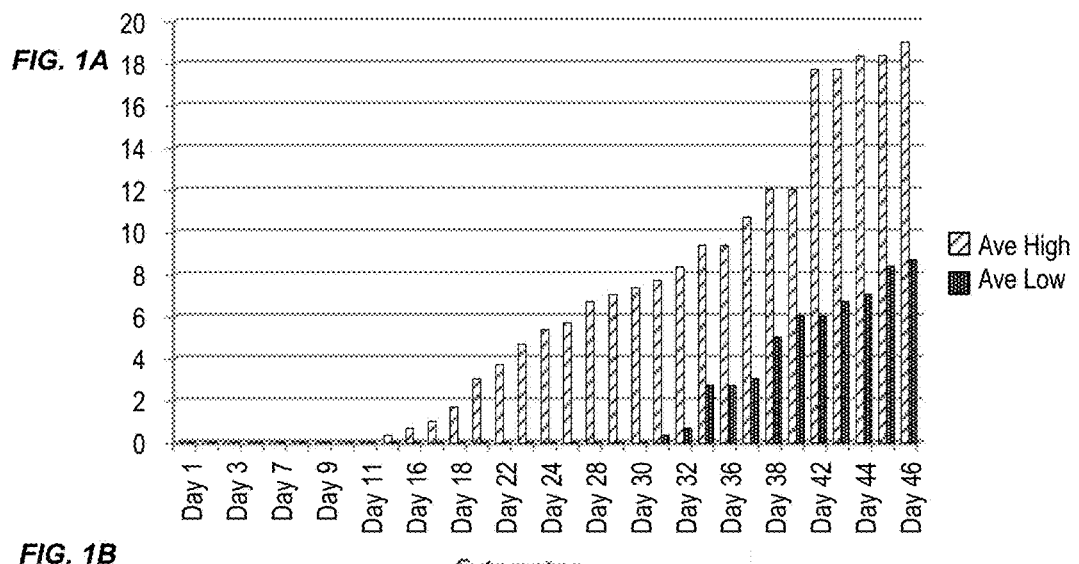
FIGS. 1A-C show that a distinct population of NBDG low cells identified in the JM1 pre-B lymphoblast cell line derived from a patient with immunoblastic B cell lymphoma-leukemia. These cells have less in vitro colony forming capability compared to the corresponding NBDG high cells (FIG. 1A). The NBDG low cells have lower HLA expression compared to the NBDG high cells (FIG. 1B) and are also smaller in size as determined by phase contrast microscopy (FIG. 1C).

Provided herein are methods for selecting and optionally isolating cancer stem cells, including leukemia stem cells (LSCs), from a sample comprising cancer stem cells and non-cancer stem cells. The present invention is based, in part, on the surprising discovery that cancer stem cells can be selected based upon a lower level of fluorescence of a fluorescent glucose analog compared to non-cancer stem cells. Also provided herein are methods for selecting and optionally isolating leukemia stem cells based upon the detection of leukemia stem cell markers that are differentially expressed in LSCs (Tables 1 and 2), B-cell ALL stem cells (Table 3), and T-cell ALL stem cells (Table 4) versus non-LSCs. Moreover, a subpopulation of LSCs can be identified and optionally isolated from a heterogeneous population of LSCs based upon the differential expression of specific leukemia stem cell markers described in Table 2.

Isolated cancer stem cells described herein are useful for the development of cancer stem cell-targeted therapeutics. These cells can be used, for example, in drug screening methods. The distinct subpopulations of leukemia stem cells can be used in experimental analysis to determine or predict disease progression, relapse, and/or the development of disease resistance.

II. Definitions

As used herein, the following terms have the meanings ascribed to them unless specified otherwise.

The term "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

As used herein, the terms "about" or "approximately", unless otherwise indicated, refer to a value that is no more than 10% above or below the value being modified by the term.

The term "biological sample" encompasses a variety of sample types obtained from an organism or a cell line. The term encompasses blood and other liquid samples of biological origin, solid tissue samples, such as a biopsy specimen or tissue cultures or cells derived therefrom and the progeny thereof. The term includes samples that have been manipulated in any way after their procurement, such as by treatment with reagents, solubilization, or enrichment for certain components. The term includes a clinical sample, and also includes cells in cell culture, cell supernatants, cell lysates, serum, plasma, biological fluids, and tissue samples.

The terms "individual," "subject," "host," and "patient," used interchangeably herein and refer to any mammalian subject for whom diagnosis, treatment, or therapy is desired, particularly humans.

The terms "cancer," "neoplasm," "tumor," and "carcinoma," are used interchangeably herein to refer to cells which exhibit relatively autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. Types of cancer that can be used in the present invention include, but are not limited to, hematologic malignancies (e.g., leukemia, lymphoma, and myeloma), pancreatic cancer, prostate cancer, breast cancer, skin cancer, gastrointestinal cancer, lung cancer, hepatocellular carcinoma, cervical cancer, endometrial cancer, ovarian cancer, fallopian tube cancer, vaginal cancer, liver cancer, bile duct cancer, bladder cancer, urinary tract cancer, thyroid cancer, adrenal cancer, kidney cancer, other organ tissue cancers, liposarcoma, leiomyosarcoma, rhabdomyosarcoma, synovial sarcoma, angiosarcoma, fibrosarcoma, malignant peripheral nerve tumor, gastrointestinal stromal tumor, desmoid tumor, Ewing's sarcoma, osteosarcoma, chondrosarcoma, and other sarcomas. See, e.g., Kumar V, Abbas A K, Fausio N. Robbins and Cotran, *Pathologic Basis of Disease.* 7th Ed. "Unit I: General Pathology, 7: Neoplasia, Biology of tumor growth: Benign and malignant neoplasms". 269-342, 2005.

As used herein, the term "hematologic malignancy" refers to a cancer that originates in a blood-forming tissue such as bone marrow, or in cells of the immune system. Types of hematologic malignancies include leukemias, lymphomas, and myelomas. Classifications or types of hematologic malignancies include those set forth in the Rappaport Classification of Lymphoma, Kiel Classification of Lymphoma, the Working Formulation for Non-Hodgkin Lymphoma, the Revised European American Lymphoma Classification (REAL), and the World Health Organization (WHO) classifications, and by the National Cancer Institute of the National Institutes of Health. Descriptions of the WHO classifications are found in, e.g., Vardiman et al., *Blood,* 2009, 114(5):937-951 and Campo et al., *Blood,* 2011, 117 (19):5019-5032. The term "leukemia" refers to a blood cancer starting in blood-forming cells (e.g., lymphoid cells or myeloid cells). Leukemia cells are found mainly in the bone marrow and blood. The term "lymphoma" refers to a blood cancer starting in the lymphatic system such as a lymphocyte, lymph node cell or lymphatic tissue.

The term "acute lymphoblastic leukemia" or "ALL" refers to an aggressive hematological tumor resulting from the malignant transformation of hematopoietic lymphoid progenitors. It is the most frequent leukemia in childhood, with a peak incidence from ages 3 to 5 years. It also occurs in adolescents and has a second, lower peak in adults. ALL develops from early forms of lymphocytes. It can start in either early B lymphocytes (B cells) or T lymphocytes (T cells) at different stages of maturity. ALL starting in T-cells is called T-cell ALL and abbreviated T-ALL; similarly, ALL starting in B-cells is called B-cell ALL and abbreviated B-ALL.

Clinical diagnosis of ALL relies widely on morphology, although genetic abnormalities resulting from chromosomal translocations are used for diagnostic purposes. However, only in 60% of children with ALL, genetic abnormalities are detected with present technologies (Mrozek et al., *Blood Rev* 2004; 18(2):115-36).

Treatment generally emphasizes early introduction of an intensive multi-drug regimen, which may include prednisone, vincristine, anthracycline, asparaginase or methotrexate. Other drugs and combinations include cytarabine and etoposide, and cyclophosphamide. Relapse usually occurs in the bone marrow but may also occur in the central nervous system or testes, alone or concurrent with bone marrow. Although second remissions can be induced in many children, subsequent remissions tend to be brief.

Conventional chemotherapy treatment includes nucleoside therapy, for example with a combination of 6-mercaptopurine (6-MP) and 6-thioguanine (6-TG). However, despite intensive chemotherapy, 20% of pediatric and over 50% of adult acute lymphoblastic leukemia patients show transient responses to treatment and ultimately die from the disease.

The term "acute myeloid leukemia" or "AML" refers to a cancer of the myeloid line of blood cells, characterized by the rapid growth of abnormal white blood cells, e.g., hematopoietic progenitor cells that accumulate in the bone marrow and interfere with the production of normal blood cells. AML progresses rapidly and is typically fatal within weeks or months if left untreated. AML is the most prevalent form of adult leukemia, particularly among the elderly and is slightly more common in men than women. AML accounts for approximately 1.2% of all cancer deaths. The 5 year survival rates for AML are low, driven by therapy failure and patients relapsing. Among patients<65 the 5 year survival rate is 34.4%, among patients>65 it is only 5%. AML can also be referred to as acute myelocytic leukemia, acute myelogenous leukemia, acute granulocytic leukemia, or acute lymphocytic leukemia. The term AML includes all subtypes of AML according to, for example, the World Health Organization (WHO) classification or the French-American-British (FAB) classification of AML.

The pathogenesis of AML is a multi-step process affecting cell differentiation, proliferation and apoptosis that ultimately lead to malignant transformation of hematopoietic progenitors. Without intending to be bound by any particular theory, at least two, probably in most cases multiple, hits are required for leukemic transformation. For instance, one hit may be a genetic abnormality that results in constitutive activation of proliferative signaling and involves signaling molecules and another hit may be lesions, such as formation of fusion genes, as a result of the chromosomal abnormalities involving transcription factors that result in a block of myeloid differentiation.

"Neuroblastoma" refers to a tumor that develops from the sympathetic nervous system, such as the adrenal gland or sympathetic ganglia (Brodeur, Nat. Rev. Cancer, 2003, 3:203-216). It is one of the most frequent solid tumors in children. It is the most common malignancy diagnosed in the first year of life and shows a wide range of clinical phenotypes with some patients having tumors that regress spontaneously, whereas the majority of patients have aggressive metastatic disease (Maris et al., Lancet, 2007, 369:2106-20). These latter neuroblastoma cases have survival probabilities of less than 40% despite intensive chemoradiotherapy, and the disease continues to account for 15% of childhood cancer mortality (Maris et al. (2007) Lancet, 369:2106-20; Matthay et al. (1999) N. Eng. J. Med., 341:1165-73). The cancer can start in neuroblasts (e.g., early nerve cells) of the sympathetic nervous system. The term neuroblastoma includes any stage of the cancer as determined according to, for example, the International Neuroblastoma Staging System (INSS) or the International Neuroblastoma Risk Group Staging System (INRGSS).

The term "normal" as used in the context of "normal cell," is meant to refer to a cell of an untransformed phenotype or exhibiting a morphology of a non-transformed cell of the tissue type being examined. A "cancer cell" refers to a cell of a cancer that can be identified by abnormalities in, for example, cell growth or proliferation (e.g., uncontrolled growth or proliferation), regulation of the cell cycle, cell mobility, cell-cell interaction, or metastasis, etc.

The term "leukemia" as used herein means any disease involving the progressive proliferation of abnormal leukocytes found in hematopoietic tissues, other organs and usually in the blood in increased numbers. For example, leukemia includes acute lymphocytic leukemia (ALL), acute myeloid leukemia (AML), chronic lymphocytic leukemia (CLL) and chronic myelogenous leukemia (CML), including cytogenetically normal and abnormal subtypes.

The term "leukemic cell" or "leukemia cell" refers to an abnormal white blood cell found in leukemia. A leukemic cell includes leukemia stem cells, lymphoid blast cells, lymphoblasts, myeloblasts, leukemia specific B cells, leukemia specific T cells, differentiated leukemia stem cells, precursor leukemia stem cells, and progenitor leukemia stem cells.

The term "cancer stem cell" refers to a cell of a cancer, such as a solid tumor, that has the ability to perpetuate through self-renewal and to generate other cells of the cancer through differentiation or to generate new tumors and/or lead to metastatic disease.

The term "leukemia stem cell" refers to a cancer stem cell that can initiate leukemia, which is a cancer of leukocytes, e.g., white blood cells.

The term "non-cancer stem cell" refers to a cell that may be of a cancer and is not a cancer stem cell. A non-cancer stem cell may be a differentiated cancer cell, a precursor cancer cell, a progenitor cancer cell, or another cancer cell that is not a cancer stem cell.

The term "marker" in the context of a cell or tissue (e.g. a normal or cancer cell or cancer stem cell) means any gene product, e.g., non-coding RNA (non-messenger RNA), mRNA and polypeptide, antigen, molecule or other chemical or biological entity that is specifically found in or on a cell of interest and can be used to identify the cell affected by a disease or disorder.

The term "expression level" when referring to a cell marker such as a leukemia stem cell marker, refers to the measurable quantity of a gene product produced by the gene in a sample of a patient wherein the gene product can be a transcriptional product or a translated transcriptional product. Accordingly, the expression level can pertain to a nucleic acid gene product such as RNA or cDNA or a polypeptide. The expression level is derived from a biological sample, a subject's sample, a cell culture sample, and/or a control sample, and can for instance be detected de novo or correspond to a previous determination.

The term "detecting an expression level" or "expression level is detected" as used in reference to a gene means the application of a method to a sample, e.g., a subject sample, a biological sample, a cell culture sample, and a control sample, for ascertaining quantitatively, semi-quantitatively or qualitatively the amount of a gene expression product, e.g., RNA, mRNA or polypeptide product. For example, a level of a gene expression can be determined by a number of methods including, but not limited to, arrays and other hybridization based methods and PCR protocols. In some instances, the PCR methods include a probe or primer or primer set that are used to ascertain the amount of nucleic acid of the gene. For example, an expression level of a gene can be determined using a probeset or one or more probes of the probeset, described herein for a particular gene. In addition more than one probeset where more than one exists, can be used to determine the expression level of the gene.

Other examples of methods for detecting the amount of gene expression product present in a sample include Nanostring® technology, serial analysis of gene expression (SAGE), RNA sequencing, RNase protection assays, and Northern Blot. The polypeptide level can be determined by an immunoassay, such as western blot, flow cytometry, immunohistochemistry, ELISA, immunoprecipation and the like, where a gene or gene signature detection agent such as an antibody, for example, a labeled antibody specifically binds the polypeptide product encoded by the gene and the relative or absolute amount of polypeptide in a sample can be ascertained.

The term "a higher or lower expression level of a leukemia stem cell marker" refers to the level or amount of a polynucleotide that represents or corresponds to a gene that is differentially expressed in a cancer stem cell when compared to a cell that is not a cancer stem cell, e.g., a level of mRNA that is at least about 25%, at least about 50%, at least about 90%, at least about 100%, at least about 1.5-fold, at least about 2-fold, at least about 2.5-fold, at least about 3-fold, at least about 3.5-fold, at least about 4-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10-fold, at least about 25-fold, or at least about 50-fold higher or lower in a cancer stem cell versus a cell that is not a cancer stem cell.

III. Detailed Description of the Embodiments

The methods provided herein can be used to select and isolate cancer stem cells from a mixed population of cells from an individual or a cell culture sample based on differences in glucose uptake. Leukemia stem cells (e.g., B-cell ALL stem cells or T-cell ALL stem cells) can also be separated from non-leukemia stem cells using stem cell markers. Furthermore, a subpopulation of leukemia stem cells can be isolated from a heterogeneous population of cells including leukemia stem cells.

A. Obtaining Biological Samples Containing Cancer Stem Cells

The present invention provides a method for selecting and/or isolating cancer stem cells from a biological sample or a cell culture sample. Any biological sample obtained from a subject having cancer or suspected of having cancer can be used. The subject can have a hematologic malignancy, bladder cancer, neuroblastoma, glioblastoma, melanoma, breast cancer, colon cancer, ovarian cancer, pancreatic cancer, prostate cancer, and other solid tumor cancers.

In some instances, the hematologic malignancy is selected from acute lymphoblastic leukemia (ALL), acute myeloid leukemia (AML), chronic lymphocytic leukemia (CLL), chronic myeloid leukemia (CML), acute monocytic leukemia, Hodgkin's lymphomas, non-Hodgkin's lymphomas, multiple myeloma, myeloproliferative neoplasms, myeloid and lymphoid neoplasms associated with eosinophilia, myelodysplastic/myeloproliferative neoplasms, myelodysplastic syndrome, neoplasms related to AML, acute leukemias of ambiguous lineage, precursor B-cell neoplasms, mature B-cell neoplasms, precursor T-cell neoplasms, mature T-cell neoplasms, mast cell diseases, histiocytic sarcoma, dendritic cell neoplasms, posttransplantation lymphoproliferative disorders, and a combination thereof. Without limitations, hematologic malignancies can be mature B-cell neoplasms, e.g., small lymphocytic lymphoma, B-cell prolymphocytic leukemia, splenic marginal zone lymphoma, hairy cell leukemia, splenic lymphoma/leukemia, lymphoplasmytic lymphoma, heavy chain diseases, plasma cell myeloma, solitary plasmacytoma of bone, extraosseous plasmacytoma, MALT lymphoma, nodal marginal zone lymphoma, follicular lymphoma, primary cutaneous follicle center lymphoma, mantle cell lymphoma, diffuse large B-cell lymphoma (DLBCL), DLBCL associated with chromic inflammation, lymphomatoid granulomatosis, primary mediastinal large B-cell lymphoma, ALK-positive large B-cell lymphoma, intravascular large B-cell lymphoma, plasmablastic lymphoma, primary effusion lymphoma, Burkitt lymphoma/leukemia, and B-cell lymphoma, mature T-cell and NK-cell neoplasms, e.g., T-cell prolymphocytic leukemia, T-cell large granular lymphocytic leukemia, chronic lymphoproliferative disorder of NK cells, aggressive NK-cell leukemia, systemic EBV-positive T-cell lymphoproliferative disease of childhood, hydroa vacciniforme-like lymphoma, adult t-cell leukemia/lymphoma, extranodal NK-T-cell lymphoma, enteropathy-associated T-cell lymphoma, hepatosplenic T-cell lymphoma, subcutaneous panniculitis-like T-cell lymphoma, mycosis fungoides, Sezary syndrome, primary cutaneous $CD30^+$ T-cell lymphoproliferative disorders, primary cutaneous $\gamma\delta$T-cell lymphoma, primary cutaneous $CD8^+$ aggressive epidermotropic cytotoxic T-cell lymphoma, primary cutaneous $CD4^+$ small/medium T-cell lymphoma, peripheral T-cell lymphoma, angioimmunoblastic T-cell lymphoma, and anaplastic large cell lymphoma, Hodgkin's lymphomas, e.g., nodular lymphocyte predominant Hodgkin lymphoma, classical Hodgkin lymphoma, nodular sclerosis classical Hodgkin lymphoma, lymphocyte-rich classical Hodgkin lymphoma, mixed cellularity classical Hodgkin lymphoma, and lymphocyte-depleted classical Hodgkin lymphoma, histiocytic and dendritic cell neoplasms, e.g., histiocytic sarcoma, Langerhans cell histiocytosis, interdigitating dendritic cell sarcoma, follicular dendritic cell sarcoma, fibroblastic reticular cell tumor, intermediate dendritic cell tumor, and disseminated juvenile xanthogranuloma, posttransplantation lymphoproliferative disorders (PTLDs), e.g., early lesions, polymorphic PTLD, monomorphic PTLD, and classical Hodgkin lymphoma type PTLD, myeloproliferative neoplasms, e.g., chronic myelogenous leukemia, chronic neutrophilic leukemia, polycythemia vera, primary myelofibrosis, essential thrombocytemia, chronic eosinophilic leukemia, mastocytosis, and unclassifiable myeloproliferative neoplasms, myeloid and lymphoid neoplasms associated with eosinophilia, e.g., myeloid and lymphoid neoplasms associated with PDGRA rearrangement, myeloid neoplasms associated with PDGRB rearrangement, and myeloid and lymphoid neoplasms associated with FGFR1 abnormalities, myelodysplastic/myeloproliferative neoplasms, e.g., chronic myelomonocytic leukemia, atypical chronic myelomonocytic leukemia, juvenile myelomonocytic leukemia, and unclassifiable myelodysplastic/myeloproliferative neoplasms, myelodysplastic syndrome (MDS), e.g., refractory cytopenia with unilineage dysplasia, refractory anemia with ring sideroblasts, refractory cytopenia with multilineage dysplasia, refractory anemia with excess blasts, myelodysplastic syndrome with isolated del(5q), unclassifiable my elodysplastic syndrome, and childhood myelodysplastic syndrome, neoplasms related to AML, e.g., therapy-related myeloid neoplasms, myeloid sarcoma, myeloid proliferations reated to Down syndrome, and blastic plasmacytoid dendritic cell neoplasm, and acute leukemias of ambiguous lineage, e.g., acute undifferentiated leukemia and mixed phenotype acute leukemias.

In certain instances, a subject having acute lymphoblastic leukemia (ALL) can have B-cell ALL (e.g., precursor B cell ALL and mature B cell ALL) or T-cell ALL (e.g., precursor T cell ALL or mature T cell ALL).

Biological samples for use in the present invention may be obtained from a variety of sources, particularly blood, plasma, or serum. In some instances, samples such as bone marrow, lymph, cerebrospinal fluid, synovial fluid, a tumor biopsy, a tissue biopsy, a fine needle aspirate, circulating tumor cells, and the like may be used. For instance, a biological sample such as a neuroblastoma cell, blood, plasma, serum, a circulating tumor cell, a bone marrow aspirate, a tissue biopsy, a tumor biopsy, or a fine needle aspirate can be obtained from a subject with neuroblastoma. Such biological samples can be processed by centrifugation, elutriation, density gradient separation, apheresis, affinity selection, panning, FACS, centrifugation with Hypaque, etc. In some embodiments, a mononuclear fraction of a bone marrow cell sample, such as peripheral blood mononuclear cells (PBMC) can be isolated.

Once a sample is obtained, it can be used directly, frozen, or maintained in appropriate culture medium for short periods of time. Various media can be employed to maintain cells. The samples may be obtained by any convenient procedure, such as the drawing of blood, venipuncture, biopsy, or the like. In some instances, the cells of a sample are maintained under conditions that do not induce proliferation or growth. For example, the cells may be maintained in a medium or buffer that lacks one or more components that are needed for cell growth.

The samples can be from human patients, although animal models may find use, e.g., equine, bovine, porcine, canine, feline, rodent, e.g., mice, rats, hamster, primate, etc. Optionally, samples can be obtained from xenograft mouse models.

The biological sample for use in the methods provided herein can be a cell culture sample. Such a sample, includes, but is not limited to, an immortalized cancer cell line, a cell line derived from cells obtained from a patient with cancer, a modified cancer cell line, a mutated cancer cell line, an in vitro culture of cell derived from a patient with cancer, and the like. The cell culture sample can be a cell line generated from a patient having any of the cancers described herein, including a hematologic malignancy. These and other cancer cell lines can be purchased from, for example, ATCC (Manassas, Va.). In some embodiments, the cell culture sample includes cancer cells that have been 1) taken from a patient with cancer, 2) xenografted into an immuno-deficient animal, and 3) harvested from the xenograft animal with cancer.

Non-limiting examples of cell culture samples include ALL cell lines (e.g., pre-B ALL cell lines, mature B ALL cell lines, pre-T ALL cell lines, and mature T ALL cell lines), AML cell lines, CML cell lines, cell lines derived from other types of leukemia, lymphoma cell lines, myeloma cell lines, neuroblastoma cell lines, glioblastoma cell lines, melanoma cell lines, breast cancer cell lines, colon cancer cell lines, pancreatic cancer cell lines, prostate cancer cell lines, and other cell lines obtained (derived) from a solid tumor cancer. Useful cell lines for ALL include Jurkat cells, Reh cells, JM1 cells, and MOLT4 cells; for AML or CML include K562 cells; and for neuroblastoma include SK-N-BE cells, SK-N-DZ cells, IRM32 cells, SK-N-SH cells, and SH-SY5Y cells. Other useful neuroblastoma cell lines include, but are not limited to, BE(2)-C, BE(2)-M17, CHP-212, IMR-32, NB-EBc1, NB-1643, LA-N-5, LA-N-6, SK-N-BE(1), SK-N-BE(2), SK-N-AS, SK-N-DZ, SK-N-FI, SK-N-MC, SK-N-RA, SK-N-SH, SMS-KCN, SMS-KCNR, SMS-KAN, SMS-KANR, CLB-BerLud1, and CLB-BerLud2. A neuroblastoma cell line can be generated from cancer cells obtained from a patient with neuroblastoma.

Standard methods for maintaining, culturing, and expanding the cell culture sample are known by those skilled in the art. See, e.g., Davis, John, ed. Animal Cell Culture. Hoboken, N.J.: Wiley-Blackwell, 2011 and Helgasonm, C. D. and Miller, C. L., eds. *Basic Cell Culture Protocols*. New York City, N.Y.: Humana Press, 2005. An appropriate solution may be used for dispersion or suspension of the cell sample. Such solution will generally be a balanced salt solution, e.g., normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

In addition, cell culture samples can be cultured in a serum-free stem cell culture medium under an adherent or floating culture condition. Alternatively, the cells can be spheroid-cultured, and then cultured in a serum-free stem cell culture medium under an adherent or floating culture condition. Alternatively, the cells can be grafted and passaged in non-human animals, and then cultured in a serum-free stem cell culture medium under an adherent or floating culture condition. For example, the cell culture sample can be grafted and passaged in an immuno-deficient animal, e.g., a NOD/SCID/IL2Rγ null (NSG) mouse, and cultured in a serum-free stem cell culture medium under an adherent or suspension culture condition in order to prepare a xenografted cancer cell line containing cancer stem cells. In some embodiments, the isolated cancer stem cells are enriched or expanded in an in vitro cell culture system or in a xenografted animal model.

B. Selecting and Isolating Cancer Stem Cells

The inventors have surprisingly discovered that cancer stem cells, including leukemia stem cells, bladder cancer stem cells, neuroblastoma stem cells, glioblastoma stem cells, melanoma stem cells, breast cancer stem cells, colon cancer stem cells, ovarian cancer stem cells, pancreatic cancer stem cells, prostate cancer stem cells, and cancer stem cells from other solid tumor cancers, can be identified in a heterogeneous population of cancer cells after the leukemic cells are incubated with a fluorescent glucose analog, e.g., 2-(N-(7-nitrobenz-2-oxa-1,3-diazol-4-yl) amino-2-deoxyglucose (2-NBDG) and the like. The cancer stem cells have a lower (reduced, decreased or diminished) level of fluorescence from a fluorescent glucose analog, e.g., 2-NBDG, compared to other cancer cells in the mixed population. In some embodiments, the level of fluorescence of a cancer stem cell from, e.g., 2-NBDG treatment is at least about 1-log, e.g., at least about 1-log, at least about 2-log, at least about 3-log, at least about 4-log, or at least about 5-log lower compared to the non-cancer stem cells in the sample. A cancer stem cell can have about 2-log lower fluorescence from, e.g., 2-NBDG than a corresponding cancer cell that is not a cancer stem cell. In some cases, the level of fluorescence (mean fluorescence intensity) from a fluorescent glucose analog is measured to be at least 10× lower in a cancer stem cell compared to a non-cancer stem cell.

In some embodiments, cancer stem cells have a higher level of 2-NBDG fluorescence compared to unstained control cells. For instance, cancer stem cells can have at least about 1-log, e.g., at least about 1-log, at least about 2-log, at least about 3-log, at least about 4-log, or at least about 5-log higher compared to unstained cancer cells, e.g., cancer cells that have not been incubated with a fluorescent glucose analog.

Other fluorescent glucose analogs that can be used in the present invention include, but are not limited to, 2-(N-(7-nitrobenz-2-oxa-1,3-diazol-4-yl)amino-2-deoxyglucose (2-NBDG; Life Technologies, Carlsbad, Calif.; Yoshioka et al., *Biochim Biophys Act*, 1996, 1289:5-9), 6-deoxy-N-(7-nitrobenz-2-oxa-1,3-diazol-4-yl)aminoglucose (6-NBDG; Life Technologies; Speizer et al., *Biochim Biophys Act*, 1985, 815:75-84); pyropheophorbide 2-deoxyglucoseamide (pyro-2DG; Cheng et al., *Bioconjug Chem*, 2006, 17:662-669), Cy5.5-D-glucosamine (Cy5.5-2DG; Zhang et al., *Bioconjug Chem*, 2003, 14:709-714), Cy3-linked O-1-glycosylated glucose (Cy3-α-glucose and Cy3-β-glucose; U.S. Pat. No. 8,679,854; Park et al., *Angew Chem Int Ed Engl*, 2007, 46:2018-2022), IRDye 800CW 2-DG (LI-COR Biosciences, Lincoln, Nebr.); CyNE 2-DG (Vendrell et al., *Org Biomol Chem*, 2011, 9:4760-4762), GB3-Cy3 (Lee et al., *Chemistry*, 2011, 17:413-450), two-photon glucose analogs (AG1 and AG2; Tian et al., *Angew Chem Int Ed Engl*, 2009, 48:8027-8031), pyrindine 4,7-diphenyl-1,10-phenanthroline ($Ph_2$-phen)rhenium(I) polypyridine glucose complex (Wani et al., *J Am Chem Soc*, 1971, 93:2325-2327), 4,4',4"-tris(4-(2-(4-(benzo-[d]triazol-2-yl)phenyl)-9-9'-bis(6-thiol-β-D-glucose)-hexyl)-fluoren-7-yl)phenylamine (TFBS; Wang et al., *Chem Mater*, 2011, 23:4428-4434), analogs thereof, and derivatives thereof. Additional useful fluorescent-tagged glucose analogs are described in, e.g., Kim et al., *Sensors*, 2012, 12:5005-5027.

In some embodiments, the biological sample or cell culture sample is treated or incubated with a fluorescent glucose analog in vivo or ex vivo. In some embodiments of ex vivo treatment, the fluorescent glucose analog is added to the sample at a concentration of about 0.1 µM to about 100 µM, e.g., about 0.1 µM to 50 µM, about 50 µM to 100 µM, 0.1 µM to 25 µM, 0.1 µM to 10 µM, 1 µM to 100 µM, 1 µM to 50 µM, 25 µM to 75 µM, 50 µM to 75 µM, or 75 µM to 100 µM. In some instances, the sample is incubated with the fluorescent glucose analog for at least 15 minutes, e.g., at least 15 minutes, 20 minutes, 30 minutes, 40 minutes, 50 minutes, 60 minutes or more, at room temperature or at 21°-37° C. In some cases, an effective amount of fluorescent glucose analog is incubated with the sample at a specific temperature for a specific amount of time in order for a cell (e.g., a non-cancer stem cell) of the sample to take up or internalize the analog.

In some embodiments, the biological sample obtained from a subject is not cultured or expanded before incubating the sample with a fluorescent glucose analog. For instance, the cells of the biological sample are maintained in a culture medium or buffer that does not promote or initiate cell growth or proliferation. The culture medium or buffer can retain or conserve the viability of the cells. The biological sample can be maintained in a culture medium that is free of glucose.

In some embodiments, the biological sample or cell culture sample is also stained with a fluorescent antibody that binds to an antigen on the cells and/or another fluorescent stain, such as 4',6-diamidino-2-phenylindole (DAPI). In some embodiments, the fluorescent antibody is an anti-human leukocyte antigen (HLA) antibody labeled with a fluorochrome, e.g., allophycocyanin (APC).

The cancer stem cells, such as 2-NBDG low fluorescing cancer cells, can be identified in a heterogeneous population of cancer cells using standard methods known to those skilled in the art, such as flow cytometry, immunocytochemistry, fluorescence microscopy, whole animal imaging, and the like. For instance, any method for detecting the presence of a fluorescent cell in vitro or in vivo may be used in the present invention. In some embodiments, the level of fluorescence is measured using flow cytometry.

The cancer stem cells can be isolated from a sample using standard methods known to those in the art, such as cell sorting. Non-limiting examples of cell sorting include fluorescence-activated cell sorting (FACS), single cell sorting, for example, based on intracellular and extracellular properties, and magnetic cell sorting, such as MACS (Meltenyi Biotec), Dynabeads (Life Technologies, Carlsbad, Calif.), BD IMag™ (BD Biosciences, San Jose, Calif.) and the EasySep™ (StemCell Technologies, Vancouver, BC). In some embodiments, the method of isolating cancer stem cell including leukemia stem cells from a patient-derived sample or a cell line sample includes FACS.

The isolated cancer stem cells may be collected in any appropriate medium that maintains the viability of the cells, usually medium containing serum. Various media are commercially available and may be used according to the nature of the cells, including DMEM, HBSS, DPBS, RPMI, Iscove's medium, etc., frequently supplemented with fetal calf serum.

C. Detecting Cancer Stem Cell Markers

The present invention also relates to determining the expression level of one or more cancer stem cell markers in a selected cancer stem cell. Thus, RNA or protein may be extracted from the cancer stem cell. Methods for extracting nucleic acids, e.g., RNA are well known to those skilled in the art. General methods of RNA isolation and protein extraction (e.g., described by Sambrook and Russell, ed. *Molecular Cloning: A Laboratory Manual* 3d, 2001 and Ausubel et al., eds. *Current Protocols in Molecular Biology*, 1994) can be followed. Various commercially available reagents or kits, such as Trizol® reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain RNA from a cell. PCR reagents and protocols are also available from commercial vendors, such as Roche Molecular Systems, Life Technologies, Bio-Rad, and the like.

In some embodiments, the expression levels of RNA, or amplified or cloned versions thereof, are determined by a hybridization-based assay, such as, but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987. Non-limiting examples of a hybridization assay include Northern blotting, in situ hybridization, microarray, In some embodiments, the expression levels of mRNA are determined by a PCR-based method or variations thereof, such as, but not limited to, quantitative PCR, reverse transcription PCR (RT-PCR), real-time PCR, and quantitative reverse transcription PCR (qRT-PCR). The general methods of PCR and variants thereof are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990.

Prior to the amplification step, a DNA copy (cDNA) of the RNA transcript of interest must be synthesized. This can be performed by reverse transcription, which can be carried out as a separate step, or in a homogeneous reverse transcription-polymerase chain reaction (RT-PCR), a modification of the PCR for amplifying RNA. Methods suitable for PCR amplification of RNA are described by Romero and Rotbart in *Diagnostic Molecular Biology: Principles and Applications*, pp. 401-406; Persing et al., eds., Mayo Foundation, Rochester, Minn., 1993; Egger et al., *J. Clin. Microbiol.*, 1995, 33:1442-1447; and U.S. Pat. No. 5,075,212

In other embodiments, the expression level of a cancer stem cell marker, e.g., a leukemia stem cell marker, can be determined by analyzing protein expression. Useful methods include, but are not limited to, SDS-PAGE, western blotting, immunocytochemistry, an enzyme linked immunosorbent assay (ELISA), mass spectroscopy, immune-PCR, FACS and protein microarrays.

In some embodiments, the expression level of one or more leukemia stem cell markers described herein is determined using a single-cell gene expression method. Useful examples of such technology include Fluidigm's single-cell gene expression system (e.g., C1™ Single-Cell Auto Prep System and BioMark™ HD System), nCounter® Single Cell Gene Expression Array (NanoString, Seattle, Wash.), and Life Technologies' Single Cell Analysis workflow (e.g., Ambion® Single Cell-to-CT™ kit and TaqMan® Assays).

In some embodiments, the methods provided herein include measuring or detecting the expression level of at least one leukemia stem cell marker of Table 1, e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, or 121 leukemia stem cell markers of Table 1 in a cell (e.g., a test cell). In other words, the methods include measuring the expression level of 1 to 121 different leukemia stem cell markers set forth in Table 1 including housekeeping genes and long intergenic non-coding RNAs (lincRNAs) in a cell. In some embodiments, the cell has a low level of 2-NBDG fluorescence compared to a differentiated cancer cell. In other embodiments, the cell is suspected of being a cancer stem cell, e.g., a leukemia stem cell.

In some embodiments, the expression level of the leukemia stem cell marker No. 1, No. 2, No. 3, No. 4, No. 5, No. 6, No. 7, No. 8, No. 9, No. 10, No. 11, No. 12, No. 13, No. 14, No. 15, No. 16, No. 17, No. 18, No. 19, No. 20, No. 21, No. 22, No. 23, No. 24, No. 25, No. 26, No. 27, No. 28, No. 29, No. 30, 31, No. 32, No. 33, No. 34, No. 35, No. 36, No. 37, No. 38, No. 39, No. 40, No. 41, No. 42, No. 43, No. 44, No. 45, No. 46, No. 47, No. 48, No. 49, No. 50, No. 51, No. 52, No. 53, No. 54, No. 55, No. 56, No. 57, No. 58, No. 59, No. 60, No. 61, No. 62, No. 63, No. 64, No. 65, No. 66, No. 67, No. 68, No. 69, No. 70, No. 71, No. 72, No. 73, No. 74, No. 75, No. 76, No. 77, No. 78, No. 79, No. 80, No. 81, No. 82, No. 83, No. 84, No. 85, No. 86, No. 87, No. 88, No. 89, No. 90, No. 91, No. 92, No. 93, No. 94, No. 95, No. 96, No. 97, No. 98, No. 99, No. 100, No. 101, No. 102, No. 103, No. 104, No. 105, No. 106, No. 107, No. 108, No. 109, No. 110, No. 111, No. 112, No. 113, No. 114, No. 115, No. 116, No. 117, No. 118, No. 119, No. 120, or No. 121 of Table 1, or any combination thereof is measured in a cell (e.g., a test cell) from a sample comprising leukemia stem cells and non-leukemia stem cells.

TABLE 1

121 Leukemia Stem Cell Markers

| No. | Leukemia stem cell marker (gene or lincRNA) | NCBI Ref. Seq. No. or Other Ref. No. | Full Name |
| --- | --- | --- | --- |
| 1 | AACS | NM_023928 | acetoacetyl-CoA synthetase |
| 2 | ANGPTL2 | NM_012098.2 | angiopoietin-like 2 |
| 3 | ARHGAP23 | NM_001199417 | Rho GTPase activating protein 23 |
| 4 | ATP2A3 | NM_174953.1\| NM_174954.1\| NM_174955.1\| NM_174956.1\| NM_174958.1\| NM_174957.1\| NM_005173.2 | ATPase, $Ca^{++}$ transporting, ubiquitous |
| 5 | ATP6V1C2 | NM_144583.3\| NM_001039362.1 | ATPase, H+ transporting, lysosomal 42 kDa, V1 subunit C2 |
| 6 | ATPAF1 | NM_001042546\| NM_022745\| NM_001243728\| NM_001256418 | ATP synthase mitochondrial F1 complex assembly factor 1 |
| 7 | C21orf128 | NR_027243 | chromosome 21 open reading frame 128 |
| 8 | C2CD3 | NM_015531.4 | C2 calcium-dependent domain containing 3 |
| 9 | C5orf58 | NM_001102609.1 | chromosome 5 open reading frame 58 |
| 10 | CD3G | NM_000073 | CD3g molecule, gamma (CD3-TCR complex) |
| 11 | CD58 | NR_026665.1\| NM_001779.2\| NM_001144822.1 | CD58 molecule |
| 12 | CDKN2A | NM_058197\| NM_058195\| NM_000077\| NM_001195132 | cyclin-dependent kinase inhibitor 2A |
| 13 | COX6A1 | NM_004373 | cytochrome c oxidase subunit VIa polypeptide 1 |
| 14 | COX7A2 | NR_029466.1\| NM_001865.3 | cytochrome c oxidase subunit VIIa polypeptide 2 (liver) |
| 15 | CRAT | NM_001257363\| NM_000755 | carnitine O-acetyltransferase |
| 16 | CTSZ | NM_001336.3 | cathepsin Z |
| 17 | CYB5RL | NM_001031672.2 | cytochrome b5 reductase-like |
| 18 | DDX11 | NM_004399\| NM_001257144\| NM_152438\| NM_030653\| NM_001257145 | DEAD/H (Asp-Glu-Ala-Asp/His) box helicase 11 |
| 19 | ELMO2 | NM_133171.3\| NM_182764.1 | engulfment and cell motility 2 |

TABLE 1-continued

121 Leukemia Stem Cell Markers

Figure 4A:
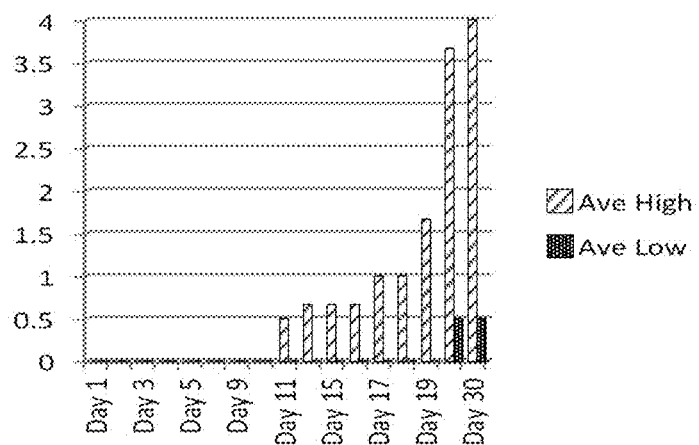
FIGS. 4A-C show that leukemia stem cells with low NBDG fluorescence were isolated from the Molt4 cell line of T cells from an acute lymphoblastic leukemia (ALL) patient. These cells formed fewer colonies in an in vitro colony forming assay (FIG. 4A), have lower HLA expression compared to NBDG high Molt4 cells (FIG. 4B) and are smaller in size as illustrated by phase contrast microscopy (FIG. 4C).
Figure 4B:
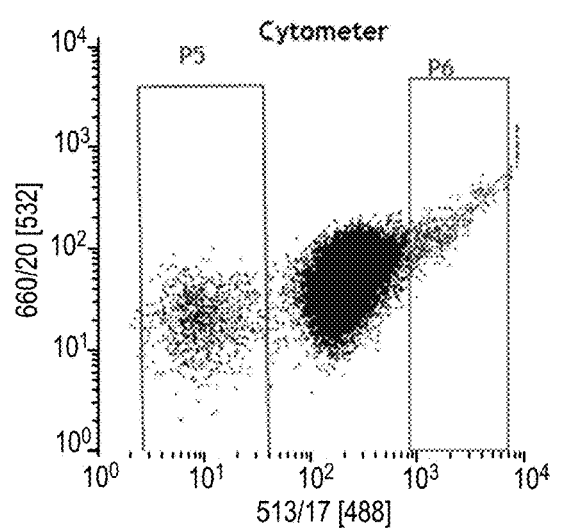
Figure 4C:
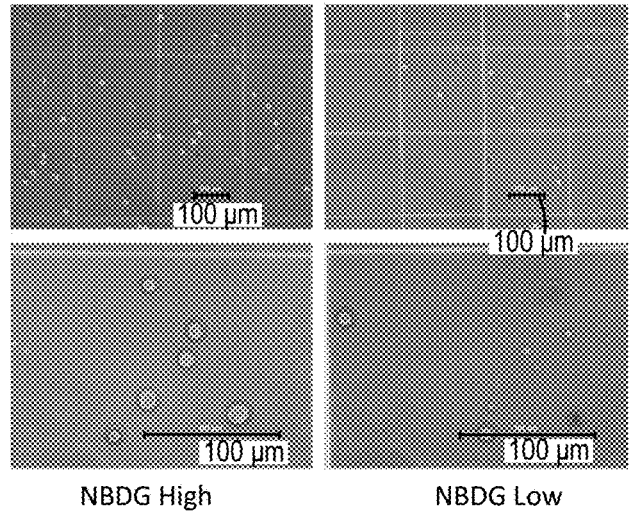

| No. | Leukemia stem cell marker (gene or lincRNA) | NCBI Ref. Seq. No. or Other Ref. No. | Full Name |
|---|---|---|---|
| 20 | ERVMER34-1 | NM_024534\| NM_001242690 | endogenous retrovirus group MER34, member 1 |
| 21 | EXOC2 | NM_018303.4 | exocyst complex component 2 |
| 22 | FAM53C | NM_016605.2\| NM_001135647.1 | family with sequence similarity 53, member C |
| 23 | FCRL5 | NM_001195388\| NM_031281 | Fc receptor-like 5 |
| 24 | FIG4 | NM_014845.5 | FIG4 homolog, SAC1 lipid phosphatase domain containing (S. cerevisiae) |
| 25 | FKBP2 | NM_001135208.1\| NM_057092.2\| NM_004470.3 | FK506 binding protein 2, 13 kDa |
| 26 | FLJ13224 | NR_026806 | uncharacterized LOC79857 |
| 27 | FMR1NB | NM_152578.2 | fragile X mental retardation 1 neighbor |
| 28 | GLA | NM_000169.2 | galactosidase, alpha |
| 29 | HIF3A | NM_152796\| NM_152794\| NM_022462\| NM_152795 | hypoxia inducible factor 3, alpha subunit |
| 30 | HIST1H2AC | NM_003512.3 | histone cluster 1, H2ac |
| 31 | HIST1H3H | NM_003536.2 | histone cluster 1, H3h |
| 32 | HIST3H2A | NM_033445 | histone cluster 3, H2a |
| 33 | HIST4H4 | NM_175054.2 | histone cluster 4, H4 |
| 34 | HLA-A | NM_002116 | major histocompatibility complex, class I, A |
| 35 | HMMR | NM_012485.2\| NM_012484.2\| NM_001142557.1\| NM_001142556.1 | hyaluronan-mediated motility receptor (RHAMM) |
| 36 | IL4 | NM_172348.1\| NM_000589.2 | interleukin 4 |
| 37 | KAZALD1 | NM_030929.4 | Kazal-type serine peptidase inhibitor domain 1 |
| 38 | KRTAP3-3 | NM_033185 | keratin associated protein 3-3 |
| 39 | KRTAP4-11 | NM_033059 | keratin associated protein 4-11 |
| 40 | LOC100130539 | NM_001258000 | uncharacterized LOC100130539 |
| 41 | LOC440900 | NR_034128 | |
| 42 | LOC644656 | NR_036539 | uncharacterized LOC644656 |
| 43 | LRRC2 | NM_024512.3 | leucine rich repeat containing 2 |
| 44 | LY96 | NM_015364\| NM_001195797 | lymphocyte antigen 96 |
| 45 | MALAT1 | NR_002819 | metastasis associated lung adenocarcinoma transcript 1 (non-protein coding) |
| 46 | MIR17HG | NR_027350\| NR_027349 | miR-17-92 cluster host gene (non-protein coding) |
| 47 | MTPN | NM_145808\| NM_001128619 | myotrophin |
| 48 | NDUFB9 | NM_005005.2 | NADH dehydrogenase (ubiquinone) 1 beta subcomplex, 9, 22 kDa |
| 49 | NUPL1 | NM_014089.3\| NM_001008564.1 | nucleoporin like 1 |
| 50 | ODF3L2 | NM_182577.2 | outer dense fiber of sperm tails 3-like 2 |
| 51 | OR5L2 | NM_001004739.1 | olfactory receptor, family 5, subfamily L, member 2 |
| 52 | ORMDL2 | NM_014182 | ORM1-like 2 (S. cerevisiae) |
| 53 | P2RX3 | NM_002559.2 | purinergic receptor P2X, ligand-gated ion channel, 3 |
| 54 | PFN1P2 | NR_003242 | profilin 1 pseudogene 2 |
| 55 | PLEKHG6 | NM_001144857.1\| NM_001144856.1\| NM_018173.3 | pleckstrin homology domain containing, family G (with RhoGef domain) member 6 |
| 56 | POLE | NM_006231 | polymerase (DNA directed), epsilon, catalytic subunit |
| 57 | RAI1 | NM_030665.3 | retinoic acid induced 1 |
| 58 | RBM23 | NM_018107\| NM_001077352\| NM_001077351 | RNA binding motif protein 23 |
| 59 | REEP4 | NM_025232.2 | receptor accessory protein 4 |
| 60 | RELL1 | NM_001085400.1\| NM_001085399.1 | RELT-like 1 |
| 61 | RIMS3 | NM_014747.2 | regulating synaptic membrane exocytosis 3 |
| 62 | NAPSA | NM_004851.1 | napsin A aspartic peptidase |
| 63 | PIGL | NM_004278.3 | phosphatidylinositol glycan anchor biosynthesis, class L |
| 64 | RNASE13 | NM_001012264.3 | ribonuclease, RNase A family, 13 (non-active) |
| 65 | RNU12 | NR_029422 | RNA, U12 small nuclear |
| 66 | RNU4ATAC | NR_023343 | RNA, U4atac small nuclear (U12-dependent splicing) |
| 67 | RPS27 | NM_001030 | ribosomal protein S27 |
| 68 | SCARNA2 | NR_003023 | small Cajal body-specific RNA 2 |
| 69 | SCARNA5 | NR_003008 | small Cajal body-specific RNA 5 |
| 70 | SCARNA7 | NR_003001 | small Cajal body-specific RNA 7 |

TABLE 1-continued

121 Leukemia Stem Cell Markers

| No. | Leukemia stem cell marker (gene or lincRNA) | NCBI Ref. Seq. No. or Other Ref. No. | Full Name |
|---|---|---|---|
| 71 | SEC16A | NM_014866.1 | SEC16 homolog A (S. cerevisiae) |
| 72 | SFT2D2 | NM_199344.2 | SFT2 domain containing 2 |
| 73 | SMAD2 | NM_001135937.1\| NM_001003652.2\| NM_005901.4 | SMAD family member 2 |
| 74 | SNORA12 | NR_002954 | small nucleolar RNA, H/ACA box 12 |
| 75 | SNORA26 | NR_003016 | small nucleolar RNA, H/ACA box 26 |
| 76 | SNORA53 | NR_003015 | small nucleolar RNA, H/ACA box 53 |
| 77 | SNORA74A | NR_002915 | small nucleolar RNA, H/ACA box 74A |
| 78 | SNORA81 | | small nucleolar RNA, H/ACA box 81 |
| 79 | SON | NM_138927.1\| NM_032195.1 | SON DNA binding protein |
| 80 | SPATA21 | NM_198546.1 | spermatogenesis associated 21 |
| 81 | TBC1D10B | NM_015527 | TBC1 domain family, member 10B |
| 82 | TBL1XR1 | NM_024665 | transducin (beta)-like 1 X-linked receptor 1 |
| 83 | TBXAS1 | NM_030984\| NM_001166254\| NR_029394\| NM_001061\| NM_001130966\| NM_001166253 | thromboxane A synthase 1 (platelet) |
| 84 | TDG | NM_003211 | thymine-DNA glycosylase |
| 85 | TNIK | NM_001161563\| NM_001161564\| NM_015028\| NM_001161560\| NM_001161565\| NM_001161566\| NM_001161561\| NM_001161562 | TRAF2 and NCK interacting kinase |
| 86 | TP53INP2 | NM_021202 | tumor protein p53 inducible nuclear protein 2 |
| 87 | UBAP2 | NM_018449.2 | ubiquitin associated protein 2 |
| 88 | ZNF28 | NM_006969.3 | zinc finger protein 28 |
| 89 | ACTB | NM_001101 | actin, beta |
| 90 | B2M | NM_004048 | beta-2-microglobulin |
| 91 | GAPDH | NM_002046\| NM_001256799 | glyceraldehyde-3-phosphate dehydrogenase |
| 92 | HSP90AB1 | NM_007355 | heat shock protein 90 kDa alpha (cytosolic), class B member 1 |
| 93 | TFRC | NM_001128148.1 | transferrin receptor |
| 94 | lincRNA_chr4_53578686_53579392_fs | FLDM-001190.1 | |
| 95 | lincRNA_chr15_25332807_25334252_fs | FLDM-011186.1 | |
| 96 | lincRNA_chr1_181309852_fs | FLDM-016084.1 | |
| 97 | lincRNA_chrX_135943809_fs | FLDM-019205.1 | |
| 98 | lincRNA_chr4_93175777_fs | FLDM-022186.1 | |
| 99 | lincRNA_chr8_96297524_rs | FLDM-024342.1 | |
| 100 | lincRNA_chr5_124738151_fs | FLDM-027364.1 | |
| 101 | lincRNA_chr14_58744247_fs | FLDM-027392.1 | |
| 102 | lincRNA_chr6_86387044_86387458_rs | FLDM-027788.1 | |
| 103 | lincRNA_chr4_53578995_53580281_rs | FLDM-031124.1 | |
| 104 | lincRNA_chr11_39499974_fs | FLDM-034475.1 | |
| 105 | lincRNA_chr20_37049663_fs | FLDM-034919.1 | |
| 106 | lincRNA_chr8_95986835_rs | FLDM-035148.1 | |
| 107 | lincRNA_chrX_71228400_fs | FLDM-035295.1 | |
| 108 | lincRNA_chr1_247354094_fs | FLDM-045403.1 | |
| 109 | lincRNA_chr4_76460401_rs | FLDM-046986.1 | |
| 110 | lincRNA_chr21_39495505_rs | FLDM-053935.1 | |
| 111 | lincRNA_chr5_167692897_fs | FLDM-057291.1 | |

TABLE 1-continued

121 Leukemia Stem Cell Markers

| No. | Leukemia stem cell marker (gene or lincRNA) | NCBI Ref. Seq. No. or Other Ref. No. | Full Name |
|---|---|---|---|
| 112 | lincRNA_chr5_4301 1418_fs | FLDM-069219.1 | |
| 113 | lincRNA_chr21_447 80472_fs | FLDM-072295.1 | |
| 114 | lincRNA_chr12_537 7839_rs | FLDM-076543.1 | |
| 115 | lincRNA_chr4_7437 5927_rs | FLDM-081164.1 | |
| 116 | lincRNA_chr8_3277 2708_fs | FLDM-083295.1 | |
| 117 | lincRNA_chr9_2535 653_fs | FLDM-083903.1 | |
| 118 | lincRNA_chr9_2683 000_fs | FLDM-084763.1 | |
| 119 | lincRNA_chrX_711 32475_rs | FLDM-089529.1 | |
| 120 | lincRNA_chr15_585 06416_rs | FLDM-093281.1 | |
| 121 | lincRNA_chr10_134 136360_fs | FLDM-094803.1 | |

In some embodiments, the methods provided herein include measuring or detecting the expression level of at least one leukemia stem cell marker of Table 2, e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, or 93 leukemia stem cell markers of Table 2. For instance, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, or all of the leukemia stem cell markers of Table 2 including the housekeeping genes and lincRNAs are measured in a cell.

In some embodiments, the expression level of the leukemia stem cell marker No. 1, No. 2, No. 3, No. 4, No. 5, No. 6, No. 7, No. 8, No. 9, No. 10, No. 11, No. 12, No. 13, No. 14, No. 15, No. 16, No. 17, No. 18, No. 19, No. 20, No. 21, No. 22, No. 23, No. 24, No. 25, No. 26, No. 27, No. 28, No. 29, No. 30, 31, No. 32, No. 33, No. 34, No. 35, No. 36, No. 37, No. 38, No. 39, No. 40, No. 41, No. 42, No. 43, No. 44, No. 45, No. 46, No. 47, No. 48, No. 49, No. 50, No. 51, No. 52, No. 53, No. 54, No. 55, No. 56, No. 57, No. 58, No. 59, No. 60, No. 61, No. 62, No. 63, No. 64, No. 65, No. 66, No. 67, No. 68, No. 69, No. 70, No. 71, No. 72, No. 73, No. 74, No. 75, No. 76, No. 77, No. 78, No. 79, No. 80, No. 81, No. 82, No. 83, No. 84, No. 85, No. 86, No. 87, No. 88, No. 89, No. 90, No. 91, No. 92, or No. 93 of Table 2, or any combination of the markers in Table 2, is measured in a cell (e.g., a test cell) from a sample comprising leukemia stem cells and non-leukemia stem cells.

In some embodiments, the expression level of one or more human large intergenic non-coding RNAs (lincRNAs) of Table 2, e.g., 1, 2, 3, 4, 5, 6, 7, 8, 9, 10, 11, 12, 13, 14, 15, 16, 17, 18, 19, 20, 21, 22, 23, 24, 25, 26, 27 or 28 are determined in the sample. In some instances, the expression level of the lincRNA No. 1, 2, 3, 4, 5, 6, 7, 8, 9, 10, 11, 12, 13, 14, 15, 16, 17, 18, 19, 20, 21, 22, 23, 24, 25, 26, 27 or 28 of Table 2, or any combination thereof is measured in a cell from the sample that includes leukemia stem cells and non-leukemia stem cells.

TABLE 2

93 Leukemia Stem Cell Markers

| No. | Leukemia stem cell marker (gene or lincRNA) | NCBI Ref. Seq. No. or Other Ref. No. | Full Name |
|---|---|---|---|
| 1 | AACS | NM_023928 | acetoacetyl-CoA synthetase |
| 2 | ANGPTL2 | NM_012098.2 | angiopoietin-like 2 |
| 3 | ARHGAP23 | NM_001199417 | Rho GTPase activating protein 23 |
| 4 | ATP2A3 | NM_174953.1\| NM_174954.1\| NM_174955.1\| NM_174956.1\| NM_174958.1\| NM_174957.1\| NM_005173.2 | ATPase, $Ca^{++}$ transporting, ubiquitous |
| 5 | ATP6V1C2 | NM_144583.3\| NM_001039362.1 | ATPase, H+ transporting, lysosomal 42 kDa, V1 subunit C2 |
| 6 | ATPAF1 | NM_001042546\| NM_022745\| NM_001243728\| NM_001256418 | ATP synthase mitochondrial F1 complex assembly factor 1 |
| 7 | C21orf128 | NR_027243 | chromosome 21 open reading frame 128 |
| 8 | C2CD3 | NM_015531.4 | C2 calcium-dependent domain containing 3 |

TABLE 2-continued

93 Leukemia Stem Cell Markers

| No. | Leukemia stem cell marker (gene or lincRNA) | NCBI Ref. Seq. No. or Other Ref. No. | Full Name |
|---|---|---|---|
| 9 | C5orf58 | NM_001102609.1 | chromosome 5 open reading frame 58 |
| 10 | CD3G | NM_000073 | CD3g molecule, gamma (CD3-TCR complex) |
| 11 | CD58 | NR_026665.1\| NM_001779.2\| NM_001144822.1 | CD58 molecule |
| 12 | CDKN2A | NM_058197\| NM_058195\| NM_000077\| NM_001195132 | cyclin-dependent kinase inhibitor 2A |
| 13 | COX6A1 | NM_004373 | cytochrome c oxidase subunit VIa polypeptide 1 |
| 14 | COX7A2 | NR_029466.1\| NM_001865.3 | cytochrome c oxidase subunit VIIa polypeptide 2 (liver) |
| 15 | CRAT | NM_001257363\| NM_000755 | carnitine O-acetyltransferase |
| 16 | CTSZ | NM_001336.3 | cathepsin Z |
| 17 | CYB5RL | NM_001031672.2 | cytochrome b5 reductase-like |
| 18 | DDX11 | NM_004399\| NM_001257144\| NM_152438\| NM_030653\| NM_001257145 | DEAD/H (Asp-Glu-Ala-Asp/His) box helicase 11 |
| 19 | ELMO2 | NM_133171.3\| NM_182764.1 | engulfment and cell motility 2 |
| 20 | ERVMER34-1 | NM_024534\| NM_001242690 | endogenous retrovirus group MER34, member 1 |
| 21 | EXOC2 | NM_018303.4 | exocyst complex component 2 |
| 22 | FAM53C | NM_016605.2\| NM_001135647.1 | family with sequence similarity 53, member C |
| 23 | FCRL5 | NM_001195388\| NM_031281 | Fc receptor-like 5 |
| 24 | FIG4 | NM_014845.5 | FIG4 homolog, SAC1 lipid phosphatase domain containing (S. cerevisiae) |
| 25 | FKBP2 | NM_001135208.1\| NM_057092.2\| NM_004470.3 | FK506 binding protein 2, 13 kDa |
| 26 | FLJ13224 | NR_026806 | uncharacterized LOC79857 |
| 27 | FMR1NB | NM_152578.2 | fragile X mental retardation 1 neighbor |
| 28 | GLA | NM_000169.2 | galactosidase, alpha |
| 29 | HIF3A | NM_152796\| NM_152794\| NM_022462\| NM_152795 | hypoxia inducible factor 3, alpha subunit |
| 30 | HIST1H2AC | NM_003512.3 | histone cluster 1, H2ac |
| 31 | HIST1H3H | NM_003536.2 | histone cluster 1, H3h |
| 32 | HIST3H2A | NM_033445 | histone cluster 3, H2a |
| 33 | HIST4H4 | NM_175054.2 | histone cluster 4, H4 |
| 34 | HLA-A | NM_002116 | major histocompatibility complex, class I, A |
| 35 | HMMR | NM_012485.2\| NM_012484.2\| NM_001142557.1\| NM_001142556.1 | hyaluronan-mediated motility receptor (RHAMM) |
| 36 | IL4 | NM_172348.1\| NM_000589.2 | interleukin 4 |
| 37 | KAZALD1 | NM_030929.4 | Kazal-type serine peptidase inhibitor domain 1 |
| 38 | KRTAP3-3 | NM_033185 | keratin associated protein 3-3 |
| 39 | KRTAP4-11 | NM_033059 | keratin associated protein 4-11 |
| 40 | LOC100130539 | NM_001258000 | uncharacterized LOC100130539 |
| 41 | LOC440900 | NR_034128 | |
| 42 | LOC644656 | NR_036539 | uncharacterized LOC644656 |
| 43 | LRRC2 | NM_024512.3 | leucine rich repeat containing 2 |
| 44 | LY96 | NM_015364\| NM_001195797 | lymphocyte antigen 96 |
| 45 | MALAT1 | NR_002819 | metastasis associated lung adenocarcinoma transcript 1 (non-protein coding) |
| 46 | MIR17HG | NR_027350\| NR_027349 | miR-17-92 cluster host gene (non-protein coding) |
| 47 | MTPN | NM_145808\| NM_001128619 | myotrophin |
| 48 | NDUFB9 | NM_005005.2 | NADH dehydrogenase (ubiquinone) 1 beta subcomplex, 9, 22 kDa |
| 49 | NUPL1 | NM_014089.3\| NM_001008564.1 | nucleoporin like 1 |
| 50 | ODF3L2 | NM_182577.2 | outer dense fiber of sperm tails 3-like 2 |
| 51 | OR5L2 | NM_001004739.1 | olfactory receptor, family 5, subfamily L, member 2 |
| 52 | ORMDL2 | NM_014182 | ORM1-like 2 (S. cerevisiae) |
| 53 | P2RX3 | NM_002559.2 | purinergic receptor P2X, ligand-gated ion channel, 3 |
| 54 | PFN1P2 | NR_003242 | profilin 1 pseudogene 2 |
| 55 | PLEKHG6 | NM_001144857.1\| NM_001144856.1\| NM_018173.3 | pleckstrin homology domain containing, family G (with RhoGef domain) member 6 |

TABLE 2-continued

93 Leukemia Stem Cell Markers

| No. | Leukemia stem cell marker (gene or lincRNA) | NCBI Ref. Seq. No. or Other Ref. No. | Full Name |
|---|---|---|---|
| 56 | POLE | NM_006231 | polymerase (DNA directed), epsilon, catalytic subunit |
| 57 | RAI1 | NM_030665.3 | retinoic acid induced 1 |
| 58 | RBM23 | NM_018107| NM_001077352| NM_001077351 | RNA binding motif protein 23 |
| 59 | REEP4 | NM_025232.2 | receptor accessory protein 4 |
| 60 | RELL1 | NM_001085400.1| NM_001085399.1 | RELT-like 1 |
| 61 | RIMS3 | NM_014747.2 | regulating synaptic membrane exocytosis 3 |
| 62 | ACTB | NM_001101 | actin, beta |
| 63 | B2M | NM_004048 | beta-2-microglobulin |
| 64 | GAPDH | NM_002046| NM_001256799 | glyceraldehyde-3-phosphate dehydrogenase |
| 65 | HSP90AB1 | NM_007355 | heat shock protein 90 kDa alpha (cytosolic), class B member 1 |
| 66 | lincRNA_chr4_53578686_53579392_fs | FLDM-001190.1 | |
| 67 | lincRNA_chr15_25332807_25334252_fs | FLDM-011186.1 | |
| 68 | lincRNA_chr1_181309852_fs | FLDM-016084.1 | |
| 69 | lincRNA_chrX_135943809_fs | FLDM-019205.1 | |
| 70 | lincRNA_chr4_93175777_fs | FLDM-022186.1 | |
| 71 | lincRNA_chr8_96297524_rs | FLDM-024342.1 | |
| 72 | lincRNA_chr5_124738151_fs | FLDM-027364.1 | |
| 73 | lincRNA_chr14_58744247_fs | FLDM-027392.1 | |
| 74 | lincRNA_chr6_86387044_86387458_rs | FLDM-027788.1 | |
| 75 | lincRNA_chr4_53578995_53580281_rs | FLDM-031124.1 | |
| 76 | lincRNA_chr11_39499974_fs | FLDM-034475.1 | |
| 77 | lincRNA_chr20_37049663_fs | FLDM-034919.1 | |
| 78 | lincRNA_chr8_95986835_rs | FLDM-035148.1 | |
| 79 | lincRNA_chrX_71228400_fs | FLDM-035295.1 | |
| 80 | lincRNA_chr1_247354094_fs | FLDM-045403.1 | |
| 81 | lincRNA_chr4_76460401_rs | FLDM-046986.1 | |
| 82 | lincRNA_chr21_39495505_rs | FLDM-053935.1 | |
| 83 | lincRNA_chr5_167692897_fs | FLDM-057291.1 | |
| 84 | lincRNA_chr5_43011418_fs | FLDM-069219.1 | |
| 85 | lincRNA_chr21_44780472_fs | FLDM-072295.1 | |
| 86 | lincRNA_chr12_5377839_rs | FLDM-076543.1 | |
| 87 | lincRNA_chr4_74375927_rs | FLDM-081164.1 | |
| 88 | lincRNA_chr8_32772708_fs | FLDM-083295.1 | |
| 89 | lincRNA_chr9_2535653_fs | FLDM-083903.1 | |
| 90 | lincRNA_chr9_2683000_fs | FLDM-084763.1 | |
| 91 | lincRNA_chrX_71132475_rs | FLDM-089529.1 | |
| 92 | lincRNA_chr15_58506416_rs | FLDM-093281.1 | |
| 93 | lincRNA_chr10_134136360_fs | FLDM-094803.1 | |

The leukemia stem cell can be a cancer stem cell of early pre-B-cell ALL, common ALL, pre-B-cell ALL, or mature B-cell ALL (Burkitt leukemia). In other cases, the leukemia stem cell can be a cancer stem cell of pre-T-cell ALL or mature T-cell ALL.

In some embodiments, the methods provided herein include measuring or detecting the expression level of at least one leukemia stem cell marker of Table 3, e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 leukemia stem cell markers of Table 3 in a cell (e.g., a test cell). In other words, the methods include measuring the expression level of 1 to 80 different leukemia stem cell markers set forth in Table 3. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 of the leukemia stem cell markers of Table 3 are measured in the cell. In some embodiments, the cell also has a low level of 2-NBDG fluorescence compared to a differentiated cancer cell. In other embodiments, the cell is suspected of being a leukemia stem cell, e.g., a B-cell acute lymphocytic leukemia stem cell.

In some embodiments, the expression level of the leukemia stem cell marker No. 1, No. 2, No. 3, No. 4, No. 5, No. 6, No. 7, No. 8, No. 9, No. 10, No. 11, No. 12, No. 13, No. 14, No. 15, No. 16, No. 17, No. 18, No. 19, No. 20, No. 21, No. 22, No. 23, No. 24, No. 25, No. 26, No. 27, No. 28, No. 29, No. 30, 31, No. 32, No. 33, No. 34, No. 35, No. 36, No. 37, No. 38, No. 39, No. 40, No. 41, No. 42, No. 43, No. 44, No. 45, No. 46, No. 47, No. 48, No. 49, No. 50, No. 51, No. 52, No. 53, No. 54, No. 55, No. 56, No. 57, No. 58, No. 59, No. 60, No. 61, No. 62, No. 63, No. 64, No. 65, No. 66, No. 67, No. 68, No. 69, No. 70, No. 71, No. 72, No. 73, No. 74, No. 75, No. 76, No. 77, No. 78, No. 79, or No. 80 of Table 3, or any combination thereof is measured in a cell (e.g., a test cell) from a sample comprising leukemia stem cells and non-leukemia stem cells.

In some embodiments, if the level(s) of leukemia stem cell marker No. 1, No. 2, No. 3, No. 4, No. 5, No. 6, No. 7, No. 8, or No. 9 of Table 3, or any combination thereof is higher in a test cell from the sample than a non-leukemia stem cell, then the test cell is a B-cell ALL stem cell. In other words, a B-cell ALL stem cell has a higher expression level of TP53INP2, ARHGAP23, LOC100129516, SMAD2, TBL1XR1, NUPL1, SON, MTPN, TBC1D10B, or any combination thereof than a cell that is not a B-cell ALL stem cell. If the level(s) of leukemia stem cell marker No. 10, No. 11, No. 12, No. 13, No. 14, No. 15, No. 16, No. 17, No. 18, No. 19, No. 20, No. 21, No. 22, No. 23, No. 24, No. 25, No. 26, No. 27, No. 28, No. 29, No. 30, 31, No. 32, No. 33, No. 34, No. 35, No. 36, No. 37, No. 38, No. 39, No. 40, No. 41, No. 42, No. 43, No. 44, No. 45, No. 46, No. 47, No. 48, No. 49, No. 50, No. 51, No. 52, No. 53, No. 54, No. 55, No. 56, No. 57, No. 58, No. 59, No. 60, No. 61, No. 62, No. 63, No. 64, No. 65, No. 66, No. 67, No. 68, No. 69, No. 70, No. 71, No. 72, No. 73, No. 74, No. 75, No. 76, No. 77, No. 78, No. 79, or No. 80 of Table 3, or any combination thereof is lower in the test cell than a non-leukemia stem cell, the test cell is classified as a B-cell ALL stem cell.

TABLE 3

80 Leukemia Stem Cell Markers for B-cell ALL

| No. | Agilent Probe Name | Expression Level | Gene Symbol | Description | Entrez GeneID | Genbank Accession No. |
| --- | --- | --- | --- | --- | --- | --- |
| 1 | A_24_P357465 | up | TP53INP2 | *Homo sapiens* tumor protein p53 inducible nuclear protein 2 (TP53INP2), mRNA [NM_021202] | 58476 | NM_021202 |
| 2 | A_33_P3358914 | up | ARHGAP23 | *Homo sapiens* Rho GTPase activating protein 23 (ARHGAP23), mRNA [NM_001199417] | 57636 | NM_001199417 |
| 3 | A_32_P214284 | up | LOC100129516 | PREDICTED: *Homo sapiens* uncharacterized LOC100129516 (LOC100129516), misc_RNA [XR_159429] | 100129516 | XR_159429 |
| 4 | A_32_P12580 | up | SMAD2 | *Homo sapiens* SMAD family member 2 (SMAD2), transcript variant 2, mRNA [NM_001003652] | 4087 | NM_001003652 |
| 5 | A_23_P212552 | up | TBL1XR1 | *Homo sapiens* transducin (beta)-like 1 X-linked receptor 1 (TBL1XR1), mRNA [NM_024665] | 79718 | NM_024665 |
| 6 | A_23_P390190 | up | NUPL1 | *Homo sapiens* nucleoporin like 1 (NUPL1), transcript variant 1, mRNA [NM_014089] | 9818 | NM_014089 |

TABLE 3-continued

| | | | | | | |
|---|---|---|---|---|---|---|
| | | 80 Leukemia Stem Cell Markers for B-cell ALL | | | | |
| No. | Agilent Probe Name | Expression Level | Gene Symbol | Description | Entrez GeneID | Genbank Accession No. |
| 7 | A_23_P402733 | up | SON | *Homo sapiens* SON DNA binding protein (SON), transcript variant b, mRNA [NM_032195] | 6651 | NM_032195 |
| 8 | A_24_P55465 | up | MTPN | *Homo sapiens* myotrophin (MTPN), mRNA [NM_145808] | 136319 | NM_145808 |
| 9 | A_33_P3219197 | up | TBC1D10B | *Homo sapiens* TBC1 domain family, member 10B (TBC1D10B), mRNA [NM_015527] | 26000 | NM_015527 |
| 10 | A_23_P213706 | down | IL4 | *Homo sapiens* interleukin 4 (IL4), transcript variant 1, mRNA [NM_000589] | 3565 | NM_000589 |
| 11 | A_33_P3337977 | down | FIG4 | FIG4 phosphoinositide 5-phosphatase [Source: HGNC Symbol; Acc: HGNC: 16873] [ENST00000368941] | 9896 | |
| 12 | A_23_P81690 | down | COX7A2 | *Homo sapiens* cytochrome c oxidase subunit VIIa polypeptide 2 (liver) (COX7A2), transcript variant 1, mRNA [NM_001865] | 1347 | NM_001865 |
| 13 | A_23_P391689 | down | PET100 | *Homo sapiens* PET100 homolog (*S. cerevisiae*) (PET100), transcript variant 1, mRNA [NM_001171155] | 100131801 | NM_001171155 |
| 14 | A_33_P3353263 | down | CYB5RL | cytochrome b5 reductase-like [Source: HGNC Symbol; Acc: HGNC: 32220] [ENST00000462299] | 606495 | BC071735 |
| 15 | A_23_P148785 | down | SFT2D2 | *Homo sapiens* SFT2 domain containing 2 (SFT2D2), mRNA [NM_199344] | 375035 | NM_199344 |
| 16 | A_33_P3229017 | down | | family with sequence similarity 53, member C [Source: HGNC Symbol; Acc: HGNC: 1336] [ENST00000506710] | | XR_425872 |
| 17 | A_33_P3549874 | down | LOC255177 | PREDICTED: *Homo sapiens* uncharacterized LOC255177 (RP11-299H22.1), misc_RNA [XR_243167] | 255177 | XR_243167 |
| 18 | A_33_P3209096 | down | CD58 | *Homo sapiens* CD58 molecule (CD58), transcript variant 1, mRNA [NM_001779] | 965 | NM_001779 |

TABLE 3-continued

80 Leukemia Stem Cell Markers for B-cell ALL

| No. | Agilent Probe Name | Expression Level | Gene Symbol | Description | Entrez GeneID | Genbank Accession No. |
|---|---|---|---|---|---|---|
| 19 | A_32_P168247 | down | COX6A1 | Homo sapiens cytochrome c oxidase subunit VIa polypeptide 1 (COX6A1), mRNA [NM_004373] | 1337 | NM_004373 |
| 20 | A_23_P98410 | down | CD3G | Homo sapiens CD3g molecule, gamma (CD3-TCR complex) (CD3G), mRNA [NM_000073] | 917 | NM_000073 |
| 21 | A_23_P94230 | down | LY96 | Homo sapiens lymphocyte antigen 96 (LY96), transcript variant 1, mRNA [NM_015364] | 23643 | NM_015364 |
| 22 | A_33_P3273020 | down | FKBP2 | Homo sapiens FK506 binding protein 2, 13 kDa (FKBP2), transcript variant 1, mRNA [NM_004470] | 2286 | NM_004470 |
| 23 | A_33_P3404989 | down | HIST1H3H | Homo sapiens histone cluster 1, H3h (HIST1H3H), mRNA [NM_003536] | 8357 | NM_003536 |
| 24 | A_19_P00809746 | down | chr21: 39497834-39497775 | | | |
| 25 | A_19_P00802837 | down | chr9: 2691753-2691812 | | | |
| 26 | A_19_P00322915 | down | chr4: 53579123-53579064 | | | |
| 27 | A_33_P3273584 | down | SCARNA2 | Homo sapiens small Cajal body-specific RNA 2 (SCARNA2), guide RNA [NR_003023] | 677766 | NR_003023 |
| 28 | A_23_P45475 | down | GLA | Homo sapiens galactosidase, alpha (GLA), mRNA [NM_000169] | 2717 | NM_000169 |
| 29 | A_24_P154006 | down | NDUFB9 | Homo sapiens NADH dehydrogenase (ubiquinone) 1 beta subcomplex, 9, 22 kDa (NDUFB9), transcript variant 1, mRNA [NM_005005] | 4715 | NM_005005 |
| 30 | A_23_P87500 | down | ORMDL2 | Homo sapiens ORMDL sphingolipid biosynthesis regulator 2 (ORMDL2), mRNA [NM_014182] | 29095 | NM_014182 |
| 31 | A_23_P421011 | down | KAZALD1 | Homo sapiens Kazal-type serine peptidase inhibitor domain 1 (KAZALD1), mRNA [NM_030929] | 81621 | NM_030929 |
| 32 | A_19_P00320700 | down | chr8: 95986895-95986836 | | | |
| 33 | A_33_P3668839 | down | LOC644656 | Homo sapiens uncharacterized LOC644656 (LOC644656), long non-coding RNA [NR_036539] | 644656 | NR_036539 |

TABLE 3-continued

80 Leukemia Stem Cell Markers for B-cell ALL

| No. | Agilent Probe Name | Expression Level | Gene Symbol | Description | Entrez GeneID | Genbank Accession No. |
|---|---|---|---|---|---|---|
| 34 | A_33_P3382595 | down | RN7SK | *Homo sapiens* RNA, 7SK small nuclear (RN7SK), small nuclear RNA [NR_001445] | 125050 | NR_001445 |
| 35 | A_33_P3418000 | down | RELL1 | *Homo sapiens* RELT-like 1 (RELL1), transcript variant 2, mRNA [NM_001085399] | 768211 | NM_001085399 |
| 36 | A_33_P3298440 | down | LOC729324 | *Homo sapiens* cDNA FLJ31019 fis, clone HLUNG2000362. [AK055581] | 729324 | AK055581 |
| 37 | A_19_P00318964 | down | | Q59HD7_HUMAN (Q59HD7) Very low-density lipoprotein receptor variant (Fragment), partial (10%) [THC2721022] | | |
| 38 | A_23_P96209 | down | REEP4 | *Homo sapiens* receptor accessory protein 4 (REEP4), mRNA [NM_025232] | 80346 | NM_025232 |
| 39 | A_32_P107029 | down | NAPSA | *Homo sapiens* napsin A aspartic peptidase (NAPSA), mRNA [NM_004851] | 9476 | NM_004851 |
| 40 | A_33_P3390107 | down | RNA18S5 | *Homo sapiens* RNA, 18S ribosomal 5 (RNA18S5), ribosomal RNA [NR_003286] | 100008588 | NR_003286 |
| 41 | A_19_P00812257 | down | LINC01191 | *Homo sapiens* long intergenic non-protein coding RNA 1191 (LINC01191), long non-coding RNA [NR_034128] | 440900 | NR_034128 |
| 42 | A_19_P00803914 | down | chr9: 2539421-2539480 | | | |
| 43 | A_33_P3346292 | down | UBAP2 | ubiquitin associated protein 2 [Source: HGNC Symbol; Acc: HGNC: 14185] [ENST00000379225] | 55833 | AY358682 |
| 44 | A_19_P00317204 | down | chr4: 74399742-74399683 | | | |
| 45 | A_19_P00807884 | down | chr14: 58759635-58759694 | | | |
| 46 | A_33_P3335522 | down | FCRL5 | *Homo sapiens* Fc receptor-like 5 (FCRL5), transcript variant 2, mRNA [NM_001195388] | 83416 | NM_001195388 |
| 47 | A_24_P301063 | down | PLEKHG6 | *Homo sapiens* pleckstrin homology domain containing, family G (with RhoGef domain) member 6 (PLEKHG6), transcript variant 1, mRNA [NM_018173] | 55200 | NM_018173 |
| 48 | A_19_P00324071 | down | chrX: 135955146-135955205 | | | |

TABLE 3-continued

80 Leukemia Stem Cell Markers for B-cell ALL

| No. | Agilent Probe Name | Expression Level | Gene Symbol | Description | Entrez GeneID | Genbank Accession No. |
|---|---|---|---|---|---|---|
| 49 | A_23_P40240 | down | CTSZ | *Homo sapiens* cathepsin Z (CTSZ), mRNA [NM_001336] | 1522 | NM_001336 |
| 50 | A_33_P3227217 | down | SNORA81 | *Homo sapiens* small nucleolar RNA, H/ACA box 81 (SNORA81), small nucleolar RNA [NR_002989] | 677847 | NR_002989 |
| 51 | A_23_P38618 | down | PIGL | *Homo sapiens* phosphatidylinositol glycan anchor biosynthesis, class L (PIGL), mRNA [NM_004278] | 9487 | NM_004278 |
| 52 | A_19_P00316649 | down | chr15: 58538397-58538338 | aldehyde dehydrogenase 1 family, member A2 [Source: HGNC Symbol; Acc: HGNC: 15472] [ENST00000559625] | | XR_243155 |
| 53 | A_23_P388871 | down | HIST4H4 | *Homo sapiens* histone cluster 4, H4 (HIST4H4), mRNA [NM_175054] | 121504 | NM_175054 |
| 54 | A_32_P221305 | down | LINC00937 | *Homo sapiens* long intergenic non-protein coding RNA 937 (LINC00937), long non-coding RNA [NR_024420] | 389634 | NR_024420 |
| 55 | A_24_P276932 | down | ATP6V1C2 | *Homo sapiens* ATPase, H+ transporting, lysosomal 42 kDa, VI subunit C2 (ATP6V1C2), transcript variant 1, mRNA [NM_001039362] | 245973 | NM_001039362 |
| 56 | A_19_P00323062 | down | chr5: 124748130-124748189 | | | |
| 57 | A_19_P00322687 | down | ERVMER34-1 | *Homo sapiens* endogenous retrovirus group MER34, member 1 (ERVMER34-1), transcript variant 2, mRNA [NM_001242690] | 100288413 | NM_001242690 |
| 58 | A_19_P00320136 | down | chr15: 25333923-25333982 | small nucleolar RNA, C/D box 116-20 [Source: HGNC Symbol; Acc: HGNC: 33086] [ENST00000567527] | | JX629743 |
| 59 | A_24_P23445 | down | RNU12 | *Homo sapiens* RNA, U12 small nuclear (RNU12), small nuclear RNA [NR_029422] | 267010 | NR_029422 |
| 60 | A_19_P00327750 | down | chr4: 93191760-93191819 | | | |
| 61 | A_19_P00316075 | down | chr4: 53579273-53579332 | Q30VC0_DESDG (Q30VC0) Flagellar biosynthetic protein FliP, partial (8%) [THC2498220] | | |

TABLE 3-continued

80 Leukemia Stem Cell Markers for B-cell ALL

| No. | Agilent Probe Name | Expression Level | Gene Symbol | Description | Entrez GeneID | Genbank Accession No. |
|---|---|---|---|---|---|---|
| 62 | A_32_P99019 | down | FMR1NB | Homo sapiens fragile X mental retardation 1 neighbor (FMR1NB), mRNA [NM_152578] | 158521 | NM_152578 |
| 63 | A_19_P00320259 | down | ERVMER34-1 | Homo sapiens endogenous retrovirus group MER34, member 1 (ERVMER34-1), transcript variant 2, mRNA [NM_001242690] | 100288413 | NM_001242690 |
| 64 | A_19_P00318261 | down | SNORA26 | Homo sapiens small nucleolar RNA, H/ACA box 26 (SNORA26), small nucleolar RNA [NR_003016] | 677810 | NR_003016 |
| 65 | A_19_P00318418 | down | TBXAS1 | Homo sapiens thromboxane A synthase 1 (platelet) (TBXAS1), transcript variant 5, mRNA [NM_001166254] | 6916 | NM_001166254 |
| 66 | A_19_P00318569 | down | chr20: 37049686-37049745 | ALU1_HUMAN (P39188) Alu subfamily J sequence contamination warning entry, partial (8%) [THC2540047] | | |
| 67 | A_33_P3284715 | down | SCARNA7 | Homo sapiens small Cajal body-specific RNA 7 (SCARNA7), guide RNA [NR_003001] | 677767 | NR_003001 |
| 68 | A_33_P3359168 | down | LOC101927151 | Homo sapiens uncharacterized LOC101927151 (LOC101927151), transcript variant 1, long non-coding RNA [NR_110687] | 101927151 | NR_110687 |
| 69 | A_19_P00812901 | down | chr8: 32872723-32872782 | | | |
| 70 | A_33_P3234124 | down | FAM132B | Homo sapiens family with sequence similarity 132, member B (FAM132B), mRNA [NM_001291832] | 151176 | NM_001291832 |
| 71 | A_33_P3671291 | down | SNORA12 | EST91069 Synovial sarcoma Homo sapiens cDNA 5' end, mRNA sequence [AA378382] | 677800 | AA378382 |
| 72 | A_33_P3420496 | down | SNORA53 | Homo sapiens small nucleolar RNA, H/ACA box 53 (SNORA53), small nucleolar RNA [NR_003015] | 677832 | NR_003015 |
| 73 | A_19_P00807268 | down | chr4: 76466756-76466697 | | | |
| 74 | A_19_P00813375 | down | unmapped | | | |
| 75 | A_19_P00318425 | down | ERVMER34-1 | Homo sapiens endogenous retrovirus group MER34, member 1 (ERVMER34-1), transcript variant 2, mRNA [NM_001242690] | 100288413 | NM_001242690 |

TABLE 3-continued

80 Leukemia Stem Cell Markers for B-cell ALL

| No. | Agilent Probe Name | Expression Level | Gene Symbol | Description | Entrez GeneID | Genbank Accession No. |
|---|---|---|---|---|---|---|
| 76 | A_33_P3258146 | down | LOC100130539 | Homo sapiens uncharacterized LOC100130539 (LOC100130539), mRNA [NM_001258000] | 100130539 | NM_001258000 |
| 77 | A_33_P3658861 | down | SNORA26 | qi73d08.y5 NCI_CGAP_Ov26 Homo sapiens cDNA clone IMAGE: 1862127 5', mRNA sequence [AI792523] | 677810 | AI792523 |
| 78 | A_23_P53329 | down | FLJ13224 | Homo sapiens uncharacterized LOC79857 (FLJ13224), long non-coding RNA [NR_026806] | 79857 | NR_026806 |
| 79 | A_33_P3327519 | down | SNORA74A | Homo sapiens small nucleolar RNA, H/ACA box 74A (SNORA74A), small nucleolar RNA [NR_002915] | 26821 | NR_002915 |
| 80 | A_19_P00803996 | down | chr1: 181391989-181392048 | | | |

In some embodiments, the methods provided herein include measuring or detecting the expression level of at least one leukemia stem cell marker of Table 4, e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, or 105 leukemia stem cell markers of Table 4, in a cell (e.g., a test cell). In other words, the methods include measuring the expression level of 1 to 105 different leukemia stem cell markers set forth in Table 4 in a test cell. The cell can also have a low level of 2-NBDG fluorescence compared to a non-cancer stem cell. In other embodiments, the test cell is suspected of being a leukemia stem cell such as a T-cell ALL stem cell.

In some embodiments, the expression level of the leukemia stem cell marker No. 1, No. 2, No. 3, No. 4, No. 5, No. 6, No. 7, No. 8, No. 9, No. 10, No. 11, No. 12, No. 13, No. 14, No. 15, No. 16, No. 17, No. 18, No. 19, No. 20, No. 21, No. 22, No. 23, No. 24, No. 25, No. 26, No. 27, No. 28, No. 29, No. 30, 31, No. 32, No. 33, No. 34, No. 35, No. 36, No. 37, No. 38, No. 39, No. 40, No. 41, No. 42, No. 43, No. 44, No. 45, No. 46, No. 47, No. 48, No. 49, No. 50, No. 51, No. 52, No. 53, No. 54, No. 55, No. 56, No. 57, No. 58, No. 59, No. 60, No. 61, No. 62, No. 63, No. 64, No. 65, No. 66, No. 67, No. 68, No. 69, No. 70, No. 71, No. 72, No. 73, No. 74, No. 75, No. 76, No. 77, No. 78, No. 79, No. 80, No. 81, No. 82, No. 83, No. 84, No. 85, No. 86, No. 87, No. 88, No. 89, No. 90, No. 91, No. 92, No. 93, No. 94, No. 95, No. 96, No. 97, No. 98, No. 99, No. 100, No. 101, No. 102, No. 103, No. 104, or No. 105 of Table 4, or any combination thereof, is measured in a cell from a sample comprising leukemia stem cells (e.g., T-cell ALL stem cells) and non-leukemia stem cells.

In some embodiments, if the expression level(s) of the leukemia stem cell marker No. 1, No. 2, No. 3, No. 4, No. 5, No. 6, No. 7, No. 8, No. 9, No. 10, No. 11, No. 12, No. 13, No. 14, No. 15, No. 16, No. 17, No. 18, or No. 19 of Table 4, or any combination thereof is measured and is higher in the test cell compared to a non-leukemia stem cell, the test cell is classified as a leukemia stem cell or more specifically, a T-cell ALL stem cell. The following markers are expressed at a higher level in a T-cell ALL stem cell than a cell that is not a T-cell ALL stem cell: ELMO2, AACS, SEC16A, EXOC2, ATPAF1, ATPAF1, POLE, NUPL1, RBM23, ZNF28, TNIK, TBL1XR1, ATP2A3, RAI1, TDG, SON, MTPN, LINC01503, DDX11, and TBC1D10B. In other embodiments, if the expression level(s) of the leukemia stem cell marker No. 20, No. 21, No. 22, No. 23, No. 24, No. 25, No. 26, No. 27, No. 28, No. 29, No. 30, 31, No. 32, No. 33, No. 34, No. 35, No. 36, No. 37, No. 38, No. 39, No. 40, No. 41, No. 42, No. 43, No. 44, No. 45, No. 46, No. 47, No. 48, No. 49, No. 50, No. 51, No. 52, No. 53, No. 54, No. 55, No. 56, No. 57, No. 58, No. 59, No. 60, No. 61, No. 62, No. 63, No. 64, No. 65, No. 66, No. 67, No. 68, No. 69, No. 70, No. 71, No. 72, No. 73, No. 74, No. 75, No. 76, No. 77, No. 78, No. 79, No. 80, No. 81, No. 82, No. 83, No. 84, No. 85, No. 86, No. 87, No. 88, No. 89, No. 90, No. 91, No. 92, No. 93, No. 94, No. 95, No. 96, No. 97, No. 98, No. 99, No. 100, No. 101, No. 102, No. 103, No. 104, or No. 105 of Table 4, or any combination thereof is measured and is lower in the test cell compared to a non-leukemia stem cell, the test cell is classified as a leukemia stem cell or more specifically, a T-cell ALL stem cell.

TABLE 4

105 Leukemia Stem Cell Markers for T-cell ALL

| No. | Agilent Probe Name | Expression Level | Gene Symbol | Description | Entrez GeneID | Genbank Accession No. |
|---|---|---|---|---|---|---|
| 1 | A_23_P210538 | up | ELMO2 | Homo sapiens engulfment and cell motility 2 (ELMO2), transcript variant 2, mRNA [NM_182764] | 63916 | NM_182764 |
| 2 | A_33_P3403392 | up | AACS | Homo sapiens acetoacetyl-CoA synthetase (AACS), mRNA [NM_023928] | 65985 | NM_023928 |
| 3 | A_33_P3382267 | up | SEC16A | Homo sapiens SEC16 homolog A (S. cerevisiae) (SEC16A), transcript variant 1, mRNA [NM_014866] | 9919 | NM_014866 |
| 4 | A_23_P214354 | up | EXOC2 | Homo sapiens exocyst complex component 2 (EXOC2), transcript variant 1, mRNA [NM_018303] | 55770 | NM_018303 |
| 5 | A_24_P919899 | up | ATPAF1 | ATP synthase mitochondrial F1 complex assembly factor 1 [Source: HGNC Symbol; Acc: HGNC: 18803] [ENST00000576409] | 64756 | AF111705 |
| 6 | A_33_P3695548 | up | POLE | Homo sapiens polymerase (DNA directed), epsilon, catalytic subunit (POLE), mRNA [NM_006231] | 5426 | NM_006231 |
| 7 | A_23_P390190 | up | NUPL1 | Homo sapiens nucleoporin like 1 (NUPL1), transcript variant 1, mRNA [NM_014089] | 9818 | NM_014089 |
| 8 | A_24_P219156 | up | RBM23 | Homo sapiens RNA binding motif protein 23 (RBM23), transcript variant 1, mRNA [NM_001077351] | 55147 | NM_001077351 |
| 9 | A_24_P282043 | up | ZNF28 | Homo sapiens zinc finger protein 28 (ZNF28), transcript variant 1, mRNA [NM_006969] | 7576 | NM_006969 |
| 10 | A_24_P350576 | up | TNIK | Homo sapiens TRAF2 and NCK interacting kinase (TNIK), transcript variant 1, mRNA [NM_015028] | 23043 | NM_015028 |
| 11 | A_23_P212552 | up | TBL1XR1 | Homo sapiens transducin (beta)-like 1 X-linked receptor 1 (TBL1XR1), mRNA [NM_024665] | 79718 | NM_024665 |
| 12 | A_24_P202319 | up | ATP2A3 | Homo sapiens ATPase, Ca++ transporting, ubiquitous (ATP2A3), transcript variant 7, mRNA [NM_174958] | 489 | NM_174958 |
| 13 | A_33_P3320499 | up | RAI1 | Homo sapiens retinoic acid induced 1 (RAI1), mRNA [NM_030665] | 10743 | NM_030665 |
| 14 | A_33_P3357445 | up | TDG | Homo sapiens thymine-DNA glycosylase (TDG), mRNA [NM_003211] | 6996 | NM_003211 |
| 15 | A_23_P402733 | up | SON | Homo sapiens SON DNA binding protein (SON), transcript variant b, mRNA [NM_032195] | 6651 | NM_032195 |
| 16 | A_24_P55465 | up | MTPN | Homo sapiens myotrophin (MTPN), mRNA [NM_145808] | 136319 | NM_145808 |
| 17 | A_19_P00322442 | up | LINC01503 | Homo sapiens long intergenic non-protein coding RNA 1503 (LINC01503), transcript variant 1, long non-coding RNA [NR_120685] | 100506119 | NR_120685 |
| 18 | A_33_P3322307 | up | DDX11 | Homo sapiens DEAD/H (Asp-Glu-Ala-Asp/His) box helicase 11 (DDX11), transcript variant 5, mRNA [NM_001257145] | 1663 | NM_001257145 |

TABLE 4-continued

105 Leukemia Stem Cell Markers for T-cell ALL

| No. | Agilent Probe Name | Expression Level | Gene Symbol | Description | Entrez GeneID | Genbank Accession No. |
|---|---|---|---|---|---|---|
| 19 | A_33_P3219197 | up | TBC1D10B | Homo sapiens TBC1 domain family, member 10B (TBC1D10B), mRNA [NM_015527] | 26000 | NM_015527 |
| 20 | A_19_P00320136 | down | chr15: 25333923-25333982 | small nucleolar RNA, C/D box 116-20 [Source: HGNC Symbol; Acc: HGNC: 33086] [ENST00000567527] | | JX629743 |
| 21 | A_19_P00318261 | down | SNORA26 | Homo sapiens small nucleolar RNA, H/ACA box 26 (SNORA26), small nucleolar RNA [NR_003016] | 677810 | NR_003016 |
| 22 | A_19_P00320259 | down | ERVMER34-1 | Homo sapiens endogenous retrovirus group MER34, member 1 (ERVMER34-1), transcript variant 2, mRNA [NM_001242690] | 100288413 | NM_001242690 |
| 23 | A_19_P00322687 | down | ERVMER34-1 | Homo sapiens endogenous retrovirus group MER34, member 1 (ERVMER34-1), transcript variant 2, mRNA [NM_001242690] | 100288413 | NM_001242690 |
| 24 | A_19_P00316075 | down | chr4: 53579273-53579332 | Q30VC0_DESDG (Q30VC0) Flagellar biosynthetic protein FliP, partial (8%) [THC2498220] | | |
| 25 | A_23_P213706 | down | IL4 | Homo sapiens interleukin 4 (IL4), transcript variant 1, mRNA [NM_000589] | 3565 | NM_000589 |
| 26 | A_33_P3209096 | down | CD58 | Homo sapiens CD58 molecule (CD58), transcript variant 1, mRNA [NM_001779] | 965 | NM_001779 |
| 27 | A_23_P94230 | down | LY96 | Homo sapiens lymphocyte antigen 96 (LY96), transcript variant 1, mRNA [NM_015364] | 23643 | NM_015364 |
| 28 | A_33_P3273584 | down | SCARNA2 | Homo sapiens small Cajal body-specific RNA 2 (SCARNA2), guide RNA [NR_003023] | 677766 | NR_003023 |
| 29 | A_33_P3844650 | down | ANGPTL2 | Homo sapiens angiopoietin-like 2 (ANGPTL2), mRNA [NM_012098] | 23452 | NM_012098 |
| 30 | A_23_P81690 | down | COX7A2 | Homo sapiens cytochrome c oxidase subunit VIIa polypeptide 2 (liver) (COX7A2), transcript variant 1, mRNA [NM_001865] | 1347 | NM_001865 |
| 31 | A_23_P391689 | down | PET100 | Homo sapiens PET100 homolog (S. cerevisiae) (PET100), transcript variant 1, mRNA [NM_001171155] | 100131801 | NM_001171155 |
| 32 | A_33_P3549874 | down | LOC255177 | PREDICTED: Homo sapiens uncharacterized LOC255177 (RP11-299H22.1), misc_RNA [XR_243167] | 255177 | XR_243167 |
| 33 | A_33_P3363082 | down | SCARNA5 | Homo sapiens small Cajal body-specific RNA 5 (SCARNA5), guide RNA [NR_003008] | 677775 | NR_003008 |
| 34 | A_33_P3345743 | down | PFN1P2 | Homo sapiens profilin 1 pseudogene 2 (PFN1P2), non-coding RNA [NR_003242] | 767846 | NR_003242 |
| 35 | A_33_P3273020 | down | FKBP2 | Homo sapiens FK506 binding protein 2, 13 kDa (FKBP2), transcript variant 1, mRNA [NM_004470] | 2286 | NM_004470 |

TABLE 4-continued

105 Leukemia Stem Cell Markers for T-cell ALL

| No. | Agilent Probe Name | Expression Level | Gene Symbol | Description | Entrez GeneID | Genbank Accession No. |
|---|---|---|---|---|---|---|
| 36 | A_19_P00809746 | down | chr21: 39497834-39497775 | | | |
| 37 | A_23_P148785 | down | SFT2D2 | *Homo sapiens* SFT2 domain containing 2 (SFT2D2), mRNA [NM_199344] | 375035 | NM_199344 |
| 38 | A_19_P00321344 | down | LINC01237 | long intergenic non-protein coding RNA 1237 [Source: HGNC Symbol; Acc: HGNC: 49793] [ENST00000429947] | 101927289 | |
| 39 | A_33_P3671291 | down | SNORA12 | EST91069 Synovial sarcoma *Homo sapiens* cDNA 5' end, mRNA sequence [AA378382] | 677800 | AA378382 |
| 40 | A_23_P316850 | down | ODF3L2 | *Homo sapiens* outer dense fiber of sperm tails 3-like 2 (ODF3L2), mRNA [NM_182577] | 284451 | NM_182577 |
| 41 | A_33_P3346292 | down | UBAP2 | ubiquitin associated protein 2 [Source: HGNC Symbol; Acc: HGNC: 14185] [ENST00000379225] | 55833 | AY358682 |
| 42 | A_23_P142187 | down | HIF3A | *Homo sapiens* hypoxia inducible factor 3, alpha subunit (HIF3A), transcript variant 2, mRNA [NM_022462] | 64344 | NM_022462 |
| 43 | A_33_P3390107 | down | RNA18S5 | *Homo sapiens* RNA, 18S ribosomal 5 (RNA18S5), ribosomal RNA [NR_003286] | 100008588 | NR_003286 |
| 44 | A_33_P3418000 | down | RELL1 | *Homo sapiens* RELT-like 1 (RELL1), transcript variant 2, mRNA [NM_001085399] | 768211 | NM_001085399 |
| 45 | A_32_P168247 | down | COX6A1 | *Homo sapiens* cytochrome c oxidase subunit VIa polypeptide 1 (COX6A1), mRNA [NM_004373] | 1337 | NM_004373 |
| 46 | A_19_P00802837 | down | chr9: 2691753-2691812 | | | |
| 47 | A_33_P3229017 | down | chr5: 137672717-137672776 | family with sequence similarity 53, member C [Source: HGNC Symbol; Acc: HGNC: 1336] [ENST00000506710] | | XR_425872 |
| 48 | A_19_P00323062 | down | chr5: 124748130-124748189 | | | |
| 49 | A_23_P43490 | down | CDKN2A | *Homo sapiens* cyclin-dependent kinase inhibitor 2A (CDKN2A), transcript variant 3, mRNA [NM_058197] | 1029 | NM_058197 |
| 50 | A_33_P3404032 | down | HIST3H2A | *Homo sapiens* histone cluster 3, H2a (HIST3H2A), mRNA [NM_033445] | 92815 | NM_033445 |
| 51 | A_33_P3353263 | down | CYB5RL | cytochrome b5 reductase-like [Source: HGNC Symbol; Acc: HGNC: 32220] [ENST00000462299] | 606495 | BC071735 |
| 52 | A_33_P3399064 | down | RNA5-8S5 | *Homo sapiens* RNA, 5.8S ribosomal 5 (RNA5-8S5), ribosomal RNA [NR_003285] | 100008587 | NR_003285 |
| 53 | A_24_P258235 | down | OR5L2 | *Homo sapiens* olfactory receptor, family 5, subfamily L, member 2 (OR5L2), mRNA [NM_001004739] | 26338 | NM_001004739 |

TABLE 4-continued

105 Leukemia Stem Cell Markers for T-cell ALL

| No. | Agilent Probe Name | Expression Level | Gene Symbol | Description | Entrez GeneID | Genbank Accession No. |
|---|---|---|---|---|---|---|
| 54 | A_23_P70007 | down | HMMR | *Homo sapiens* hyaluronan-mediated motility receptor (RHAMM) (HMMR), transcript variant 2, mRNA [NM_012484] | 3161 | NM_012484 |
| 55 | A_23_P98410 | down | CD3G | *Homo sapiens* CD3g molecule, gamma (CD3-TCR complex) (CD3G), mRNA [NM_000073] | 917 | NM_000073 |
| 56 | A_33_P3668839 | down | LOC644656 | *Homo sapiens* uncharacterized LOC644656 (LOC644656), long non-coding RNA [NR_036539] | 644656 | NR_036539 |
| 57 | A_23_P127721 | down | P2RX3 | *Homo sapiens* purinergic receptor P2X, ligand gated ion channel, 3 (P2RX3), mRNA [NM_002559] | 5024 | NM_002559 |
| 58 | A_19_P00322915 | down | chr4: 53579123-53579064 | | | |
| 59 | A_19_P00317523 | down | chr6: 86387104-86387045 | small nucleolar RNA host gene 5 (non-protein coding) [Source: HGNC Symbol; Acc: HGNC: 21026] [ENST00000433843] | | |
| 60 | A_33_P3237574 | down | HLA-A | *Homo sapiens* major histocompatibility complex, class I, A (HLA-A), transcript variant 2 (A*01:01:01:01 allele), mRNA [NM_001242758] | 3105 | NM_001242758 |
| 61 | A_19_P00326417 | down | chr21: 4790147-44790206 | | | |
| 62 | A_33_P3244478 | down | ACVR2B-AS1 | *Homo sapiens* ACVR2B antisense RNA 1 (ACVR2B-AS1), long non-coding RNA [NR_028389] | 100128640 | NR_028389 |
| 63 | A_19_P00807268 | down | chr4: 76466756-76466697 | | | |
| 64 | A_19_P00809587 | down | chr8: 96321995-96321936 | | | |
| 65 | A_19_P00326467 | down | chrX: 71238427-71238486 | | | |
| 66 | A_19_P00328490 | down | chr5: 167703271-167703330 | | | |
| 67 | A_33_P3313622 | down | MIR17HG | *Homo sapiens* miR-17-92 cluster host gene (non-protein coding) (MIR17HG), transcript variant 1, long non-coding RNA [NR_027350] | 407975 | NR_027350 |
| 68 | A_33_P3383524 | down | LINC00923 | *Homo sapiens* long intergenic non-protein coding RNA 923 (LINC00923), transcript variant 1, long non-coding RNA [NR_024172] | 91948 | NR_024172 |
| 69 | A_23_P377860 | down | UMODL1-AS1 | *Homo sapiens* UMODL1 antisense RNA 1 (UMODL1-AS1), long non-coding RNA [NR_027243] | 150147 | NR_027243 |
| 70 | A_23_P4400 | down | KRTAP4-11 | *Homo sapiens* keratin associated protein 4-11 (KRTAP4-11), mRNA [NM_033059] | 653240 | NM_033059 |
| 71 | A_19_P00324071 | down | chrX: 135955146-135955205 | | | |

TABLE 4-continued

105 Leukemia Stem Cell Markers for T-cell ALL

| No. | Agilent Probe Name | Expression Level | Gene Symbol | Description | Entrez GeneID | Genbank Accession No. |
|---|---|---|---|---|---|---|
| 72 | A_33_P3261937 | down | RNASE13 | *Homo sapiens* ribonuclease, RNase A family, 13 (non-active) (RNASE13), mRNA [NM_001012264] | 440163 | NM_001012264 |
| 73 | A_19_P00812884 | down | chr10: 134137713- 134137772 | | | |
| 74 | A_33_P3258146 | down | LOC100130539 | *Homo sapiens* uncharacterized LOC100130539 (LOC100130539), mRNA [NM_001258000] | 100130539 | NM_001258000 |
| 75 | A_24_P631848 | down | chr1: 16860558- 16860499 | | | BC036435 |
| 76 | A_33_P3411315 | down | KRTAP3-3 | *Homo sapiens* keratin associated protein 3-3 (KRTAP3-3), mRNA [NM_033185] | 85293 | NM_033185 |
| 77 | A_23_P372860 | down | HIST1H2AC | *Homo sapiens* histone cluster 1, H2ac (HIST1H2AC), mRNA [NM_003512] | 8334 | NM_003512 |
| 78 | A_33_P3415843 | down | chr9: 131869680- 131869621 | BT006801 carnitine acetyltransferase {*Homo sapiens*} (exp = −1; wgp = 0; cg = 0), partial (18%) [THC2667880] | | |
| 79 | A_33_P3393734 | down | RPS27 | ribosomal protein S27 [Source: HGNC Symbol; Acc: HGNC: 10416] [ENST00000392558] | 6232 | |
| 80 | A_33_P3839897 | down | RNU4ATAC | HHAGE001732 Human liver regeneration after partial hepatectomy *Homo sapiens* cDNA, mRNA sequence [DW419002] | 100151683 | DW419002 |
| 81 | A_24_P276932 | down | ATP6V1C2 | *Homo sapiens* ATPase, H+ transporting, lysosomal 42 kDa, V1 subunit C2 (ATP6V1C2), transcript variant 1, mRNA [NM_001039362] | 245973 | NM_001039362 |
| 82 | A_33_P3235546 | down | RIMS3 | *Homo sapiens* regulating synaptic membrane exocytosis 3 (RIMS3), mRNA [NM_014747] | 9783 | NM_014747 |
| 83 | A_19_P00812428 | down | chrX: 71264431- 71264372 | | | |
| 84 | A_33_P3382595 | down | RN7SK | *Homo sapiens* RNA, 7SK small nuclear (RN7SK), small nuclear RNA [NR_001445] | 125050 | NR_001445 |
| 85 | A_19_P00808190 | down | chr8: 32869106- 32869047 | | | |
| 86 | A_19_P00807884 | down | chr14: 58759635- 58759694 | | | |
| 87 | A_24_P922631 | down | C5orf58 | *Homo sapiens* chromosome 5 open reading frame 58 (C5orf58), mRNA [NM_001102609] | 133874 | NM_001102609 |
| 88 | A_33_P3404989 | down | HIST1H3H | *Homo sapiens* histone cluster 1, H3h (HIST1H3H), mRNA [NM_003536] | 8357 | NM_003536 |
| 89 | A_24_P23445 | down | RNU12 | *Homo sapiens* RNA, U12 small nuclear (RNU12), small nuclear RNA [NR_029422] | 267010 | NR_029422 |

TABLE 4-continued

105 Leukemia Stem Cell Markers for T-cell ALL

| No. | Agilent Probe Name | Expression Level | Gene Symbol | Description | Entrez GeneID | Genbank Accession No. |
|---|---|---|---|---|---|---|
| 90 | A_19_P00327750 | down | chr4: 93191760-93191819 | | | |
| 91 | A_33_P3227217 | down | SNORA81 | *Homo sapiens* small nucleolar RNA, H/ACA box 81 (SNORA81), small nucleolar RNA [NR_002989] | 677847 | NR_002989 |
| 92 | A_33_P3337977 | down | FIG4 | FIG4 phosphoinositide 5-phosphatase [Source: HGNC Symbol; Acc: HGNC: 16873] [ENST00000368941] | 9896 | |
| 93 | A_33_P3658861 | down | SNORA26 | qi73d08.y5 NCI_CGAP_Ov26 *Homo sapiens* cDNA clone IMAGE: 1862127 5', mRNA sequence [AI792523] | 677810 | AI792523 |
| 94 | A_19_P00318569 | down | chr20: 37049686-37049745 | ALU1_HUMAN (P39188) Alu subfamily J sequence contamination warning entry, partial (8%) [THC2540047] | | |
| 95 | A_33_P3273459 | down | SPATA21 | spermatogenesis associated 21 [Source: HGNC Symbol; Acc: HGNC: 28026] [ENST00000466212] | 374955 | XR_241189 |
| 96 | A_19_P00810792 | down | chr11: 40105528-40105587 | | | |
| 97 | A_33_P3420496 | down | SNORA53 | *Homo sapiens* small nucleolar RNA, H/ACA box 53 (SNORA53), small nucleolar RNA [NR_003015] | 677832 | NR_003015 |
| 98 | A_32_P181527 | down | AARD | *Homo sapiens* alanine and arginine rich domain containing protein (AARD), mRNA [NM_001025357] | 441376 | NM_001025357 |
| 99 | A_24_P927325 | down | C2CD3 | *Homo sapiens* C2 calcium-dependent domain containing 3 (C2CD3), transcript variant 2, mRNA [NM_015531] | 26005 | NM_015531 |
| 100 | A_33_P3327519 | down | SNORA74A | *Homo sapiens* small nucleolar RNA, H/ACA box 74A (SNORA74A), small nucleolar RNA [NR_002915] | 26821 | NR_002915 |
| 101 | A_19_P00803996 | down | chr1: 181391989-181392048 | | | |
| 102 | A_19_P00812662 | down | chr12: 5401336-5401277 | | | |
| 103 | A_19_P00324839 | down | MALAT1 | *Homo sapiens* metastasis associated lung adenocarcinoma transcript 1 (non-protein coding) (MALAT1), long non-coding RNA [NR_002819] | 378938 | NR_002819 |
| 104 | A_23_P155463 | down | LRRC2 | *Homo sapiens* leucine rich repeat containing 2 (LRRC2), mRNA [NM_024512] | 79442 | NM_024512 |
| 105 | A_19_P00812901 | down | chr8: 32872723-32872782 | | | |

If the expression level of the measured leukemia stem cell marker(s) in the test cell is higher, e.g., at least about 25%, at least about 50%, at least about 90%, at least about 100%, at least about 1.5-fold, 2-fold, 2.5-fold, 3-fold, 3.5-fold, 4-fold, 4.5-fold, 5-fold or more, higher than the expression level of the same leukemia stem cell marker(s) in a non-leukemia stem cell, it is determined that the test cell is a leukemia stem cell. The non-leukemia stem cell can be a differentiated leukemia cell, a progenitor leukemia cell or a precursor leukemia cell. If the level(s) of leukemia stem cell marker No. 1, No. 2, No. 3, No. 4, No. 5, No. 6, No. 7, No. 8, or No. 9 of Table 3, or any combination thereof is higher, e.g., at least about 25%, at least about 50%, at least about 90%, at least about 100%, at least about 1.5-fold, 2-fold, 2.5-fold, 3-fold, 3.5-fold, 4-fold, 4.5-fold, 5-fold or more, higher in the test cell from the sample than the non-leukemia stem cell, then the test cell can be classified as a B-cell ALL stem cell. If the expression level(s) of the leukemia stem cell marker No. 1, No. 2, No. 3, No. 4, No. 5, No. 6, No. 7, No. 8, No. 9, No. 10, No. 11, No. 12, No. 13, No. 14, No. 15, No. 16, No. 17, No. 18, or No. 19 of Table 4, or any combination thereof is measured and is higher e.g., at least about 25%, at least about 50%, at least about 90%, at least about 100%, at least about 1.5-fold, 2-fold, 2.5-fold, 3-fold, 3.5-fold, 4-fold, 4.5-fold, 5-fold or more, higher in the test cell compared to a non-leukemia stem cell, the test cell can be classified as a T-cell ALL stem cell.

In other embodiments, if the expression level of the measured leukemia stem cell marker(s) in the test cell is lower, e.g., at least about 25%, at least about 50%, at least about 90%, at least about 100%, at least about 1.5-fold, 2-fold, 2.5-fold, 3-fold, 3.5-fold, 4-fold, 4.5-fold, 5-fold or more, lower than the expression level of the same leukemia stem cell marker(s) in a non-leukemia stem cell, it is determined that the test cell is a leukemia stem cell. If the level(s) of leukemia stem cell marker No. 10, No. 11, No. 12, No. 13, No. 14, No. 15, No. 16, No. 17, No. 18, No. 19, No. 20, No. 21, No. 22, No. 23, No. 24, No. 25, No. 26, No. 27, No. 28, No. 29, No. 30, 31, No. 32, No. 33, No. 34, No. 35, No. 36, No. 37, No. 38, No. 39, No. 40, No. 41, No. 42, No. 43, No. 44, No. 45, No. 46, No. 47, No. 48, No. 49, No. 50, No. 51, No. 52, No. 53, No. 54, No. 55, No. 56, No. 57, No. 58, No. 59, No. 60, No. 61, No. 62, No. 63, No. 64, No. 65, No. 66, No. 67, No. 68, No. 69, No. 70, No. 71, No. 72, No. 73, No. 74, No. 75, No. 76, No. 77, No. 78, No. 79, or No. 80 of Table 3, or any combination thereof is lower, e.g., at least about 25%, at least about 50%, at least about 90%, at least about 100%, at least about 1.5-fold, 2-fold, 2.5-fold, 3-fold, 3.5-fold, 4-fold, 4.5-fold, 5-fold or more, lower in the test cell than a non-leukemia stem cell, the test cell is classified as a B-cell ALL stem cell. If the expression level(s) of the leukemia stem cell marker No. 20, No. 21, No. 22, No. 23, No. 24, No. 25, No. 26, No. 27, No. 28, No. 29, No. 30, 31, No. 32, No. 33, No. 34, No. 35, No. 36, No. 37, No. 38, No. 39, No. 40, No. 41, No. 42, No. 43, No. 44, No. 45, No. 46, No. 47, No. 48, No. 49, No. 50, No. 51, No. 52, No. 53, No. 54, No. 55, No. 56, No. 57, No. 58, No. 59, No. 60, No. 61, No. 62, No. 63, No. 64, No. 65, No. 66, No. 67, No. 68, No. 69, No. 70, No. 71, No. 72, No. 73, No. 74, No. 75, No. 76, No. 77, No. 78, No. 79, No. 80, No. 81, No. 82, No. 83, No. 84, No. 85, No. 86, No. 87, No. 88, No. 89, No. 90, No. 91, No. 92, No. 93, No. 94, No. 95, No. 96, No. 97, No. 98, No. 99, No. 100, No. 101, No. 102, No. 103, No. 104, or No. 105 of Table 4, or any combination thereof is measured and is lower, e.g., at least about 25%, at least about 50%, at least about 90%, at least about 100%, at least about 1.5-fold, 2-fold, 2.5-fold, 3-fold, 3.5-fold, 4-fold, 4.5-fold, 5-fold or more, in the test cell compared to a non-leukemia stem cell, the test cell is classified as a T-cell ALL stem cell.

The levels of the stem cell markers of Table 3 or Table 4 can be measured using a microarray such as a SurePrint® G3 Human GE 8×60K microarray (Agilent Technologies, Santa Clara, Calif.), or a single-cell gene expression system. Such levels can be detected using, for example, one or more of the hybridization probes listed in Table 3 and/or Table 4, or an equivalent thereof.

D. Subpopulations of Leukemia Stem Cells

The present invention also provides a method for identifying and/or isolating a subpopulation (e.g., subclone) of leukemia stem cells from a sample (e.g., a biological sample or a cell culture sample) that contains a heterogeneous or mixed population of leukemia stem cells. In some embodiments, the method includes measuring the expression level of 1 to 93 leukemia stem cell markers set forth in Table 2 in a first leukemia stem cell, and comparing the expression level of the same leukemia stem cell markers in a second (different) leukemia stem cell from the mixed population. As described above, the expression level of the leukemia stem cell marker No. 1, No. 2, No. 3, No. 4, No. 5, No. 6, No. 7, No. 8, No. 9, No. 10, No. 11, No. 12, No. 13, No. 14, No. 15, No. 16, No. 17, No. 18, No. 19, No. 20, No. 21, No. 22, No. 23, No. 24, No. 25, No. 26, No. 27, No. 28, No. 29, No. 30, 31, No. 32, No. 33, No. 34, No. 35, No. 36, No. 37, No. 38, No. 39, No. 40, No. 41, No. 42, No. 43, No. 44, No. 45, No. 46, No. 47, No. 48, No. 49, No. 50, No. 51, No. 52, No. 53, No. 54, No. 55, No. 56, No. 57, No. 58, No. 59, No. 60, No. 61, No. 62, No. 63, No. 64, No. 65, No. 66, No. 67, No. 68, No. 69, No. 70, No. 71, No. 72, No. 73, No. 74, No. 75, No. 76, No. 77, No. 78, No. 79, No. 80, No. 81, No. 82, No. 83, No. 84, No. 85, No. 86, No. 87, No. 88, No. 89, No. 90, No. 91, No. 92, or No. 93 of Table 2, or any combination of the markers in Table 2, is measured in the sample. At least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, or 93 leukemia stem cell markers of Table 2 can be detected in a cell from the sample. If the expression level of the stem cell marker(s) of the first leukemia stem cell is higher and/or lower compared the expression level of the same stem cell marker(s) of the second leukemia stem cell, the first and second leukemia stem cell belong to separate (different or distinct) populations of stem cells. In some embodiments, the distinct subpopulations of leukemia stem cells can be separated and collected using standard methods such as cell sorting, e.g., FACS sorting.

In some embodiments, if the expression level of the measured leukemia stem cell marker(s) in the test leukemia stem cell is higher, e.g., at least about 25%, at least about 50%, at least about 90%, at least about 100%, at least about 1.5-fold, 2-fold, 2.5-fold, 3-fold, 3.5-fold, 4-fold, 4.5-fold, 5-fold or more, higher than the expression level of the same leukemia stem cell marker(s) in a second leukemia stem cell, it is determined that the test leukemia stem cell is distinct from the second leukemia stem cell and represent a separate (different or distinct) population of leukemia stem cells of the same leukemia disease.

In some embodiments, if the expression level of the measured leukemia stem cell marker(s) in the test cell is lower, e.g., at least about 25%, at least about 50%, at least about 90%, at least about 100%, at least about 1.5-fold, 2-fold, 2.5-fold, 3-fold, 3.5-fold, 4-fold, 4.5-fold, 5-fold or more, lower than the expression level of the same leukemia stem cell marker(s) in a non-leukemia stem cell, it is determined that the test leukemia stem cell belongs to a different population of leukemia stem cells. For example, the test and second leukemia stem cells are different types of leukemia stem cells of the same leukemia.

E. Determining the Cancer-Forming Ability of Cancer Stem Cells

The cancer-forming ability (tumor-initiating potential) of cancer stem cells (CSCs) isolated according to the methods provided herein can be assessed by transplanting the CSCs into a xenograft animal model. In particular embodiments, the leukemia stem cells (LSCs) isolated according to the methods provided herein are transplanted into a xenograft animal model to evaluate their leukemia initiating capacity. For example, the isolated LSCs can be injected into NOD/SCID/IL2Rγ null (NSG) mice which have no functional B-cells, T-cells, and natural killer cells (Fujii et al., *Pathol Int*, 2008, 58:559-567; NOD.Cg-Prkdc$^{scid}$ Il2g$^{tm1Wjl}$/Szj; Jackson Laboratory, Stock No. 005557), nude mice (Nu/J, Jackson Laboratory, Stock No. 002019), SCID mice (CB17/lcr-Prkdc$^{scid}$/lcrlcoCrl, Charles River, Strain Code 236), NOD-SCID mice (NOD.CB17-Prkdc$^{scid}$/J; Jackson Laboratory, Stock No. 001303), or nude rats (Crl:NIH-Foxn1$^{mu}$, Charles River, Strain Code 316).

The CSCs can be injected into the immunodeficient mice by various methods of injection or infusion, such as, but not limited to, subcutaneous, intramuscular, intravenous, intradermal, intraosseous, intraperitoneal, intrathecal, epidural, intracardiac, intraarticular, intracavernous, intravitreal, intracerebral, and intracerebroventricular. In some embodiments, LSCs are transplanted into the mouse by intra-tibial injection.

The presence of cancer in the CSC engrafted rodent can be evaluated by enumerating the solid tumors and/or the cancer cells in various organs of the animal by, for example, flow cytometry or immunocytochemistry. In some instances, a biomarker profile of solid tumors from an engrafted rodent can be obtained to show that the rodent has developed cancer due to the engrafted CSCs.

IV. Examples

The following examples are offered to illustrate, but not to limit, the claimed invention.

Example 1. Leukemia Stem Cells (LSCs) in Acute Lymphoblastic Leukemia (ALL): Unveiling Hierarchical Structure at Single Cell Resolution This example illustrates a novel method to isolate ALL LSCs based on their cellular metabolic activity. This example also shows that these isolated LSCs have in vivo leukemia-initiating capability (LIC). This example also describes a series of primary ALL xenograft mouse models generated from ALL patient samples and NOD/SCID/IL2Rγ$^{-/-}$ (NSG) mice.

Leukemia cells harvested from several generations of these mice were used in this study. LSCs and non-LSCs were isolated from 4 different B-cell type ALL samples and transplanted separately into healthy NSG mice. Cell numbers used varied between 5,000; 10,000; and 50,000 per mouse, and the number of the animals varied between three and eight per group. All the animals transplanted with LSCs developed leukemia between 5-14 weeks, whereas those transplanted with non-LSCs did not develop the disease within the same timeframe or by the end of the study.

In order to characterize and identify potential therapeutic targets of the LSCs, their transcriptome profile was investigated. First, genome-wide microarray gene expression profiling of RNA isolated from LSCs and non-LSCs using 4 ALL cell lines (Reh, JM1, Jurkat, and Molt4) was performed. There were 173 genes which showed at least a 2-fold difference in gene expression between LSCs and non-LSCs. Using a panel of primer sets for the 100 genes exhibiting the highest difference in expression, qRT-PCR was performed for these genes in the isolated LSCs and non-LSCs from 11 primary ALL samples (10 B-cell and 1 T-cell type) transplanted and harvested from the NSG xenograft mouse models at different generations. There was a distinct difference in the transcriptome profile between LSCs and non-LSCs in these primary ALL samples. Overall gene expression of 93 LSC signature genes was much lower in the LSCs than in the non-LSCs.

Recent advances in microfluidic technologies allows for the investigation of cells at single cell resolution. Growing evidence suggests that cancer stem cells consist of heterogeneous cell populations (subclones). Results using a primary ALL sample harvested from our xenograft mouse model and the Fluidigm C1™ and Biomark™ system indicate that there are at least two distinct subclones in the LSCs based on principal component analysis of the single cell data.

Materials and Methods

Reagents.

2-(N-(7-Nitrobenz-2-oxa-1, 3-diazol-4-yl) Amino)-2-Deoxyglucose (NBDG) was purchased from Life Technologies (Grand Island, N.Y.). Clinical-grade doxorubicin and vincristine (discarded after clinical use) were provided by the University of California (UC) Davis Pharmacy.

Cell Lines and Patient-Derived Leukemia Cells.

Four human ALL cell lines were used in this study: Jurkat (T-cell type ALL) provided by the Kit Lam laboratory at UC Davis and Reh (pre-B type ALL), JM1 (pre-B type ALL), and MOLT-4 (T-cell type ALL) were purchased from ATCC. Cells were maintained in 75 cm$^2$ plastic tissue culture-treated flasks (Corning Inc., Corning, N.Y.) at 37° C. in a 5% $CO_2$ incubator. The cell lines Jurkat, Reh, and MOLT-4 were grown in complete medium formulated with RPMI 1640 (Life Technologies, Carlsbad, Calif.) supplemented with 10% heat-inactivated fetal bovine serum (Thermo Scientific, Waltham, Mass.), 100 U/mL penicillin and 100 μg/mL streptomycin (Thermo Scientific), 0.25% D-glucose (Sigma-Aldrich, St Louis, Mo.), 1 mM sodium pyruvate (Thermo Scientific), and 10 mM HEPES buffer (Thermo Scientific). The cell line JM1 was grown in complete medium formulated with IMDM (Life Technologies) supplemented with 10% heat-inactivated fetal bovine serum (Thermo Scientific), 100 U/mL penicillin and 100 μg/mL streptomycin (Thermo Scientific), and 0.05 mM 2-mercaptoethanol (Life Technologies). Cells were manually washed and counted in PBS (Thermo Scientific) using trypan blue exclusion (0.04%, Sigma-Aldrich) and a hemocytometer. Cells were used within the first 25 passages and were maintained at their logarithmic phase of growth prior to each experiment.

Primary patient leukemia samples were collected from patients with informed consent based on the institutionally approved IRB protocol and transplanted into female NOD/SCID/IL2Rγ$^{-/-}$ (NSG) mice using our institutionally approved animal care protocol. As mice developed leukemia, they were sacrificed and leukemia cells were harvested from the leukemia-infiltrated spleen and bone marrow for experiments. Human leukemia cells were confirmed by flow cytometry using anti-HLA-ABC antibody (Biolegends, San Diego, Calif.).

Cell Isolation and Sorting.

Leukemic cells were resuspended in glucose-free Dulbecco's modified Eagle medium (DMEM) and incubated with NBDG at 37° C. in the dark for 30 minutes at 1 μL of 5 mg/mL NBDG per 3 million cells. After 30 minutes incubation, leukemic cells were washed with PBS. The cells were then stained with anti-HLA-APC antibody (Biolegends, San Diego, Calif.) and 4',6-Diamidino-2-Phenylindole, Dilactate (DAPI) (Life Technologies, Grand Island, N.Y.) according to the manufacturer's protocols. NBDG low and high cells were sorted by Cytopeia InFlux™ Cell Sorter (BD Biosciences, San Jose, Calif.).

Colony Forming Assay.

Cell lines sorted by high or low uptake of NBDG were further used for in vitro colony forming assays. These assays were most commonly performed in 24-well plates. The base agar (0.5%) was made by heating dried agar powder (Sigma-Aldrich) in heated sterile water to form a 5% agar solution. While still hot, the 5% agar solution was mixed with warm complete cell culture media at 1:10 ratio and poured into each well in 0.5 mL aliquots. The base was allowed to cool at room temperature.

Before plating cells on the agar base, a top agarose solution was prepared and kept warm in a 37° C. bath. The top agarose solution (0.35%) was made by heating agarose powder in sterile water to form a 3.5% solution. This agarose solution was mixed with warm complete media at a 1:10 ratio.

Low-NBDG and high-NBDG cells were resuspended separately in the warm top agarose solution at 2,500 cells/mL. Each well was aliquoted with 0.5 mL of the cell/top agarose solution for a final count of 1,250 cells per well. The optimal seeding density had been previously determined in earlier titration experiments testing growth rate of colonies when seeding 500, 1,000, and 1,250 cells per well. Each population had triplicate wells seeded for counting. Colonies were counted every 3 days for up to 50 days after the initial seeding.

MTS Assay.

The 50% inhibitory concentrations (IC50) of doxorubicin and vincristine for four human ALL cell lines were determined by the CellTiter 96® AQueous Non-Radioactive Cell Proliferation Assay, which uses 3-(4,5-dimethylthiazol-2-yl)-5-β-carboxymethoxyphenyl)-2-(4-sulfophenyl)-2H-tetrazolium (MTS) (Promega, Madison, Wis.) and an electron coupling reagent, phenazine methosulfate (PMS) (Sigma-Aldrich, St. Louis, Mo.).

Cells were plated at 10,000 cells/50 μL complete medium/well in a 96-well tissue-culture treated plate in triplicate for each treatment condition. To determine the optimal plating density of 10,000 cells/well, an initial titration experiment was performed with 5,000, 10,000, 20,000, 40,000, and 80,000 cells/well in a 96-well tissue-culture treated plate in duplicate for each cell line. After the cells were incubated at 37° C. for 72 hours, the level of confluency within the well and the color change after the addition of MTS and PMS solutions were evaluated. Five concentrations of doxorubicin and vincristine were prepared from five-fold serial dilutions in complete medium. Then, 50 μL of each drug concentration was added to the medium in triplicate and cells were incubated at 37° C. for 72 hours. MTS (2 μg/μL) and PMS (0.92 μg/μL) solutions were prepared according to manufacturer's instructions. MTS and PMS solutions were mixed using a 20:1 (MTS:PMS) ratio before 10 μL was added to each well. After cells were incubated at 37° C. for an additional 2 to 4 hours, absorbance at 490 nm was measured using a microplate reader. Background absorbance of the medium was subtracted to obtain corrected absorbance values. The percentage of viable cells was calculated using the absorbance values relative to the untreated controls. The average IC50 values of doxorubicin and vincristine for each ALL cell line was calculated from three experiments using GraphPad Prism® Software (San Diego, Calif.).

For each experiment, the calculated IC50 values from adding MTS and using GraphPad Prism® Software were compared to the cell viability based on manual cell counting. Triplicate wells were combined and cells were manually washed and counted in PBS using trypan blue exclusion (0.04%, Sigma-Aldrich) and a hemocytometer. Cells from the following treatment conditions were manually counted: untreated controls, the most diluted drug concentration from the serial dilutions, the drug concentration similar to the calculated IC50 value, and the most concentrated drug concentration from the serial dilutions. The percentage of viable cells was calculated using the number of live cells relative to the untreated controls.

Leukemia Cell Transplantation.

Human leukemia mouse models from 11 ALL patient samples by intra-tibial injection. Cell numbers transplanted ranged from 100 to $2.5 \times 10^6$ cells per mouse. When the mouse developed leukemia, leukemia cells were harvested from the bone marrow as well as leukemia infiltrated spleen and liver, and transplanted into new NSG mice (2nd generation mice). 2nd, 3rd, 4th generation mice were made. By using leukemic cells harvested from these 11 xenograft mouse models (2nd to 4th generation), gene expression profiles were analyzed from RNA extracted from the sorted NBDG low and high cells. In addition, sorted cells from 6 xenograft mouse models were evaluated for their ability to promote leukemogenesis (the induction and development of leukemia). All leukemic cells engrafted in the new NSG mice.

Sorted cells from 6 different xenografted leukemia cells were transplanted into NSG mice by intra-tibial injections. The cell numbers varied between 100 to 50,000 cells per mouse depending on the cell numbers available. The number of mice per each series was 20 to 30 mice. Mice were monitored daily and euthanized when they showed signs of sickness. Leukemia cells were harvested from bone marrow, spleen or liver. The mice were checked daily for signs of sickness, such as unkempt fur, ataxia or weight loss of more than 20% of pre-treatment body weight, in accordance with IACUC policy on Humane Endpoints. These mice were euthanized and leukemia was confirmed by autopsy. In some instances, if the mice looked healthy, the mice were observed for up to an additional 4 months. Afterwards the mice were euthanized, and the presence of leukemia was evaluated by autopsy and flow cytometry.

RNA Isolation.

Human ALL xenografts and cell lines were enriched by cell sorting into culture medium, pelleted by centrifugation, and stored at −80° C. Total cellular RNA was isolated from the cell pellets (73,942-433,703 cells) using the TRIzol® reagent (Life Technologies) and a modified protocol that incorporates an additional extraction with phenol/chloroform/isoamyl alcohol (25:24:1, pH 4.3). RNA quantity and quality were assessed on a NanoDrop™ spectrophotometer (Thermo Scientific) and the Agilent 2100 Bioanalyzer (Agilent Technologies, Santa Clara, Calif.), respectively.

Microarray Gene Expression Profile.

Total RNA was extracted using TRIzol® reagent (Invitrogen) and RNA integrity evaluated by analysis with the Agilent 2100 Bioanalyzer (Agilent Technologies). Microarray analysis was performed by the UC Davis Comprehensive Cancer Center Genomics Shared Resource. Genome-wide expression profiling was performed using SurePrint® G3 Human Gene Expression 8×60K v2 Microarrays (Design ID 028004; Agilent Technologies) for the analysis of 27,958 Entrez Gene RNAs and 7,419 lincRNAs. Preparation of fluorescently-labeled cRNA samples and array hybridization, washing, and scanning were performed according to Agilent's optimized protocols. Briefly, the one-color Low Input Quick Amp Labeling protocol (Agilent Technologies) was used to prepare fluorescently-labeled cRNA from input RNA samples (100 ng) by T7 RNA Polymerase-based linear amplification and incorporation of Cyanine 3-CTP. Subsequently, labeled cRNA samples (1.65 µg) were fragmented, combined with Hi-RPM Hybridization Buffer, and then hybridized to arrays at 65° C. for 17 hours. Microarrays were washed with Agilent Gene Expression Wash Buffers 1 and 2 containing 0.005% Triton X-102 for 1 minute at room temperature and at 37° C., respectively. Microarray slides were then scanned with an Agilent G2565CA high-resolution scanner followed by data extraction with Agilent Feature Extraction software.

Microarray Data Analysis.

Data analysis was performed with the GeneSpring® GX (version 12) software suite (Agilent Technologies). Briefly, quantile normalization and log-transformation was applied to probe intensity values from the feature extraction files. Data was filtered on raw intensity values in the 20th-100th percentile of expression. Comparison analysis was then performed in order to identify genes that were differentially expressed between the different cell populations. Criteria for the selection of genes exhibiting expression changes included an average fold change of ≥1.5 between groups (i.e., low vs. high) with paired t-test results of p≤0.05. An LSC signature profile was arrived at by downstream filtering of the data for differentially expressed genes and lncRNAs that were either in common to LSCs (i.e., "Low" cell population) from multiple cell types or exhibited prominent expression changes in LSCs from a single cell type.

Single Cell Isolation and Preparation of cDNA Pre-Amplification Products.

Single-cell gene expression profiling analysis was performed utilizing the C1™ Single-Cell Auto Prep and BioMark™ HD Systems (Fluidigm Corporation, So. San Francisco, Calif.). For this, sorted LSC populations from ALL xenografts were microfluidically separated into single cells on the C1™ system fitted with an AutoPrep Integrated Fluidic Circuit (IFC; 5-10 µm size) for cell capture followed by cell lysis, reverse transcription, and pre-amplification with pooled DELTAgene™ assay primers (500 nM) and reagents from the Ambion® Single Cell-to-CT Kit (Life Technologies). Amplified cDNA products (3 µl) were harvested and diluted in DNA Dilution Reagent (Fluidigm Corporation).

Quantitative RT-PCR Analysis of Cell Sorted ALL Sub-Population Pools and Single-Cell Sample.

Bulk cell populations and single cells were analyzed for the expression of LSC signature genes with qRT-PCR using a custom-designed panel of DELTAgene™ assays (Fluidigm Corporation) with the BioMark HD system (Fluidigm Corporation). Real-time qPCR assays were performed with SsoFast™ EvaGreen® Supermix with Low ROX (Bio-Rad Laboratories, Hercules, Calif.) on the BioMark HD System (Fluidigm Corporation) using Dynamic Arrays™ IFCs (96.96). Data analysis was performed with Fluidigm Real-Time PCR Analysis Software and SINGuLAR™ Analysis Toolset 3.5 packages for delta delta Ct calculations secondary analyses including principal component analysis, analysis of variance (ANOVA), and hierarchical clustering.

Results

A. Characterization of the Isolated LSCs from ALL

Figure 1B:
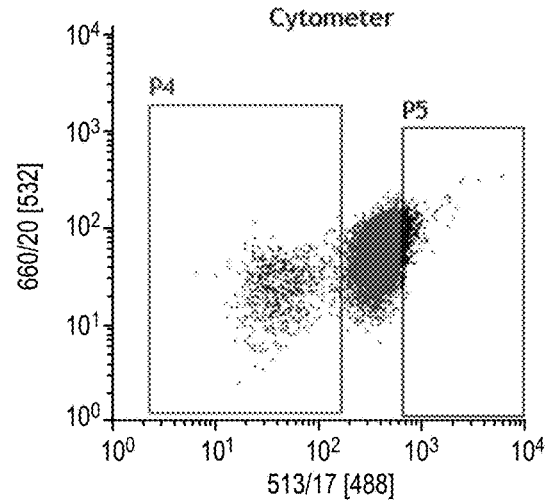
Figure 1C:
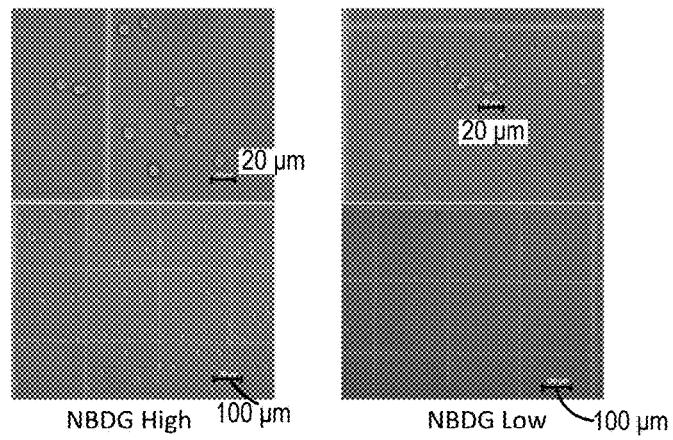
Figure 2A:
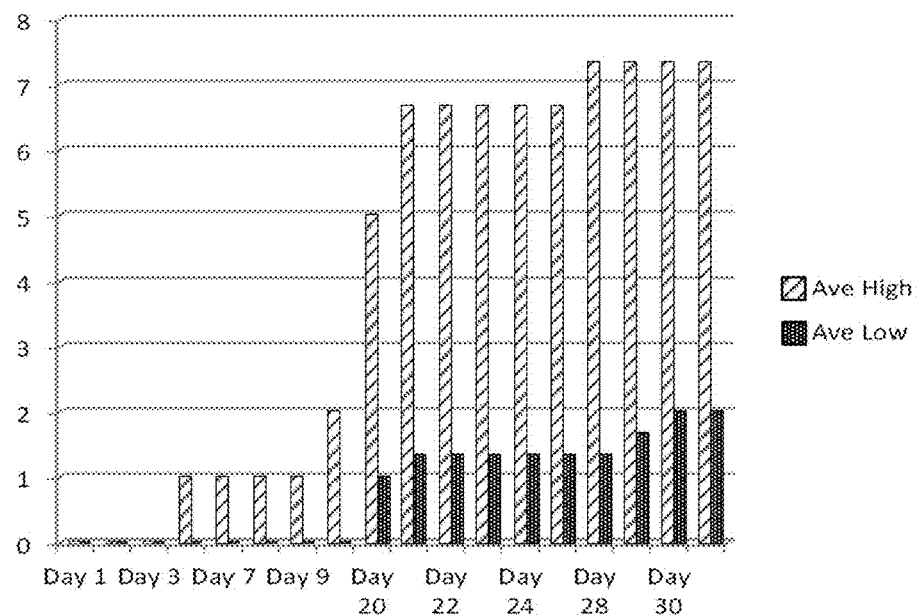
FIGS. 2A-C show that cancer stem cells with low NBDG fluorescence were isolated from the Reh cell line of pre-B lymphocyte cells from a patient with acute lymphoblastic leukemia (ALL). These cells have less colony forming capacity in an in vitro assay (FIG. 2A), have lower HLA expression compared to NBDG high cells from the same cell line (FIG. 2B) and are smaller in size as determined by phase contrast microscopy (FIG. 2C).
Figure 2B:
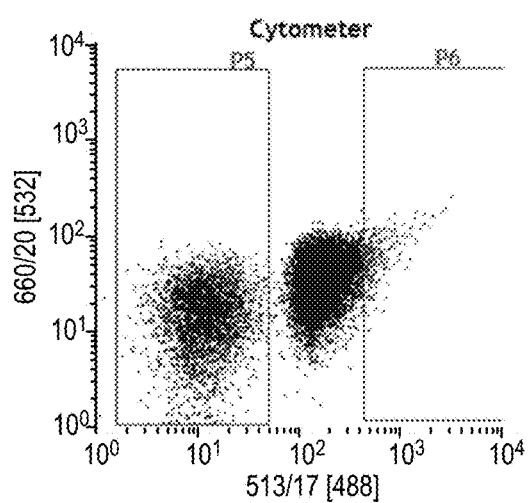
Figure 2C:
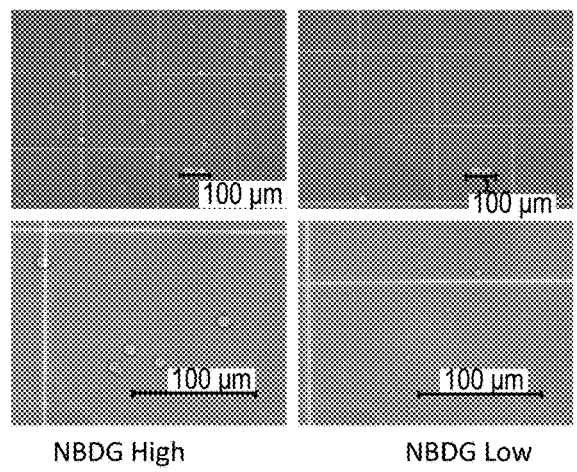
Figure 3A:
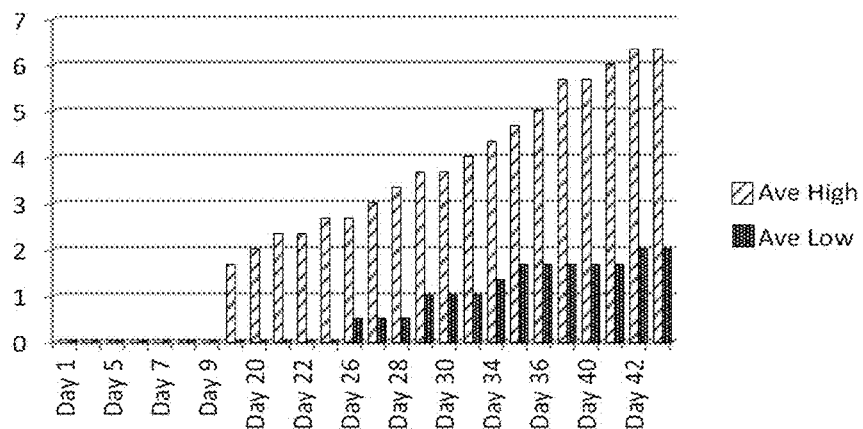
FIGS. 3A-C show that cancer stem cells with low NBDG fluorescence were isolated from the Jurkat cell line of T lymphocyte cells derived from a human patient with acute lymphoblastic leukemia (ALL). These cells formed fewer colonies in an in vitro colony forming assay (FIG. 3A), have lower HLA expression compared to NBDG high Jurkat cells (FIG. 3B) and are smaller in size as determined by phase contrast microscopy (FIG. 3C).
Figure 3B:
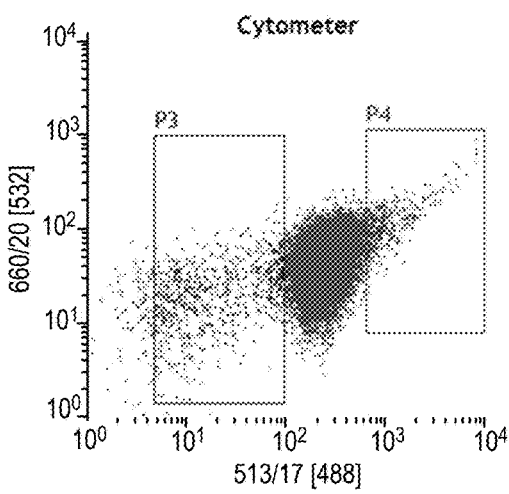
Figure 3C:
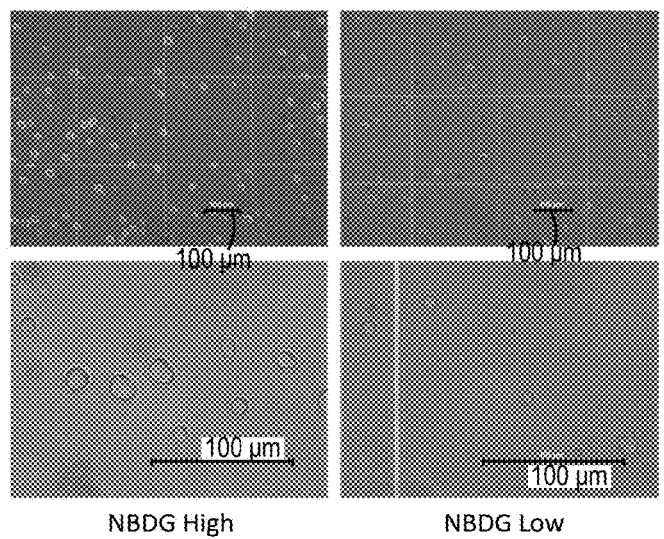
Figure 5A:
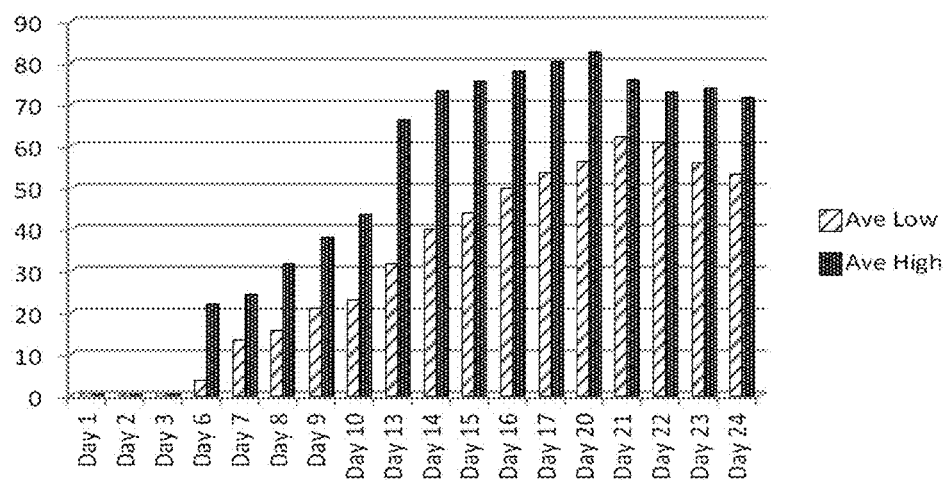
FIGS. 5A-B show that leukemia stem cells with low NBDG fluorescence were isolated from the K562 cell line derived from a patient with chronic myelogenous leukemia. These cells formed fewer colonies in an in vitro colony forming assay (FIG. 5A) and have lower HLA expression (P7) compared to NBDG high K562 cells (P8 in FIG. 5B).
Figure 5B:
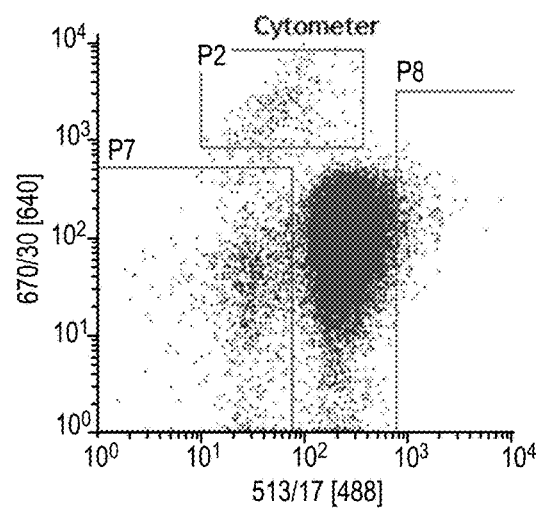

Four ALL cell lines (JM1 [FIGS. 1A-C], Reh [FIGS. 2A-C], Jurkat [FIGS. 3A-C], and MOLT-4 [FIGS. 4A-C]) and one AML cell line (K562 [FIGS. 5A-B]) were sorted for low and high NBDG populations. For each sample 20 to 60×10$^6$ cells were grown and harvested during their logarithmic growth for cell sorting. Post-sort cell count showed that low NBDG cells ranged from 15,000 to 500,000 per sample (~1% of the whole population). Low NBDG cells from cell lines and patient-derived samples were small in size. The cell diameters for high and low NBDG cells ranged from 7.41 to 13.99 µm, and from 4.21 to 7.41 µm, respectively. The low NBDG cells also showed lower HLA expression than the high NBDG cells.

In vitro colony forming assays were performed using 5 cell lines described above (FIGS. 1A, 2A, 3A, 4A and 5A). Colonies were first observed between 5-25 days in the high NBDG cells, while LSC colonies were first observed between 6-36 days in the low NBDG cells. Colonies were monitored and counted up to 50 days after seeding. The average colony counts for high:low NBDG cells were 16.25: 7.33 for JM1, 12.17:6.54 for Reh, 5.5:1.33 for Jurkat, and 4.08:0.58 for MOLT-4. Primary ALL sorted cells did not grow colonies in the soft agar medium.

B. In Vivo Leukemia Initiating Capability of the Isolated LSCs

Figure 11:
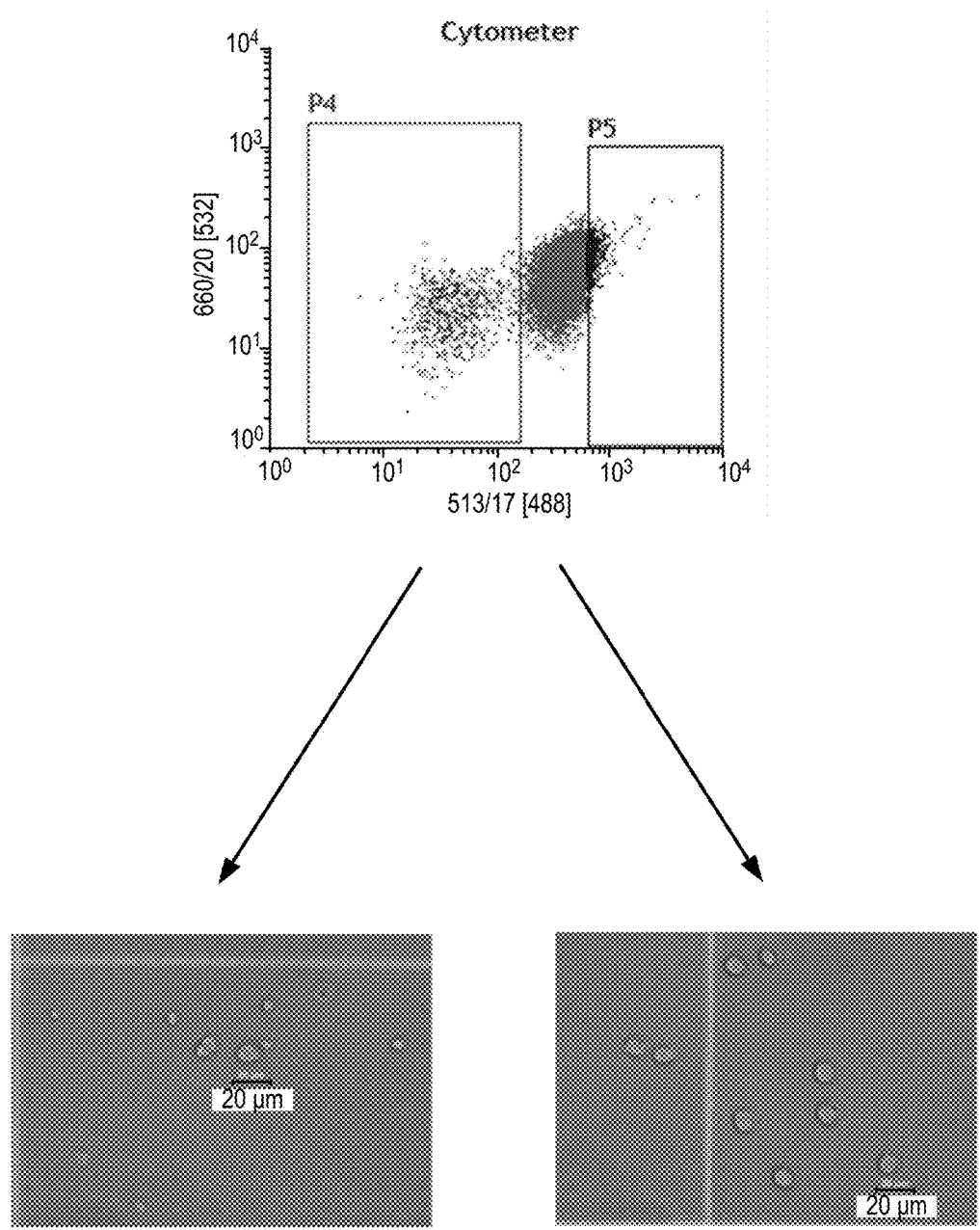
FIG. 11 illustrates that freshly sorted patient-derived leukemia stem cells have a lower level of fluorescence (P4) compared to other cells that are not leukemia stem cells and have a higher level of fluorescence (P5) due to NBDG uptake. The data show that leukemia stem cells have less efficient glucose uptake or metabolism compared to the other sorted cells, such as the non-leukemia stem cells.
Figure 13A:
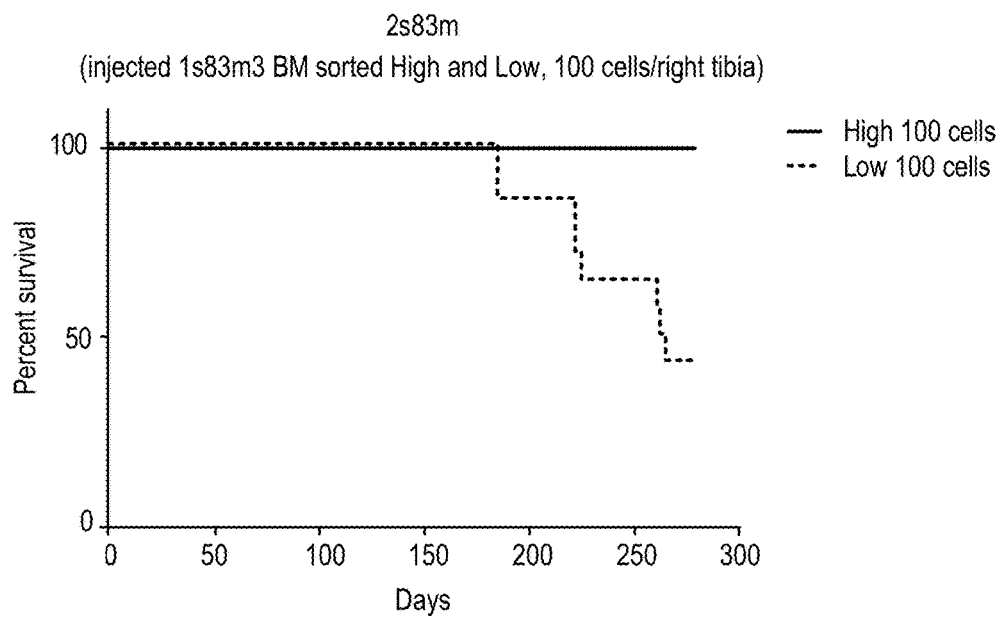
FIGS. 13A-B illustrate that NOD/SCID/IL-2R$\gamma^{-/-}$ mice transplanted with 100 patient derived leukemia stem cells developed leukemia between 15-36 weeks post-transplantation, whereas almost all mice transplanted with cells having a high level of NBDG did not develop the disease within the same timeframe.
Figure 13B:
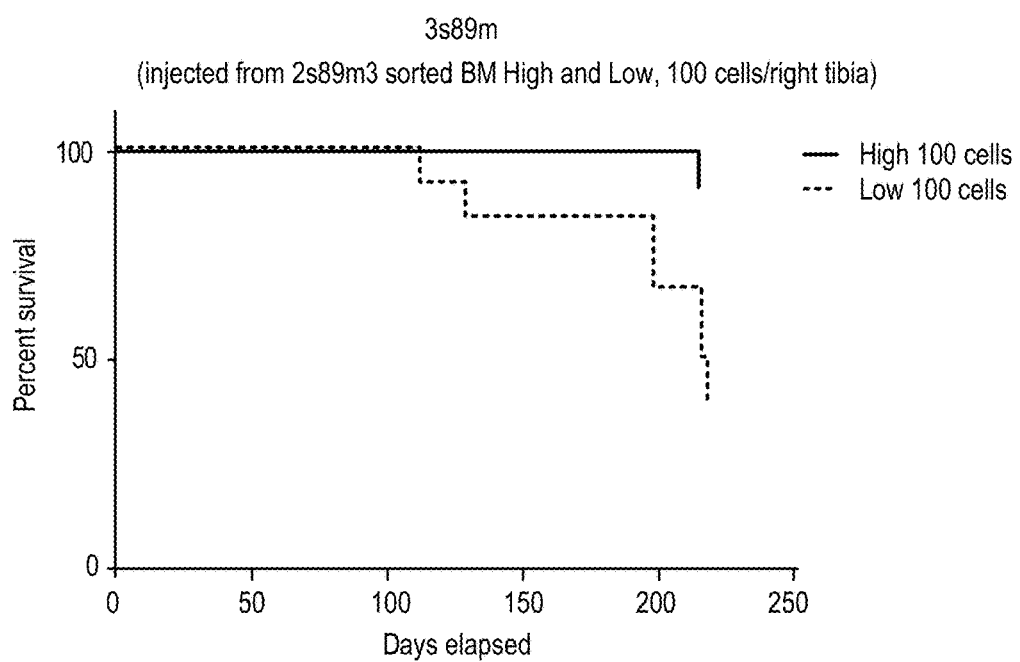

Low and high NBDG cells were isolated from 4 different B-cell type ALL patient samples (primary patient samples) and transplanted them separately into healthy NOD/SCID/IL-2Rγ$^{-/-}$ (NSG) mice (FIG. 11). Cell numbers used varied between 5,000, 10,000 and 50,000 per mouse, and the number of animals varied between three and eight per group. All the animals transplanted with low NBDG cells developed leukemia between 5-14 weeks (the median survival time of each different leukemia sample; #1 (4s90m; FIG. 12A) 53.5 days, #2 (2s96m; FIG. 12B) 36 days, #3 (4s86m; FIG. 12C) 82 days, #4 (3s83m; FIG. 12D) 98.5 days), whereas those transplanted with high NBDG cells did not develop the disease within the same timeframe or by the end of the study, which was more than 4 months after leukemia development in the LSC group (the median survival time of each different leukemia sample; #1 (4s90m; FIG. 12A) 187 days, #2 (2s96m; FIG. 12B) 173.5 days, #3 (4s86m; FIG. 12C) 171 days, #4 (3s83m; FIG. 12D) 193 days). All of the mice except one (3s83m) of the high NBDG groups did not develop leukemia and they survived significantly longer than the low NBDG groups (until the endpoint of the studies) (p=0.0018-0.01 by log-rank test). At the end of the study, the mice of the high NBDG group except from 3s83m were sacrificed and none exhibited evidence of leukemia. Transplantation was also performed using a much smaller cell dose of 100 cells per mouse in 2 samples (FIGS. 13A and 13B). Some animals developed leukemia in the low NBDG cell transplanted group, whereas all animals except one from the 3s89m did not develop leukemia in the high NBDG transplanted group.

C. Transcriptome Assays

Genome-wide microarray gene expression profiling of RNA isolated from the LSCs and non-LSCs was performed using 4 ALL cell lines (Reh, JM1, Jurkat, and Molt4). There were 173 genes which showed at least 2-fold difference in gene expression between the LSCs and non-LSCs. Using a panel of primer sets for the 93 genes exhibiting the highest difference in expression, qRT-PCR was performed for these genes in the isolated LSCs and non-LSCs from 11 primary ALL samples (10 B-cell and 1 T-cell type ALL patient samples) transplanted and harvested from the NSG xenograft mouse models at different generations. There was a distinct difference in the transcriptome profile between the LSCs and non-LSCs in these primary ALL samples. Overall gene expression of 93 LSC signature genes was much lower in the LSCs than in the non-LSCs (Table 1).

D. Single Cell Transcriptome Profiling Indicates Subclones in the LSCs

Recent advances in microfluidic technologies allowed us to investigate cells at single cell resolution. Growing evidence suggests that cancer stem cells consist of heterogeneous cell populations (subclones). Therefore, using the Fluidigm C1™ and Biomark™ system it was investigated whether these isolated LSCs have subclones.

Figure 14:
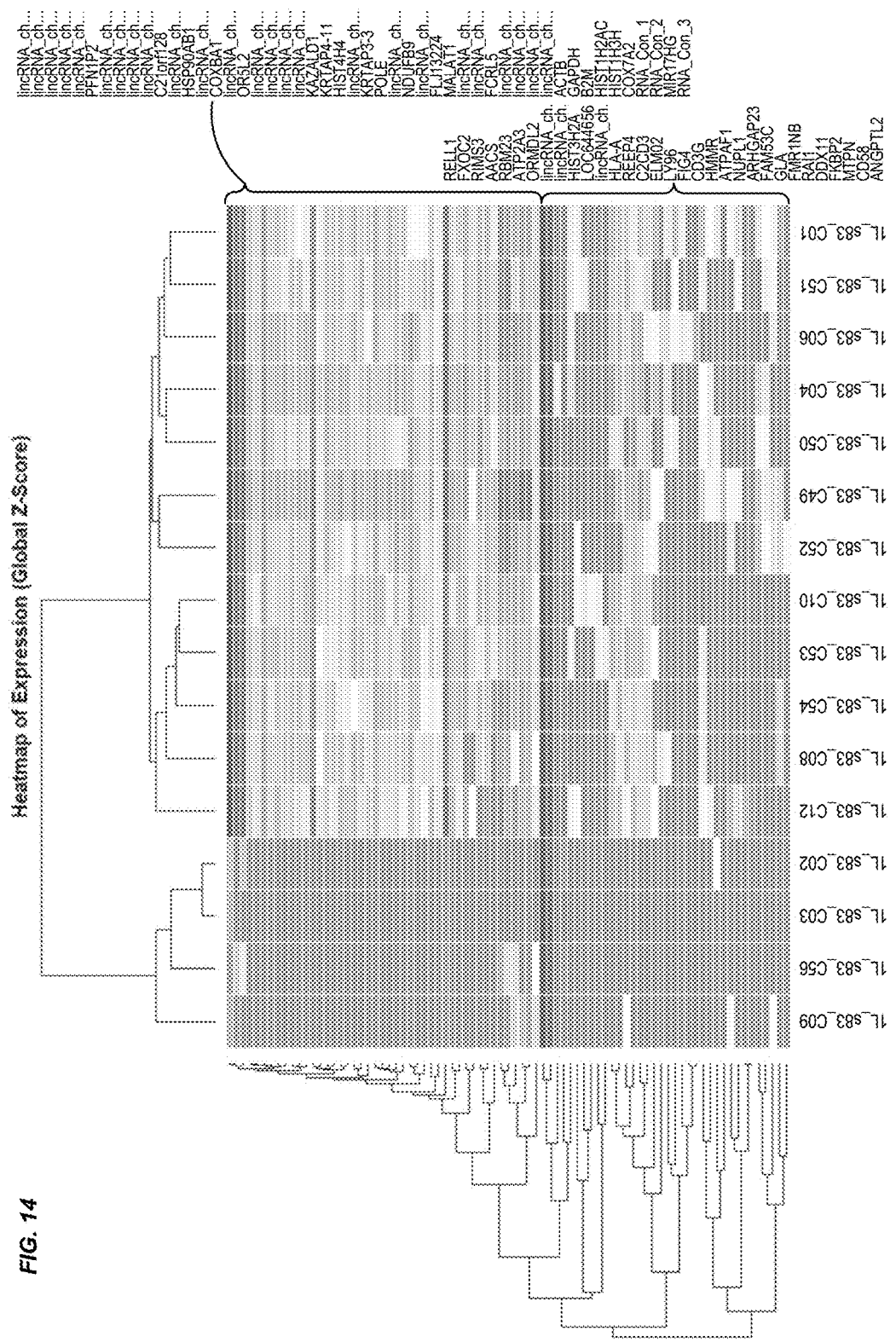
FIG. 14 shows that single cell transcriptome profiling data indicating that there are distinct populations or subclones in the LSCs isolated according to the methods described herein.
Figure 15:
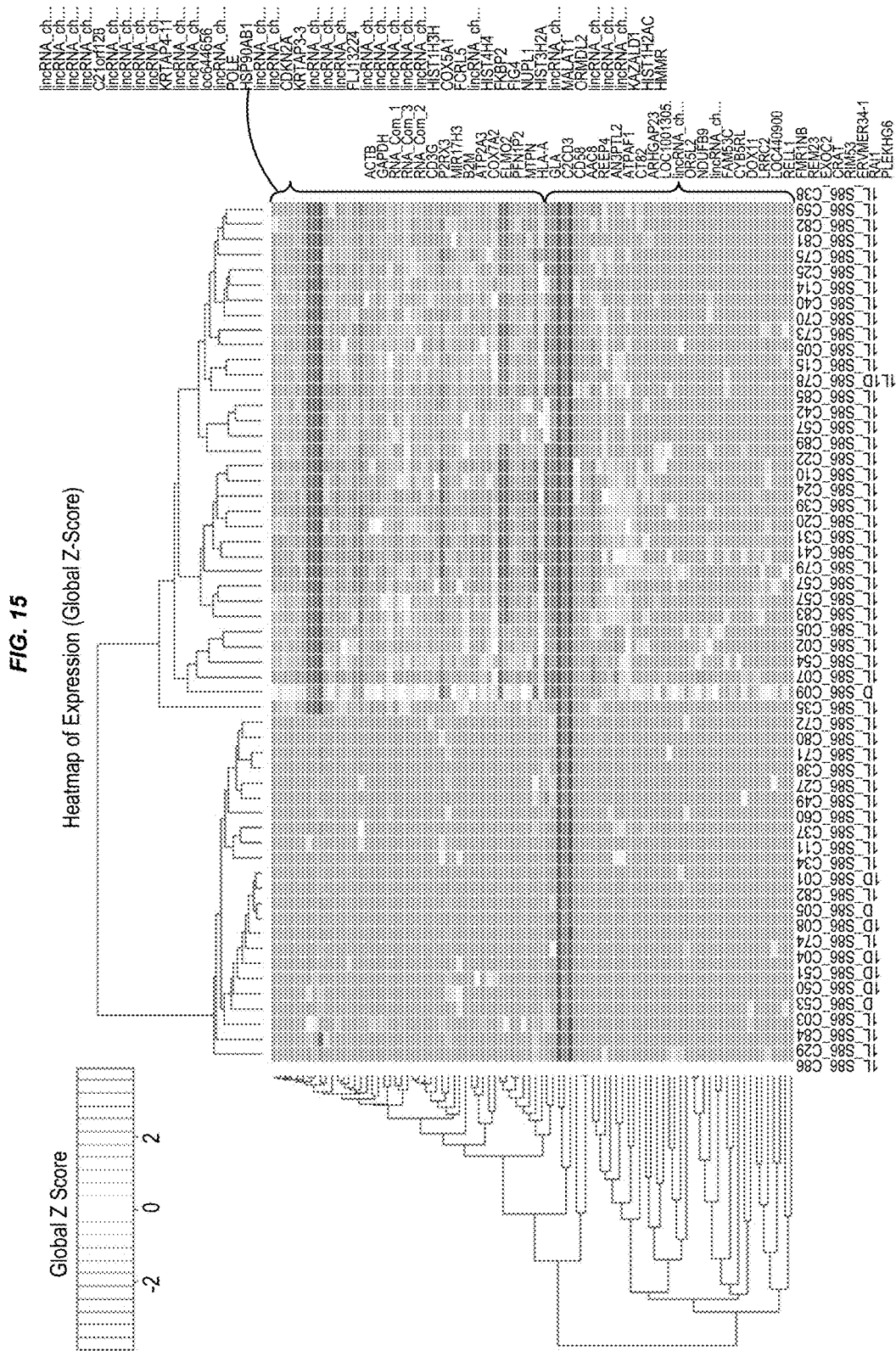
FIG. 15 shows hierarchical clustering of single-cell gene expression data from another primary ALL sample (1s88).
Figure 16:
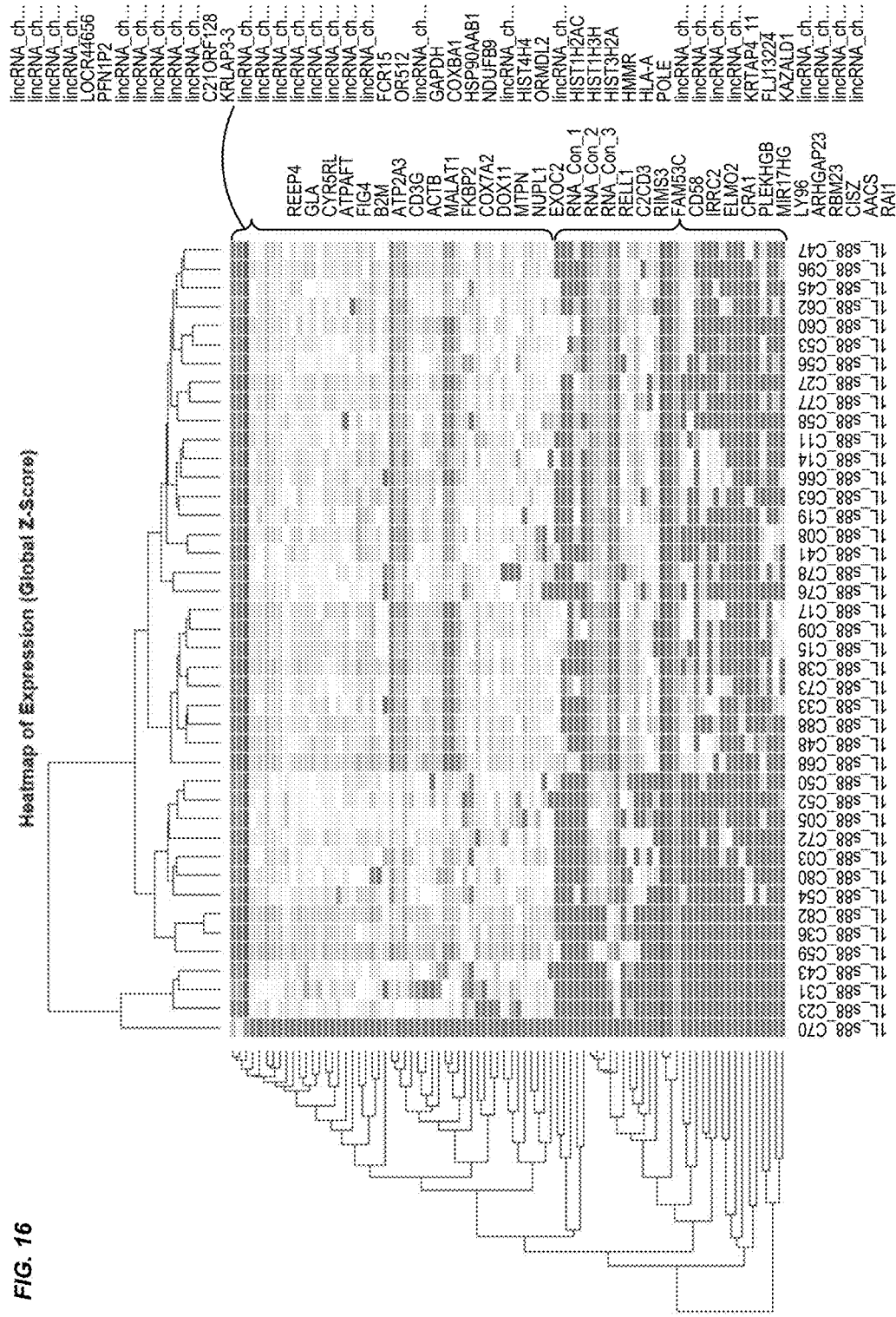
FIG. 16 shows hierarchical clustering of single-cell gene expression data from another primary ALL sample (3s86).

The expression level of 93 stem cell markers listed in Table 2 which were previously tested in the bulk (pooled) LSC and non-LSC samples described above were detected in single cells from 3 different ALL samples. The data shows that there are heterogeneous populations with different transcriptome profiles (of these 93 genes), thereby suggesting the existence of LSC subclones (FIGS. 14-16). In the 3 primary ALL samples harvested from the xenograft mouse models, there are at least two distinct subclones of the LSCs in each of the 3 primary ALL samples analyzed (FIGS. 14-16). Additionally, the profile of each subclone is different among the 3 different ALL samples, i.e., the number of subclones and transcriptome profile of each clone.

E. Neuroblastoma

Figure 6A:
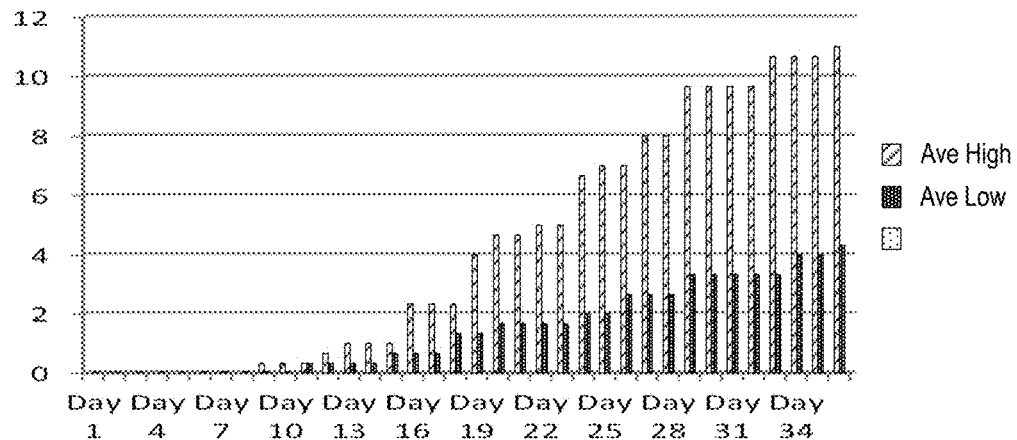
FIGS. 6A-C show that cancer stem cells with low NBDG fluorescence were isolated from the neuroblastoma cell line SK-N-BE. These cells formed fewer colonies in an in vitro colony forming assay (FIG. 6A), have lower HLA expression compared to NBDG high SK-N-BE cells (P5 vs. P6 in FIG. 6B) and are smaller in size as illustrated by phase contrast microscopy (FIG. 6C).
Figure 6B:
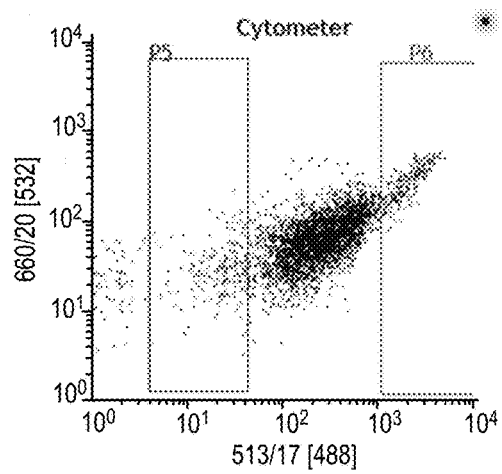
Figure 6C:
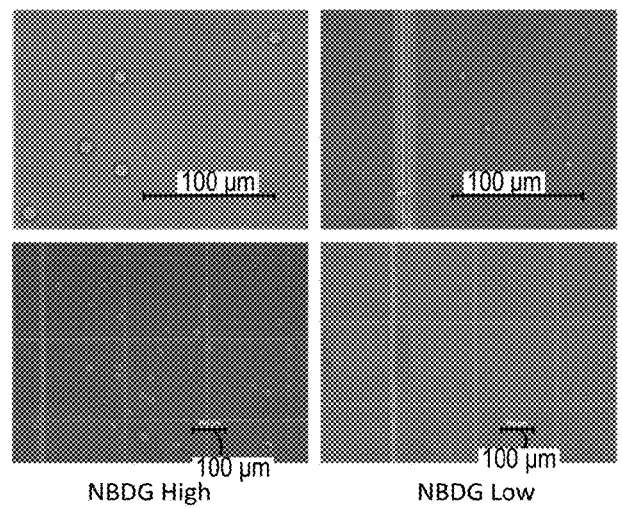
Figure 7A:
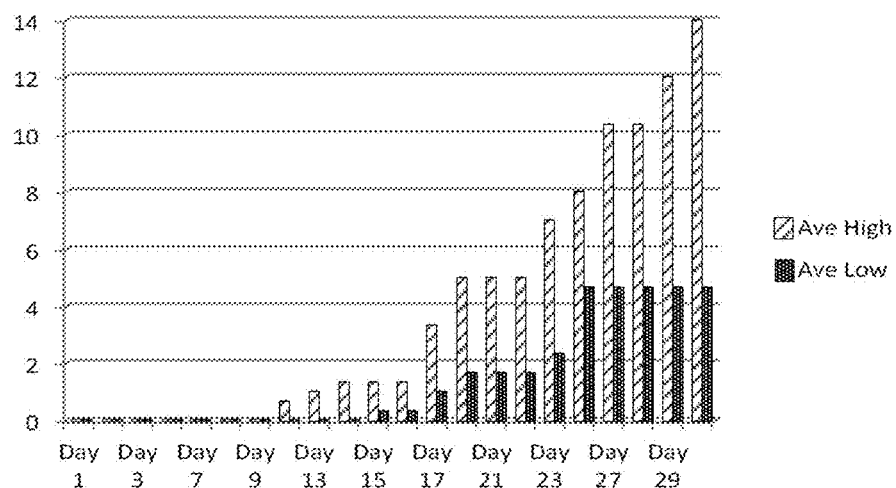
FIGS. 7A-C show that neuroblastoma stem cells with low NBDG fluorescence were isolated from the neuroblastoma cell line SK-N-DZ. These cells formed fewer colonies in an in vitro colony forming assay (FIG. 7A), have lower HLA expression compared to NBDG high SK-N-DZ cells (FIG. 7B) and are smaller in size as illustrated by phase contrast microscopy (FIG. 7C).
Figure 7B:
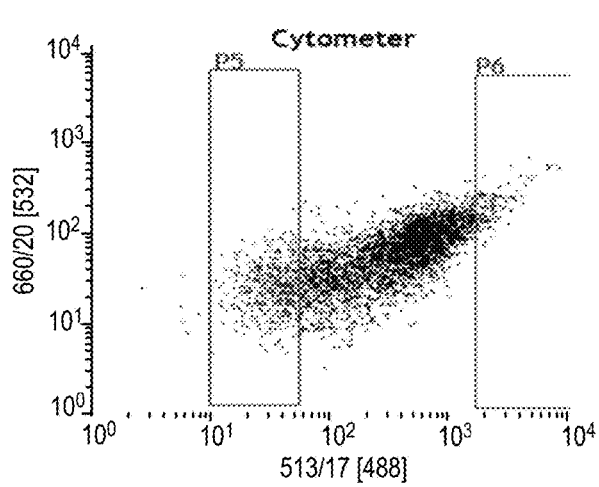
Figure 7C:
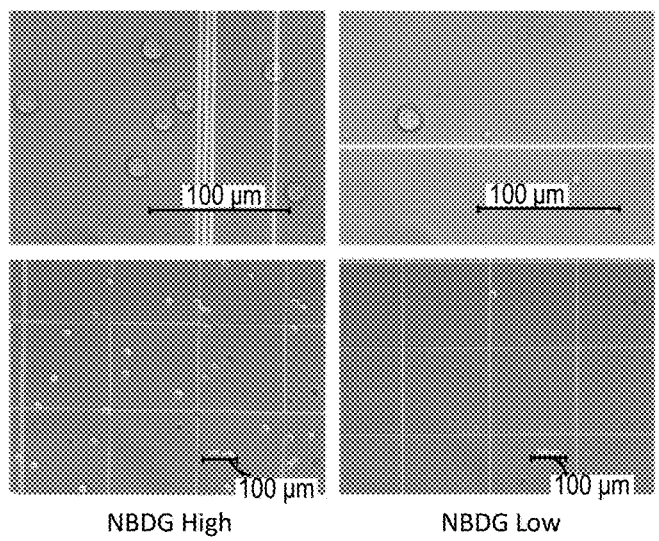
Figure 8A:
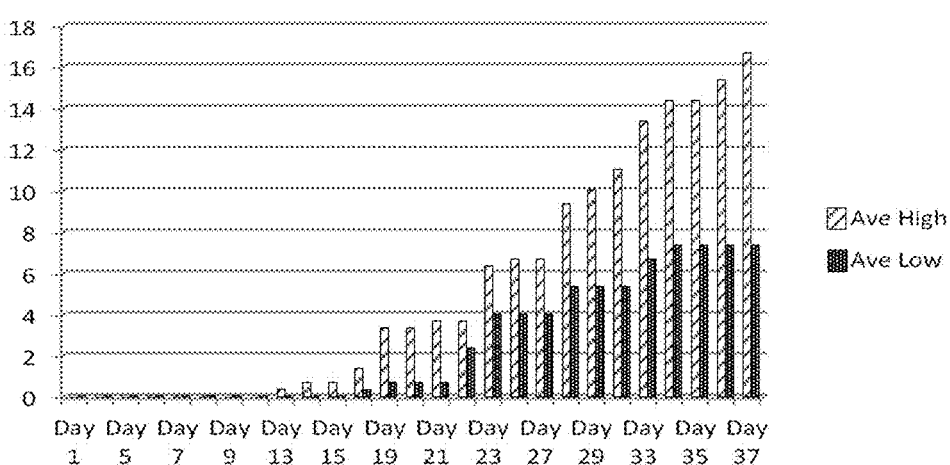
FIGS. 8A-C show that neuroblastoma stem cells with low NBDG fluorescence were isolated from the neuroblastoma cell line IMR32 which is derived from metastatic cells found in a stomach tumor of a patient with neuroblastoma. These cells formed fewer colonies in an in vitro colony forming assay (FIG. 8A), have lower HLA expression compared to NBDG high IMR32 cells (P5 vs. P6 in FIG. 8B) and are smaller in size as illustrated by phase contrast microscopy (FIG. 8C).
Figure 8B:
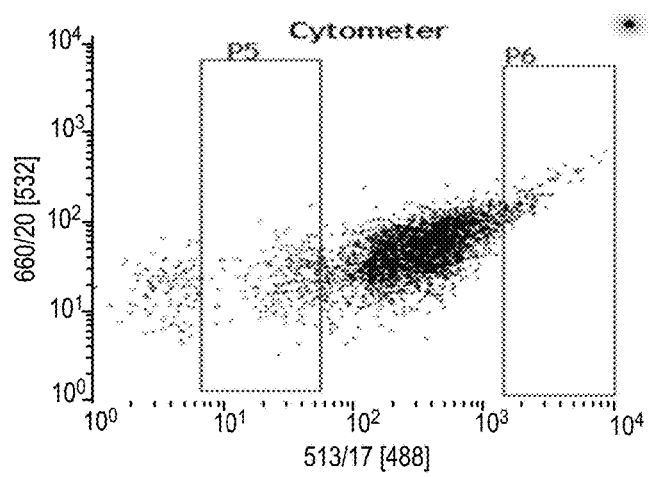
Figure 8C:
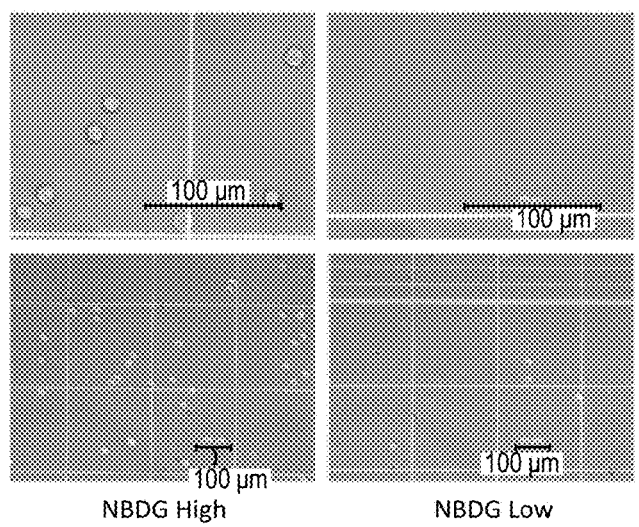
Figure 9A:
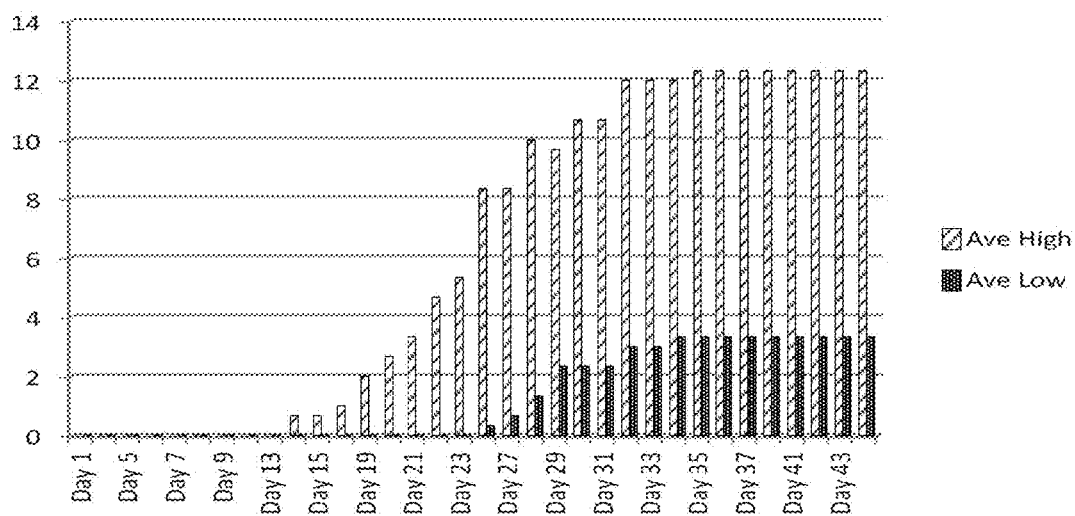
FIGS. 9A-B show that neuroblastoma stem cells with low NBDG fluorescence were isolated from the neuroblastoma cell line SK-N-SH derived from metastatic cells found in the bone marrow aspirate of a patient with neuroblastoma. These cells formed fewer colonies in an in vitro colony forming assay (FIG. 9A) and have lower HLA expression compared to NBDG high SK-N-SH cells (P5 vs. P6 in FIG. 9B).
Figure 9B:
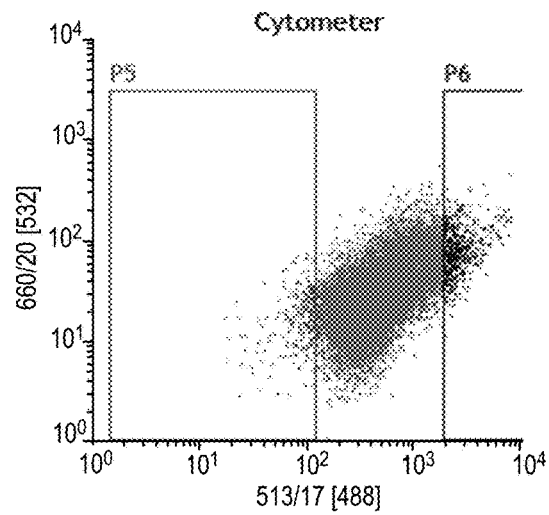
Figure 10A:
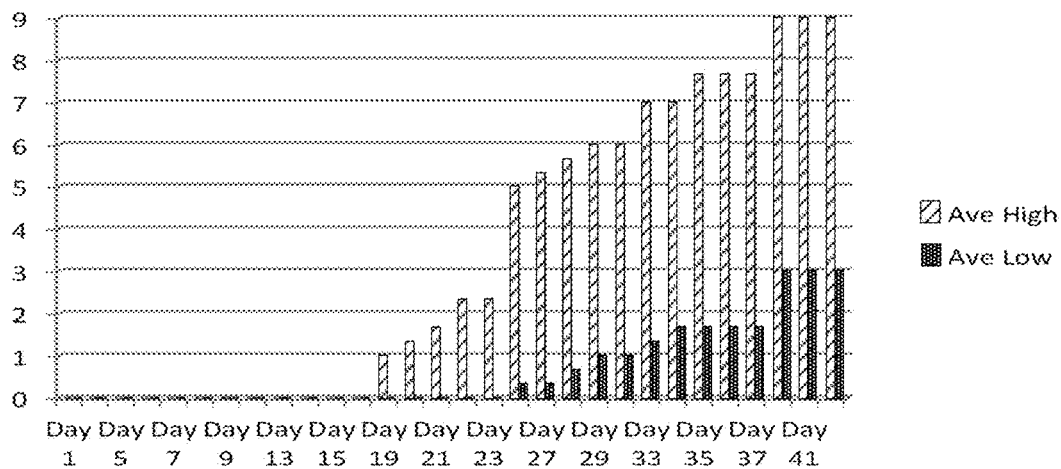
FIGS. 10A-C show that neuroblastoma stem cells with low NBDG fluorescence were isolated from the cell line SH-SY5Y which is derived from a bone marrow biopsy from a patient with neuroblastoma. These cells formed fewer colonies in an in vitro colony forming assay (FIG. 10A), have lower HLA expression compared to NBDG high SH-SY5Y cells (P4 vs. P5 in FIG. 10B) and are smaller in size as illustrated by phase contrast microscopy (FIG. 10C).
Figure 10B:
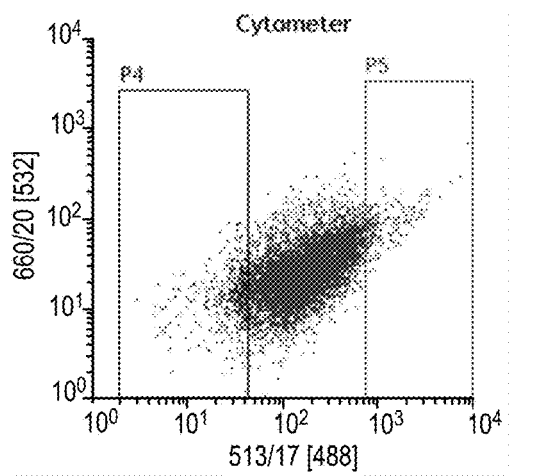
Figure 10C:
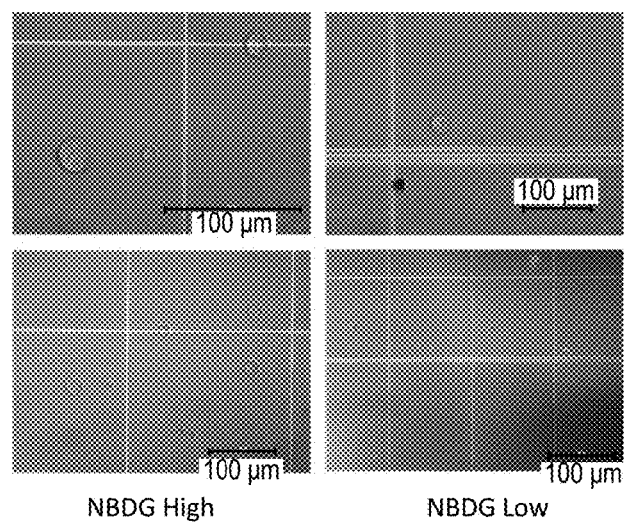

Glucose uptake using NBDG was tested in neuroblastoma cells. Very similar results to the leukemia study were observed. A distinct cell population, which is NBDG low, was identified in 5 different neuroblastoma cell lines (SK-NB-E ([FIGS. 6A-C], SK-N-DZ [FIGS. 7A-C], IMR32 [FIG. 8A-C], SK-N-SH [FIG. 9A-B], SH-SY5Y [FIG. 10A-C]). These cells are, in general, smaller in size compared to the high NBDG cells (FIGS. 6C, 7C, 8C, and 10C). The low NBDG cells formed colonies, but fewer and slower than the high NBDG cells (FIGS. 7A, 8A, 9A, and 10A). MTS assay showed that these low NBDG low cells were more resistant to chemotherapy drugs (e.g., vincristine or doxorubicin) than the high NBDG cells.

In summary, this example illustrates a novel method to isolate acute lymphoblastic leukemia stem cells (LSCs) which have in vivo leukemia-inducing capacity. The example demonstrates that isolated LSCs have a distinct transcriptome profile, and shows that the LSCs consist of subclones. The results also show that low NBDG cells are quiescent leukemia stem cells. This example shows that cancer stem cells from various neuroblastoma cell lines can also be isolated based on the glucose uptake as measured by NBDG fluorescence. As with LSCs, neuroblastoma stem cells have low level of NBDG fluorescence compared to other neuroblastoma cells.

These isolated cancer stem cells may be used to identify and develop CSC-targeted therapeutics, including subclone-specific targeted drugs. In addition, methods for detecting cancer stem cells, including specific subtypes or subpopulations may be used to diagnose a specific type of cancer, to monitor cancer progression and therapeutic response, or to distinguish normal and malignant cell pools in a subject.

Example 2. Leukemia Stem Cells (LSCs) in B-Cell Acute Lymphoblastic Leukemia (B-Cell ALL)

This example describes the results of a genome-wide microarray gene expression profiling of RNA isolated from the JM1 cell line. The experimental procedures are described in Example 1. Briefly, JM1 cells were treated with NBDG and FACS sorted to isolate two cell populations: a low NBDG group and a high NBDG group. The cells of each group were subject to transcriptome analysis using a gene expression microarray (SurePrint® G3 Human Gene Expression 8×60K v2 Microarray, Agilent Technologies). The data is provided in Table 3. There was an average fold change of ≥1.5 between the groups (i.e., low NBDG vs. high NBDG) with paired t-test results of p≤0.05. 80 genes exhibited a differential expression level between B-cell ALL stem cells and non-B-cell ALL stem cells. The expression level difference for each of the 80 genes was statistically significant.

Example 3. Leukemia Stem Cells (LSCs) in T-Cell Acute Lymphoblastic Leukemia (T-Cell ALL)

This example describes the results of a genome-wide microarray gene expression profiling of RNA isolated from the Molt4 cell line. The experimental procedures are described in Example 1. Briefly, Molt4 cells were treated with NBDG and FACS sorted to isolate two cell populations: a low NBDG group and a high NBDG group. The cells of each group were subject to transcriptome analysis using a gene expression microarray (SurePrint® G3 Human Gene Expression 8×60K v2 Microarray, Agilent Technologies). The data is provided in Table 4. There was an average fold change of ≥1.5 between the groups (i.e., low NBDG vs. high NBDG) with paired t-test results of p≤0.05. 105 genes exhibited a differential expression level between T-cell ALL stem cells and non-T-cell ALL stem cells. The expression level difference for each of the 105 genes was statistically significant.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for selecting cancer stem cells from a sample, the method comprising (a) incubating the sample with a fluorescent glucose analog under suitable conditions, wherein the sample is a biological sample obtained from a subject with acute lymphoblastic leukemia (ALL) or a cell culture sample comprising cells from an ALL cell line, and wherein the sample comprises cancer stem cells and non-cancer stem cells; b) measuring or detecting the level of fluorescence in the sample; and (c) selecting the cancer stem cells from the sample based upon a lower level of fluorescence compared to the non-cancer stem cells.

2. The method of claim 1, further comprising isolating the cancer stem cells.

3. The method of claim 1, wherein the cancer stem cells are capable of initiating cancer in an animal model.

4. The method of claim 1, wherein the non-cancer stem cells have highly efficient glucose uptake.

5. The method of claim 1, wherein the biological sample is selected from the group consisting of bone marrow, blood, plasma, serum, cerebrospinal fluid, a tumor biopsy, a tissue biopsy, a fine needle aspirate, circulating tumor cells, and combinations thereof.

6. The method of claim 1, wherein the acute lymphoblastic leukemia (ALL) is B-cell ALL or T-cell ALL.

7. The method of claim 1, wherein the fluorescent glucose analog is selected from the group consisting of 2-[N-(7-nitrobenz-2-oxa-1,3-diaxol-4-yl)amino]-2-deoxyglucose (2-NBDG), 6-deoxy-N-(7-nitrobenz-2-oxa-1,3-diazol-4-yl) aminoglucose (6-NBDG), pyro-2DG, Cy5.5-D-glucosamine (Cy5.5-2DG), Cy3-linked O-1-glycosylated glucose (Cy3-α-glucose and Cy3-β-glucose), IRDye 800CW 2-DG, CyNE 2-DG, GB3-Cy3, other fluorescent glucose analogs, and combinations thereof.

8. The method of claim 1, wherein the cancer stem cells are selected using flow cytometry.

9. The method of claim 1, wherein the lower level of fluorescence of the cancer stem cells is at least about 1-log lower compared to the non-cancer stem cells.

* * * * *